(12) United States Patent
Davis

(10) Patent No.: US 10,918,629 B2
(45) Date of Patent: Feb. 16, 2021

(54) METHOD FOR TREATING LYMPHEDEMA

(71) Applicant: The Curators of the University of Missouri, Columbia, MO (US)

(72) Inventor: Michael John Davis, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 18 days.

(21) Appl. No.: 15/520,008

(22) PCT Filed: Oct. 20, 2015

(86) PCT No.: PCT/US2015/056400
§ 371 (c)(1),
(2) Date: Apr. 18, 2017

(87) PCT Pub. No.: WO2016/064832
PCT Pub. Date: Apr. 28, 2016

(65) Prior Publication Data
US 2017/0333412 A1     Nov. 23, 2017

Related U.S. Application Data

(60) Provisional application No. 62/122,413, filed on Oct. 20, 2014.

(51) Int. Cl.
*A61K 31/4422* (2006.01)
*A61K 31/18* (2006.01)
*A61K 31/137* (2006.01)
*A61K 31/135* (2006.01)

(52) U.S. Cl.
CPC ........ *A61K 31/4422* (2013.01); *A61K 31/135* (2013.01); *A61K 31/137* (2013.01); *A61K 31/18* (2013.01)

(58) Field of Classification Search
CPC .............. A61K 31/4422; A61K 31/135; A61K 31/137; A61K 31/18
See application file for complete search history.

(56) References Cited

U.S. PATENT DOCUMENTS

| | | |
|---|---|---|
| 4,241,046 A | 12/1980 | Papahadjopoulos et al. |
| 4,394,448 A | 7/1983 | Szoka et al. |
| 4,529,561 A | 7/1985 | Hunt et al. |
| 4,755,388 A | 7/1988 | Heath et al. |
| 4,828,837 A | 5/1989 | Uster et al. |
| 4,853,216 A | 8/1989 | Koslo et al. |
| 4,925,661 A | 5/1990 | Huang |
| 4,954,345 A | 9/1990 | Muller |
| 4,957,735 A | 9/1990 | Huang |
| 5,043,164 A | 8/1991 | Huang et al. |
| 5,064,655 A | 11/1991 | Uster et al. |
| 5,077,211 A | 12/1991 | Yarosh |
| 5,264,618 A | 11/1993 | Felgner et al. |
| 2010/0130615 A1 | 5/2010 | Gant |
| 2011/0033936 A1 | 2/2011 | Nakamura et al. |
| 2014/0274905 A1* | 9/2014 | Pitt ........................ A61K 38/08 514/16.7 |

FOREIGN PATENT DOCUMENTS

DE    3741414 A1    12/1987

OTHER PUBLICATIONS

Bian and Hermsmeyer (J Vasc Res 1994;31:256-264, abstract only). (Year: 1994).*
Davis et al., "Lymphatic valve lock in response to modest gravitational loads: a contributing mechanism to peripheral lymphedema?" 2012, The FASEB Journal, 2 pages.
International Search Report and Written Opinion related to Application No. PCT/US2015/056400, dated Dec. 11, 2015, 10 pages.
Murphy, et al., "Hormonal effects on calcium homeostasis in isolated hepatocytes." The Journal of Biological Chemistry, 1980, vol. 255, No. 14, pp. 6600-6608.
Aukland, et al., "Interstitial-lymphatic mechanisms in the control of extracellular fluid volume." Physiol Rev 73: 1-78, 1993.
Bates et al., "Starling forces in the human arm and their alteration in postmastectomy oedema." Journal of Physiology 477: 355-363, 1994.
Bazigou et al., "Integrin-alpha9 is required for fibronectin matrix assembly during lymphatic valve morphogenesis." Developmental Cell 17: 175-186, 2009.
Beckett et al., "Spontaneous electrical activity in sheep mesenteric lymphatics." Lymphatic Research & Biology 5: 29-43, 2007.
Bian et al., "Glyburide actions on the dihydropyridine-sensitive Ca2+ channel in rat vascular muscle." J Vasc Res. Sep.-Oct. 1994;31(5):256-64. (Abstract only).
Benoit et al., "Characterization of intact mesenteric lymphatic pump and its responsiveness to acute edemagenic stress." American Journal of Physiology (Heart and Circulatory Physiology) 257: H2059-H2069, 1989.
Bertram et al., "Simulation of a chain of collapsible contracting lymphangions with progressive valve closure." J Biomech Eng. Jan. 2011;133(1):011008.
Brice et al., "Milroy disease and the VEGFR-3 mutation phenotype." Journal of Medical Genetics 42: 98-102, 2005.
Brice et al., "Analysis of the phenotypic abnormalities in lymphoedema-distichiasis syndrome in 74 patients with FOXC2 mutations or linkage to 16q24." Journal of Medical Genetics 39: 478-483, 2002.
Chen et al., "Interaction of capillary, interstitial, and lymphatic forces in the canine hindpaw." Circulation Research 39: 245-254, 1976.
Clifford et al., "Spatial distribution and mechanical function of elastin in resistance arteries: a role in bearing longitudinal stress." Arterioscler Thromb Vasc Biol 31: 2889-2896, 2011.
Clough et al., "Simultaneous measurement of pressure in the interstitium and the terminal lymphatics of the cat mesentery." Journal of Physiology 283: 457-468, 1978.
(Continued)

Primary Examiner — Kortney L. Klinkel
Assistant Examiner — William Y Lee
(74) Attorney, Agent, or Firm — Polsinelli PC

(57) ABSTRACT

The disclosure relates to the field of lymphedema therapy, more specifically, to a new pharmacological strategy to rescue the failed lymph pump system that can supplement, enhance or replace current therapies.

12 Claims, 43 Drawing Sheets
(43 of 43 Drawing Sheet(s) Filed in Color)

(56) References Cited

OTHER PUBLICATIONS

Kesler et al., "Lymphatic vessels in health and disease." Wiley Interdiscip Rev Syst Biol Med 5: 111-124, 2013.
Davis, "Control of bat wing capillary pressure and blood flow during reduced perfusion pressure." American Journal of Physiology (Heart and Circulatory Physiology) 255: H1114-H1129, 1988.
Davis et al., "Myogenic constriction and dilation of isolated lymphatic vessels." American Journal of Physiology (Heart and Circulatory Physiology) 296: H293-H302, 2009.
Davis et al., "Capillary pressures in rat intestinal muscle and mucosal villi during venous pressure elevation." American Journal of Physiology (Heart and Circulatory Physiology) 249: H174-H187, 1985.
Davis et al., "A new preparation for microcirculatory studies of the hamster cheek pouch." American Journal of Physiology (Heart and Circulatory Physiology) 248: H143-H146, 1985.
Davis et al., "Microvascular pressure distribution and responses of pulmonary allografts and cheek pouch arterioles in the hamster to oxygen." Circulation Research 49: 125-132, 1981.
Davis et al., "Modulation of lymphatic muscle contractility by the neuropeptide substance P." American Journal of Physiology (Heart and Circulatory Physiology) 295: H587-H597, 2008.
Davis et al., "Determinants of valve gating in collecting lymphatic vessels from rat mesentery." American Journal of Physiology (Heart and Circulatory Physiology) 301: H48-H60, 2011.
Davis et al., "Intrinsic increase in lymphatic muscle contractility in response to elevated afterload." American Journal of Physiology (Heart and Circulatory Physiology) 303: H795-H808, 2012.
Davis, "An improved, computer-based method to automatically track internal and external diameter of isolated microvessels." Microcirculation vol. 12, p. 361-372, 2005.
Drake et al., "Effect of outflow pressure on intestinal lymph flow in unanesthetized sheep." American Journal of Physiology (Regulatory, Integrative and Comparative Physiology) 260: R668-R671, 1991.
Eisenhoffer et al., "Importance of valves and lymphangion contractions in determining pressure gradients in isolated lymphatics exposed to elevations in outflow pressure." Microvasc Res 49: 97-110, 1995.
Engeset et al., "Twenty-four hour variation in flow and composition of leg lymph in normal men." Acta Physiol Scandinavica 99: 140-148, 1977.
Fang et al., "Mutations in FOXC2 (MFH-1), a forkhead transcription factor, are responsible for the hereditary lymphedema-distichiasis syndrome." American Journal of Human Genetics 67: 1382-1387, 2000.
Finegold et al. "Truncating mutations in FOXC2 cause multiple lymphedema syndromes." Human Molecular Genetics 10: 1185-1189, 2001.
Gashev et al., "Methods for lymphatic vessel culture and gene transfection." Microcirculation 16: 615-628, 2009.
Gashev et al., "Inhibition of the active lymph pump by flow in rat mesenteric lymphatics and thoracic duct." Journal of Physiology 450: 1023-1037, 2002.
Goldman et al., "Regulation of lymphatic capillary regeneration by interstitial flow in skin." American Journal of Physiology (Heart and Circulatory Physiology) 292: H2176-H2183, 2007.
Greene et al., "Lower-extremity lymphedema and elevated body-mass index." New England Journal of Medicine 366: 2136-2137, 2012.
Hagendoorn et al., "Endothelial nitric oxide synthase regulates microlymphatic flow via collecting lymphatics." Circ Res 95: 204-209, 2004.
Hargens et al., "Gravitational haemodynamics and oedema prevention in the giraffe." Nature 329: 59-60, 1987.
Hargens et al., "Contractile stimuli in collecting lymph vessels." American Journal of Physiology (Heart and Circulatory Physiology) 233: H57-H65, 1977.

Humphrey, "Pharmacology of the K-ATP Channel Blocking Morpholinoguanidine PNU-37883A." Cardiovascular Drug Reviews 17(4):295-328, 1999.
Iida et al., "Essential roles of the winged helix transcription factor MFH-1 in aortic arch patterning and skeletogenesis." Development 124: 4627-4638, 1997.
Kriederman et al., "FOXC2 haploinsufficient mice are a model for human autosomal dominant lymphedema-distichiasis syndrome." Human Molecular Genetics 12: 1179-1185, 2003.
Leduc et al., "Impact of manual lymphatic drainage on hemodynamic parameters in patients with heart failure and lower limb edema." Lymphology 44: 13-20, 2011.
Levick et al., "Microvascular fluid exchange and the revised Starling principle." Cardiovascular Research 87: 198-210, 2010.
Liao et al., "Impaired lymphatic contraction associated with immunosuppression." Proc Natl Acad Sci U S A 108: 18784-18789, 2011.
Maejima et al., "Platelet-Derived Growth Factor (PDGF)-BB Produces NO-Mediated Relaxation and PDGF Receptor b-Dependent Tonic Contraction in Murine Iliac Lymph Vessels." Microcirculation 18: 474-486, 2011.
McHale et al., "The effect of transmural pressure on pumping activity in isolated bovine lymphatic vessels." J Physiol 261: 255-269, 1976.
Mellor et al., "Mutations in FOXC2 in humans (Lymphoedema Distichiasis Syndrone) cause lymphatic dysfunction on dependency." Journal of Vascular Research 48: 397-407, 2011.
Mendez et al., "Functional recovery of fluid drainage precedes lymphangiogenesis in acute murine foreleg." American Journal of Physiology (Heart and Circulatory Physiology) 302: H2250-H2256, 2012.
Mendez et al., "A chronic and latent lymphatic insufficiency follows recovery from acute lymphedema in the rat foreleg." American Journal of Physiology (Heart and Circulatory Physiology) 303: H1107-H1113, 2012.
Mizuno et al., "Parathyroid hormone-related protein-(1-34) inhibits intrinsic pump activity of isolated murine lymph vessels." Am J Physiol Heart Circ Physiol 281: H60-66, 2001.
Modi et al., "Human lymphatic pumping measured in healthy and lympoedematous arms by lymphatic congestion lymphoscintography." Journal of Physiology 583: 271-285, 2007.
Mortimer et al., "Chronic peripheral oedema: the critical role of the lymphatic system." Clinical Medicine 4: 448-453, 2004.
Normen et al., "FOXC2 controls formation and maturation of lymphatic collecting vessels through cooperation with NFATc1." Journal of Cell Biology 195: 439-457, 2009.
Olszewski, "Contractility patterns of normal and pathologically changed human lymphatics." Annals of the New York Academy of Science 979: 52-63, 2002.
Olszewski et al., "Intrinsic contractility of leg lymphatics in man: preliminary communication." Lymphology 12: 81-84, 1979.
Olszewski et al., "Intrinsic contractility of prenodal lymph vessels and lymph flow in human leg." American Journal of Physiology (Heart and Circulatory Physiology) 239: H775-H783, 1980.
Ono et al., "Development of an experimental apparatus for investigating lymphatic pumping activity of murine mesentery in vivo." Japanese J Physiology 50: 25-31, 2000.
Petrova et al., "Defective valves and abnormal mural cell recruitment underlie lymphatic vascular failure in lymphedema distichiasis." Nature Medicine 10: 974-981, 2004.
Rockson, "Lymphedema." Curr Treat Options Cardiovasc Med 8: 129-136, 2006.
Rockson, "Precipitating factors in lymphedema: myths and realities." Cancer 15: 2814-2816, 1998.
Rockson, "Secondary lymphedema: is it a primary disease?" Lymphatic Research & Biology 6: 63-64, 2008.
Rockson et al., "Estimating the population burden of lymphedema." Annals of the New York Academy of Science 1131: 147-154, 2008.
Rutkowski et al., "Secondary lymphedema in the mouse tail: Lymphatic hyperplasia, VEGF-C upregulation, and the protective role of MMP-9." Microvasc Res 72: 161-171, 2006.
Sabine et al., "Mechanotransduction, PROX1, and FOXC2 cooperate to control connexin37 and calcineurin during lymphatic-valve formation." Developmental Cell 22: 1-16, 2012.

(56) References Cited

OTHER PUBLICATIONS

Scallan et al., "Genetic ablation of nitric oxide enhances contractile function of murine isolated popliteal afferent collecting lymphatic vessels." Journal of Physiology 591: 2139-2156, 2013.
Scallan et al., "Constriction of isolated collecting lymphatic vessels in response to acute increases in downsteam pressure." Journal of Physiology 591: 443-449, 2012.
Scallan et al., "Independent and interactive effects of preload and afterload on the lymphatic pump." American Journal of Physiology (Heart and Circulatory Physiology) 303: H809-H824, 2012.
Schmid-Schönbein, "Microlymphatics and lymph flow." Physiological Reviews 70: 987-1028, 1990.
Shin et al., "Animal models for the study of lymphatic insufficiency." Lymphatic Research & Biology 1: 159-169, 2003.
Stanton et al., "Recent advances in breast cancer-related lymphedema of the arm: lymphatic pump failure and predisposing factors." Lymphatic Research & Biology 7: 29-45, 2009.
Stanton et al., "Lymphatic drainage in the muscle and subcutis of the arm after breast cancer treatment." Breast Cancer Research Treatment 117: 549-557, 2009.
Szuba et al., "Lymphedema: anatomy, physiology and pathogenesis." Vascular Medicine 2: 321-326, 1997.
Szuba et al., "The third circulation: radionuclide lymphoscintigraphy in the evaluation of lymphedema." Journal of Nuclear Medicine 44: 43-57, 2003.
Tilney, "Patterns of lymphatic drainage in the adult laboratory rat." Journal of Anatomy 109: 369-383, 1971.
Trayes et al., "Edema: Diagnosis and Management." American Family Physician 88: 102-110, 2013.
Uzarski et al., "The resolution of lymphedema by interstitial flow in the mouse tail skin." American Journal of Physiology (Heart and Circulatory Physiology) 294: H1326-H1334, 2008.
Von Der Weid et al., "Lymphatic smooth muscle: the motor unit of lymph drainage." Int J Biochem Cell Biol 36: 1147-1153, 2004.
Wang et al., "Inhibition of myosin light chain phosphorylation decreases rat mesenteric lymphatic contractile activity." American Journal of Physiology (Heart and Circulatory Physiology) 297: H726-H734, 2009.
Wegria et al., "Effect of systemic venous pressure on drainage of lymph from thoracic duct." American Journal of Physiology 204: 284-268, 1963.
Weitman et al., "Obesity impairs lymphatic fluid transport and dendritic cell migration to lymph nodes." PLoS One 8: e70703, 2013.
Wiig et al., "Interstitial fluid and lymph formation and transport: physiological regulation and roles in inflammation and cancer." Physiological Reviews 92: 1005-1060, 2012.
Witte et al., "Lymph circulation in congestive heart failure: Effect of external thoracic duct drainage." Circulation 39: 723-733, 1969.
Zaugg-Vesti et al., "Lymphatic capillary pressure in patients with primary lymphedema." Microvasc Res 46: 128-134, 1993.
Zhang et al., "Maximum shortening velocity of lymphatic muscle approaches that of striated muscle." Am J Physiol Heart Circ Physiol 15;305(10):H1494-507, 2013.
Zweifach et al., "Micromanipulation of pressure in terminal lymphatics in the rat mesentery." American Journal of Physiology 228: 1326-1335, 1975.

\* cited by examiner

METHOD FOR TREATING LYMPHEDEMA

CROSS REFERENCE TO RELATED APPLICATIONS

This application claims the benefit of U.S. Provisional Application No. 62/122,413, filed Oct. 20, 2014, the disclosure of which is hereby incorporated by reference in its entirety.

GOVERNMENTAL RIGHTS

This invention was made with government support under R01 HL-089784, P01 HL-095486 and R01 HL-120867 awarded by the NIH. The government has certain rights in the invention.

FIELD OF THE INVENTION

The present disclosure relates to the field of lymphedema therapy, more specifically, to a new pharmacological strategy to rescue the failed lymph pump system that can supplement, enhance or replace current therapies.

BACKGROUND OF THE INVENTION

The lymphatic system consists of networks of interconnected capillaries, collecting vessels and lymph nodes that absorb, collect and transport the fluid and protein filtered from the blood vascular system. This system provides a critical homeostatic function: in humans, lymphatic vessels return >4 liters of fluid and a substantial amount of protein per day back into the great veins of the neck. Lymphatic vascular dysfunction results in the accumulation of excess fluid (edema) in the interstitium. Although edema is typically not life-threatening, it has serious health consequences, including pain, immobility, fibrosis, inflammation, adipose tissue accumulation, and tissue damage. Because the lymphatic system is also a critical component of immune responses, lymphedema is almost always accompanied by an increased risk of infection and other immune system problems.

Lymphedema affects over 200 million people worldwide. There is no cure for lymphedema and the usual treatment options—massage and/or external compression—only temporarily alleviate symptoms rather than address the underlying cause, which in most instances involves lymphatic tract disruption and/or compromised lymph pumping.

Therefore, there is a need to develop a new pharmacological strategy/therapy to rescue the failed lymph pump system that can supplement, enhance or replace current therapies.

SUMMARY OF THE INVENTION

In one aspect, the disclosure provides a method to improve or restore lymphatic vessel function. The method comprises administering to the lymphatic vessel a composition comprising a compound that affects the calcium channel transduction pathway.

In another aspect, the disclosure provides a method to treat or prevent lymphedema in a subject. The method comprises topically or intradermally administering to the subject a composition comprising a compound that affects the calcium channel transduction pathway.

In any of the foregoing methods, the compound that affects the calcium channel transduction pathway is selected from the group consisting of a L-type calcium channel agonist, a KATP channel inhibitor, an alpha-adrenergic agonist, and combinations thereof.

In any of the foregoing methods, the compound that affects the calcium channel transduction pathway is an alpha-adrenergic agonist.

In any of the methods, the alpha-adrenergic agonist is an α1-adrenergic agonist or an α1- and α2-adrenergic agonist.

In any of the foregoing methods, the alpha-adrenergic agonist is selected from the group consisting of phenylephrine, methoxamine, tetrahydralazine, xylometazoline, midodrine, oxymetazoline, cirazoline, metaraminol, synephrine, amidephrine, indanidine, phenylpropanolamine, norfenefrine, noradrenaline (norepinephrine), chloroethyldonidine, and etilefrine.

In any of the foregoing methods, the alpha-adrenergic agonist is selected from the group consisting of norepinephrine and phenylephrine.

In any of the foregoing methods, the compound that affects the calcium channel transduction pathway is a L-type calcium channel agonist.

In any of the foregoing methods, the L-type calcium channel agonist is selected from the group consisting of BayK8644, BayK8643, BayO8495, BayO9507, PN202-79, CGP28-392, RS30026, H160/51, YC170, FPL64176, *Goniopora* toxin, maitotoxin, atrotoxin, and palmitoyl carnitate.

In any of the foregoing methods, the L-type calcium channel agonist is selected from the group consisting of BayK8644, BayR5417, and FPL64176.

In any of the foregoing methods, the L-type calcium channel agonist is BayK8644.

In any of the foregoing methods, the compound that affects the calcium channel transduction pathway is a KATP channel inhibitor.

In any of the foregoing methods, the KATP channel inhibitor is selected from the group consisting of glyburide (glibenclamide), pinacidil, sodium 5-hydroxydecanoate, PNU-37883A (U-37883A), PNU-18177A, PNU-99963, phentolamine, alinidine, tedisamil, and ZM181,037.

In any of the foregoing methods, the KATP channel inhibitor is glyburide (glibenclamide).

In any of the foregoing methods, the composition comprises a combination of a L-type calcium channel agonist, a KATP channel inhibitor, and an alpha-adrenergic agonist.

In any of the foregoing methods, the composition comprises a L-type calcium channel agonist and a KATP channel inhibitor.

In any of the foregoing methods, the composition comprises BayK8644 and glyburide (glibenclamide).

In the method to improve or restore lymphatic vessel function, the lymphatic vessel function is improved or restored due to relief of valve lock.

In the method to treat or prevent lymphedema in a subject, the composition is topically or intradermally administered to an extremity of the subject.

In the method to treat or prevent lymphedema in a subject, the lymphedema is due to pump weakening or valve lock.

In the method to treat or prevent lymphedema in a subject, the lymphedema is secondary to obesity, congestive heart failure, hypertension, and/or peripheral vascular/venous disease.

BRIEF DESCRIPTION OF THE FIGURES

The application file contains at least one drawing executed in color. Copies of this patent application publication with color drawing(s) will be provided by the Office upon request and payment of the necessary fee.

FIG. 6A depicts that with $P_{in}$ and $P_{out}=0.5$ $cmH_2O$, $P_{out}$ is raised and $P_{sn}$ remains low across a normal valve (no back-leak). Diameter changes little on the upstream side but increases on the downstream side. FIG. 6B depicts that valves in ~50% of Foxc2$^{+/-}$ vessels leak significantly (note rise in $P_{sn}$). FIG. 6C depicts back-leak measurements at $P_{out}=10$ $cmH_2O$ in WT (C57Bl/6) and Foxc2$^{+/-}$ valves (sampled randomly). FIG. 6D depicts that a striking characteristic of Foxc2$^{+/-}$ valves is their abnormal closure vs. diameter relationship[21] in which some valves require >40 $cmH_2O$ adverse pressure to close when the vessel is expanded (the normal is 3 $cmH_2O$), suggesting the leaflets are abnormally stiff; this is likely to correlate with changes in ECM composition[54,60,66].

FIG. 7A depicts low pressure tests raising $P_{out}$ from 0.5 to 10 $cmH_2O$. FIG. 7B depicts high pressure tests raising Put to 60 $cmH_2O$. FIG. 7C depicts that some Foxc2$^{-/-}$ valves close at low pressures but reopen (arrow) as $P_{out}$ continues to rise due to back-leak. This behavior was not observed in any WT valves and likely underlies an increased susceptibility to pump failure (FIG. 5B).

FIG. 9A depicts that NE induces spontaneous contractions in a mouse popliteal vessel that did not develop any for ~40 min, even in response to a $P_{out}$ ramp. FIG. 9B depicts that a vessel with small, infrequent contractions responds to NE with consistent, large-amplitude contractions. FIG. 9C depicts that NE enhanced contractions in 13/14 vessels with impaired contractions and (FIG. 9D) induced >3.5-fold increase in FREQ (contraction frequency) and 2-fold increase in AMP (contraction amplitude) in a subset 8 vessels that had control contractions.

FIG. 11A depicts normal mesenteric valve in a WT lymphatic. FIG. 11B depicts a valve with short, stiff leaflets in a Foxc2$^{+/-}$ vessel. FIG. 11C and FIG. 11D depict abnormal valves in Foxc2$^{-/-}$ vessels after 2 and 4 wks, respectively, of tamoxifen; note the triple valve with reverse orientation in FIG. 11C (arrow) and funnel-shaped invagination through middle of valve in FIG. 11D.

FIG. 13A depicts the experimental setup. FIG. 13B depicts open and closed valves. FIG. 13C and FIG. 13D depicts valve closure in vessels of differing diameter.

DETAILED DESCRIPTION OF THE INVENTION

Figure 1A:
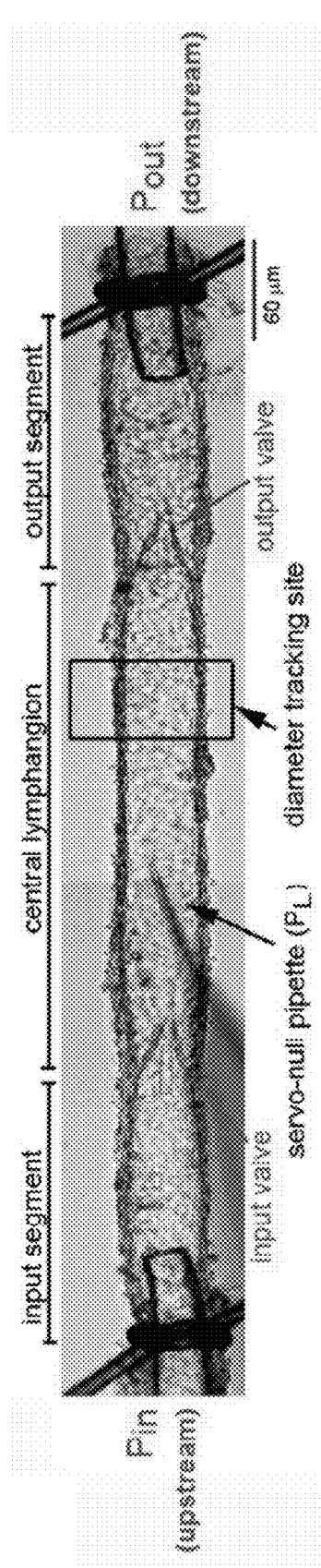
FIG. 1A and FIG. 1B depict single (FIG. 1A) and multiple (FIG. 1B) lymphangion preparations showing measurements of pressure, diameter and valve position.
Figure 1B:
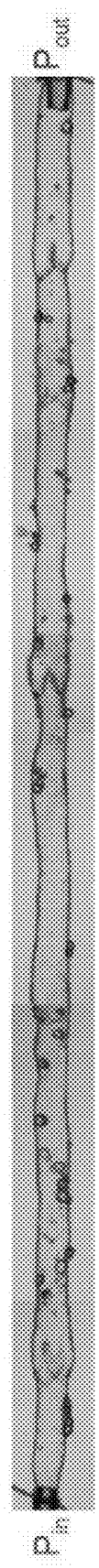
Figure 1C:
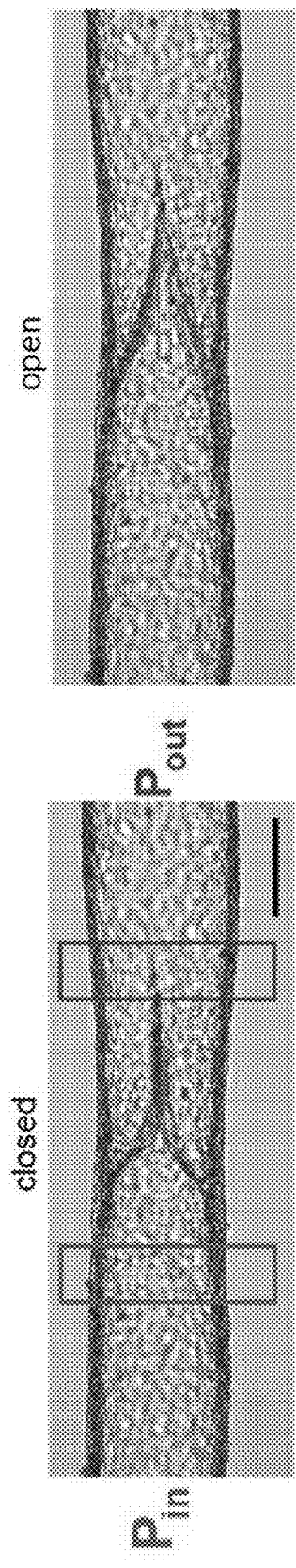
FIG. 1C and FIG. 1D depict 1-valve preparations used for valve closure (FIG. 1C) and back-leak (FIG. 1D) tests. Color coding applies to pressure, diameter & valve traces shown in all subsequent figures; blue=upstream. black=mid segment, red=downstream. $P_{in}$ and $P_{out}$ are controlled with a computer-based servo controller; $P_L$ is intraluminal pressure measured with a servo-null micropipette inserted through the wall; diameters are measured with computer-based edge detection[15]; valve positions are determined using densitometry windows as shown[21,22,69,71].
Figure 1D:
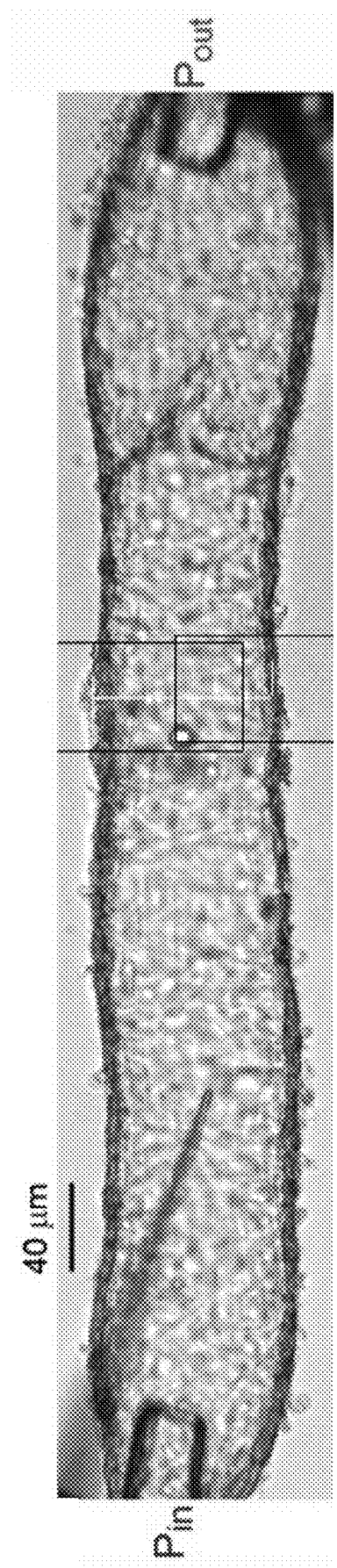

Central lymph movement relies critically on the intrinsic spontaneous contractions of lymphatic muscle cells, which constitute a "lymphatic pump", working in conjunction with one-way valves to prevent backward transmission of pressure. Although passive compression of lymphatic vessels by external tissues (e.g. skeletal muscle) can aid lymph movement, the active contractions of lymphatic muscle cells account for ~⅔ of lymph transport in human dependent extremities. In lymphedema, lymphatic diastolic pressure is elevated, vessel diameter is enlarged, contraction amplitude is impaired, and the valves are apparently insufficient thereby pointing to failure of the lymphatic pump in response to an abnormally high pressure load that is exacerbated by gravitational forces. The inventors have discovered that pump dysfunction can be reversed by regulating the calcium channel transduction pathway. Accordingly, the disclosure provides a novel pharmacologic method to improve/restore lymphatic vessel function in a subject. The method comprises local administration of a composition comprising a compound that affects the calcium channel transduction pathway to a subject's skin near an extremity exhibiting lymphedema.

I. Composition

In an aspect, a composition of the invention comprises a compound that affects the calcium channel transduction pathway. Calcium ions are important for cellular signaling, as once they enter the cytoplasm they exert allosteric regulatory effects on many enzymes and proteins. Calcium can act in signal transduction resulting from activation of ion channels or as a second messenger caused by indirect signal transduction pathways such as G protein-coupled receptors. Movement of calcium ions from the extracellular compartment to the intracellular compartment alters membrane potential. Calcium signaling is involved in muscle contraction, neuronal transmission, cellular motility, fertilization, cell growth or proliferation, learning and memory, secretion, regulation of enzyme activity, permeability of ion channels, activity of ion pumps, and components of the cytoskeleton. A compound that affects the calcium channel transduction pathway is a compound that facilitates calcium influx. In a specific embodiment, a compound that affects the calcium channel transduction pathway is selected from the group consisting of a L-type calcium channel agonist, a KATP channel inhibitor, an alpha-adrenergic agonist, and combinations thereof.

In one embodiment, a composition of the invention comprises an alpha ($\alpha$) adrenergic agonist. An adrenergic agonist is a drug that stimulates a response from the adrenergic receptors. The five main categories of adrenergic receptors are: $\alpha 1$, $\alpha 2$, $\beta 1$, $\beta 2$, and $\beta 3$. However, in general, the receptors are broadly grouped into $\alpha$ and $\beta$ receptors. The two subclasses of $\alpha$-receptor, $\alpha 1$ and $\alpha 2$, are further subdivided into $\alpha 1A$, $\alpha 1B$, $\alpha 1D$, $\alpha 2A$, $\alpha 2B$ and $\alpha 2C$. The $\alpha 1$ and $\alpha 2$ adrenergic receptors are both involved in smooth muscle contraction and function in vasoconstriction. The $\alpha 1$ adrenergic receptor activates phospholipase C which results in a rise in calcium in the cell. The $\alpha 2$ adrenergic receptor inactivates adenylate cyclase which results in a decrease in cAMP. In an embodiment, the alpha-adrenergic agonist is an $\alpha 1$-adrenergic agonist, an $\alpha 2$-adrenergic agonist or an $\alpha 1$- and $\alpha 2$-adrenergic agonist. In a specific embodiment, the alpha-adrenergic agonist is an $\alpha 1$-adrenergic agonist or an $\alpha 1$- and $\alpha 2$-adrenergic agonist. Importantly, the alpha-adrenergic agonist is a selective alpha-adrenergic agonist (i.e. the alpha-adrenergic agonist specifically binds to the alpha-adrenergic receptor, but does not specifically bind to the beta-adrenergic receptor). Stated another way, the alpha-adrenergic agonist acts on a single receptor only (i.e. it does not act on the $\beta$-adrenergic receptor). A skilled artisan would be able to determine if a compound is a selective alpha-adrenergic agonist. For example, binding affinity assays may be used to determine the affinity of a compound for $\alpha$- and $\beta$-adrenergic receptors. The phrase "specifically binds" herein means ligands bind to the target protein with an affinity ($K_d$) in the range of at least 0.1 mM to 1 pM, or in the range of at least 0.1 pM to 200 nM, or in the range of at least 0.1 pM to 10 nM. Non-limiting examples of selective $\alpha 1$-adrenergic agonists include phenylephrine, methoxamine, tetrahydralazine, xylometazoline, midodrine, oxymetazoline, cirazoline, metaraminol, synephrine, amidephrine, indanidine, phenylpropanolamine, norfenefrine. Non-limiting examples of selective $\alpha 2$-adrenergic agonists include $\alpha$-methyldopa, donidine, agmatine, dexmedetomidine, medetomidine, romifidine, brimonidine, detomidine, lofexidine, xylazine, tizanidine, guanfacine, amitraz, methylnorepinephrine, guanabenz, guanoxabenz, fadolmidine, talipexole, apradonidine, mivazerol, guanethidine, ergotamine. Non-limiting examples of selective $\alpha 1$- and $\alpha 2$-adrenergic agonists include noradrenaline (norepinephrine), chloroethyldonidine, etilefrine. In certain embodiments, the alpha-adrenergic agonist is selected from the group consisting of phenylephrine, methoxamine, tetrahydralazine, xylometazoline, midodrine, oxymetazoline, cirazoline, metaraminol, synephrine, amidephrine, indanidine, phenylpropanolamine, norfenefrine, noradrenaline (norepinephrine), chloroethyldonidine, and etilefrine. In a specific embodiment, the alpha-adrenergic agonist is selected from the group consisting of norepinephrine and phenylephrine.

In another embodiment, a composition of the invention comprises a vasoconstrictor. Vasoconstriction is the narrowing of the blood vessels resulting from contraction of the muscular wall of the vessels, in particular the large arteries and small arterioles. The mechanism that leads to vasoconstriction results from the increased concentration of calcium ($Ca^{2+}$ ions) within vascular smooth muscle cells. There are two general functional classes of vasoconstrictors based on their mechanism of action. The first class is sympathomimetic drugs that have alpha-adrenoceptor agonist (a-agonist) properties. A common property of several of these drugs is that they bind to $\alpha 1$-adrenoceptors on vascular smooth muscle thereby promoting smooth muscle contraction. A second class of vasoconstrictor (non-sympathomimetic) is vasopressin analogs. In an embodiment, a vasoconstrictor of the composition is a vasoconstrictor from the class of sympathomimetic drugs. In another embodiment, a vasoconstrictor of the composition is a compound that increases the concentration of calcium in a cell. Non-limiting examples of vasoconstrictors include 251-NBOMe, amphetamines, AMT, antihistamines, caffeine, cocaine, DOM, LSA, methylphenidate, mephedrone, oxymetazoline, phenylephrine, propylhexedrine, pseudoephedrine, stimulants, tetrahydrozoline hydrochloride.

In a certain embodiment, a composition of the invention comprises L-type calcium channel agonist. The L-type calcium channel (also referred to as the dihydropyridine channel, or DHP channel) is part of the high-voltage activated family of voltage-dependent calcium channel. Members of the family of voltage-dependent calcium channels include N-type, L-type, and T-type voltage-dependent calcium channels. Only L-type calcium channel agonists are suitable for a composition of the invention. "L" stands for long-lasting referring to the length of activation. L-type calcium channels are responsible for excitation-contraction coupling of skeletal, smooth, cardiac muscle. The L class of voltage-dependent $Ca^{2+}$ channels provides an important pathway for $Ca^{2+}$ entry into a variety of excitable cells. The best characterized of these are certain 1,4-dihydropyridines, typified by BayK8644, but also include BayK8643, BayO8495, BayO9507, PN202-79, CGP28-392, RS30026, H160/51, YC170, which act as agonists of the channel. The benzoylpyrrole group of molecules, which includes FPL64176, have proven to be highly efficacious L channel agonists. Certain naturally occurring substances, ranging from toxins to endogenous ligands, such as *Goniopora* toxin, maitotoxin, atrotoxin, and palmitoyl carnitate, have also been proposed as activators of this channel. For example, see Rampe and Kane, *Drug Development Research* 1994; 33(3): 344-363, the disclosure of which is hereby incorporated by reference in its entirety. In an embodiment, a L-type calcium channel agonist is a compound that facilitates $Ca^{2+}$ influx through L-type calcium channels. In an embodiment, a L-type calcium channel agonist is selected from the group consisting of BayK8644, BayK8643, BayO8495, BayO9507, PN202-79, CGP28-392, RS30026, H160/51, YC170, FPL64176, *Goniopora* toxin, maitotoxin, atrotoxin, and palmitoyl carnitate. In certain embodiments, a L-type calcium channel agonist is selected from the group consisting of BayK8644, BayR5417, and FPL64176. In a specific embodiment, the L-type calcium channel agonist is BayK8644.

In another embodiment, a composition of the invention comprises a KATP channel inhibitor. A KATP channel, also referred to as an ATP-sensitive potassium channel, is a type of potassium channel that is gated by intracellular nucleotides, ATP and ADP. Closure of KATP channels depolarizes the plasma membrane, thereby triggering calcium influx. KATP channel activity influences cell $Ca^{2+}$ homeostasis by regulating $Ca^{2+}$ influx through L-type calcium channels. In an embodiment, a KATP channel inhibitor is a compound that blocks KATP channels thereby triggering calcium influx. Non-limiting examples of KATP channel inhibitors include glyburide (glibendamide), pinacidil, sodium 5-hydroxydecanoate, PNU-37883A (U-37883A), PNU-18177A, PNU-99963, phentolamine, alinidine, tedisamil, and ZM181,037. For example, see Humphrey, *Cardiovascular Drug Reviews* 1999; 17(4): 295-328, the disclosure of which is hereby incorporated by reference in its entirety. In certain embodiments, a KATP channel inhibitor is selected from the group consisting of glyburide (glibendamide), pinacidil, sodium 5-hydroxydecanoate, PNU-37883A (U-37883A), PNU-18177A, PNU-99963, phentolamine, alinidine, tedisamil, and ZM181,037. In a specific embodiment, the KATP channel inhibitor is glyburide (glibendamide).

In other embodiments, a composition of the invention comprises a combination of a L-type calcium channel agonist, a KATP channel inhibitor, and an alpha-adrenergic agonist. For example, a composition of the invention may comprise a L-type calcium channel agonist and a KATP channel inhibitor. In another embodiment, a composition of the invention may comprise a L-type calcium channel agonist and an alpha-adrenergic agonist. In still another embodiment, a composition of the invention may comprise a KATP channel inhibitor and an alpha-adrenergic agonist. In yet another embodiment, a composition of the invention may comprise a L-type calcium channel agonist, a KATP channel inhibitor, and an alpha-adrenergic agonist. In a specific embodiment, a composition of the invention may comprise a L-type calcium channel agonist and a KATP channel inhibitor. In an exemplary embodiment, a composition of the invention comprises BayK8644 and glyburide (glibendamide).

(a) Components of the Composition

The disclosure also provides pharmaceutical compositions. The pharmaceutical composition comprises a compound that affects the calcium channel transduction pathway, as the active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, or a coloring agent. The amount and types of excipients utilized to form pharmaceutical compositions may be selected according to known principles of pharmaceutical science.

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

In various embodiments, the excipient may be a pH modifier. By way of non-limiting example, the pH modifying agent may be sodium carbonate, sodium bicarbonate, sodium citrate, citric acid, or phosphoric acid.

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, days, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

In a further embodiment, the excipient may be a lubricant. Non-limiting examples of suitable lubricants include minerals such as talc or silica; and fats such as vegetable stearin, magnesium stearate or stearic acid.

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The composition can be formulated into various dosage forms and administered topically or intradermally by a number of different means that will deliver a therapeutically effective amount of the active ingredient. Such compositions administered topically or intradermally in dosage unit formulations may contain conventional nontoxic pharmaceutically acceptable carriers, adjuvants, and vehicles as desired. Topical administration may also involve the use of transdermal administration such as transdermal patches or iontophoresis devices. Formulation of drugs is discussed in, for example, Gennaro, A. R., Remington's Pharmaceutical Sciences, Mack Publishing Co., Easton, Pa. (18$^{th}$ ed, 1995), and Liberman, H. A. and Lachman, L., Eds., Pharmaceutical Dosage Forms, Marcel Dekker Inc., New York, N.Y. (1980).

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising a compound that affects the calcium channel transduction pathway is encapsulated in a suitable vehicle to either aid in the delivery of the compound, to increase the stability of the composition, or to minimize potential toxicity of the composition. As will be appreciated by a skilled artisan, a variety of vehicles are suitable for delivering a composition of the disclosure. Non-limiting examples of suitable structured fluid delivery systems may include nanoparticles, liposomes, microemulsions, micelles, dendrimers and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of a compound that affects the calcium channel transduction pathway in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, a compound that affects the calcium channel transduction pathway may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholids include phosphatidic acid (PA), phosphatidylserine (PS), phosphatidylinositol (PI), phosphatidylglycerol (PG), diphosphatidylglycerol (DPG), phosphatidylcholine (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (common name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9,12,15-octadecatrienoate (linolenate), and all cis-5,8,11,14-eicosatetraenoate (arachidonate). The two fatty acid chains of a phospholipid may be identical or different. Acceptable phospholipids include dioleoyl PS, dioleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocyanine perchloarate, 1,1'-dioleyl-3,3,3',3'-tetramethylindo carbocyanine methanesulfonate, N-4-(delinoleylaminostyryl)-N-methylpyridinium iodide, or 1,1-dilinoleyl-3,3,3',3'-tetramethylindocarbocyanine perchloarate.

Liposomes may optionally comprise sphingolipids, in which sphingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyethylene glycol (PEG). PEGs may range in size from about 500 to about 10,000 daltons.

Liposomes may further comprise a suitable solvent. The solvent may be an organic solvent or an inorganic solvent. Suitable solvents include, but are not limited to, dimethylsulfoxide (DMSO), methylpyrrolidone, N-methylpyrrolidone, acetronitrile, alcohols, dimethylformamide, tetrahydrofuran, or combinations thereof.

Liposomes carrying a compound that affects the calcium channel transduction pathway may be prepared by any known method of preparing liposomes for drug delivery, such as, for example, detailed in U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference in their entirety. For example, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of methionine compound, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatterers of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and reverse micelles are like drops of water in oil. In an alternative embodiment, the microemulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. The compound that affects the calcium channel transduction pathway may be encapsulated in a microemulsion by any method generally known in the art.

In yet another embodiment, a compound that affects the calcium channel transduction pathway may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

II. Methods

In an aspect, the disclosure provides a method of relieving valve lock of a lymphatic vessel. The method comprises administering to the lymphatic vessel a composition comprising a compound that affects the calcium channel transduction pathway. As used herein, the term "valve lock" is used to describe a valve of a lymphatic vessel that has been locked open. A lymphatic vessel experiencing valve lock cannot pump, despite continued contractions. Accordingly, valve lock results in catastrophic pump failure. Relieving valve lock with a composition of the invention improves lymphatic valve function. Accordingly, a method of relieving valve lock of a lymphatic vessel may also improve or restore lymph pump function. As such, administering to a lymphatic vessel experiencing valve lock a composition comprising a compound that affects the calcium channel transduction pathway relieves or reverses valve lock thereby improving or restoring pump function. Relief of valve lock may be measured by determining diameter, pressure and/or valve position in a lymphatic vessel as described in the Examples.

In another aspect, the disclosure provides a method to improve or restore lymphatic vessel function. The method comprises administering to the lymphatic vessel a composition comprising a compound that affects the calcium channel transduction pathway. The composition may improve or restore lymphatic vessel function by relieving valve lock. Methods of measuring improvement or restoration of lymphatic vessel function are known in the art. For example, vessel diameter, vessel pressure and/or valve position may be measured. Alternatively, if the vessel is disposed in a subject, swelling, range of motion, subject's discomfort, and/or fibrosis may be evaluated. Still further, lymphoscintography, MRI, CT, and/or Doppler ultrasound may be performed.

In still another aspect, the disclosure provides a method to treat or prevent lymphedema in a subject. The method comprises topically or intradermally administering to the subject a composition comprising a compound that affects the calcium channel transduction pathway. The composition may be topically or intradermally administered to a region exhibiting signs or symptoms of lymphedema. Alternatively, the composition may be topically or intradermally administered to a region suspected of exhibiting signs or symptoms of lymphedema. The region may be an extremity such as an arm and/or leg. A subject suspected of exhibiting signs or symptoms of lymphedema may be a subject at risk for developing lymphedema. Non-limiting examples of risk factors include cancer, cancer treatment, older age, excess weight or obesity and/or rheumatoid or psoriatic arthritis. By "treat or prevent" is meant causing a reduction in the swelling of an extremity, slowing or preventing an increase in the swelling of an extremity, increasing the duration of time between the disappearance of swelling in an extremity and its reappearance, preventing an initial or subsequent occurrence of swelling in an extremity, or reducing an adverse symptom associated with swelling in an extremity. As used herein, "lymphedema" refers to swelling, generally occurring in the extremities, due to buildup of lymph fluid. Non-limiting causes of buildup include removal of or damage to lymph nodes, blockage in the lymphatic system, pump weakening and/or valve lock. In certain embodiments, lymphedema is due to pump weakening or valve lock. In a specific embodiment, lymphedema is due to valve lock. Non-limiting examples of signs and symptoms of lymphedema include swelling of part or all of a subject's arm or leg, including fingers or toes, a feeling of heaviness or tightness, restricted range of motion, aching or discomfort, recurring infections, and hardening and thickening of the skin (fibrosis). Swelling caused by lymphedema may range from mild, hardly noticeable changes in the size of a subject's arm or leg to extreme changes that make the limb hard to use. Lymphedema may be primary lymphedema or secondary lymphedema. Non-limiting examples of causes of primary lymphedema include Milroy's disease (congenital lymphedema), lymphedema distichiasis, Meige's disease (lymphedema praecox) and late-onset lymphedema (lymphedema tarde). Non-limiting examples of causes of secondary lymphedema may include surgery to remove lymph nodes, radiation treatment, cancer, infection, obesity, congestive heart failure, hypertension, and peripheral vascular/venous disease. In a method of the disclosure, lymphedema is secondary to obesity, congestive heart failure, hypertension, and/or peripheral vascular/venous disease. In another method of the disclosure, lymphedema is not due to lymph node removal or lymphatic tract disruption as a by-product of surgery.

A method to treat or prevent lymphedema comprising topically or intradermally administering to a subject a composition comprising a compound that affects the calcium channel transduction pathway may further comprise methods standard in the art for the treatment of lymphedema. For example, topically or intradermally administering a composition of the invention may be used in combination with exercises, wrapping of the arm or leg, massage, pneumatic compression, compression garments and/or complete decongestive therapy (CDT).

In still yet another aspect, the disclosure provides a method to treat lymphatic dysfunction in a subject. The method comprises topically or intradermally applying to the subject a composition comprising a compound that affects the calcium channel transduction pathway. Lymphatic dysfunction is due to less effective functioning of the lymphatic pump mechanism. Lymphatic dysfunction may lead to fluid accumulation in the tissue. Lymphatic dysfunction may be present in subjects with chronic muscle pain (myalgia), chronic inflammatory conditions (tendonitis, bursitis), chronic sinusitis, migraine headaches, tinnitus, Lyme disease, fibromyalgia, and/or chronic fatigue syndrome.

The composition is described in Section I, the administration and subject are described below.

(a) Administration

In certain aspects, a therapeutically effective amount of a composition of the invention may be administered to a subject. Administration is performed using standard effective techniques. In a preferred embodiment, a composition is administered topically or intradermally. A composition of the invention may be administered topically as an ointment, cream, suspension, lotion, powder, solution, paste, gel, spray, aerosol, salve, patch or oil. Additionally, a composition of the invention may be administered intradermally as an injection. In some embodiments, a composition of the invention is administered as a topical ointment or cream. In other embodiments, a composition of the invention is administered as an adhesive gauze. In still other embodiments, a composition of the invention is administered as a salve.

For therapeutic applications, a therapeutically effective amount of a composition of the invention is administered to a subject. A "therapeutically effective amount" is an amount of the therapeutic composition sufficient to produce a measurable response (e.g., relief of valve lock, reduction in swelling, reduction in feeling of heaviness or tightness, improvement in range of motion, reduction in aching and/or discomfort, reduction in number of recurrent infections and reduction in fibrosis). Actual dosage levels of active ingredients in a therapeutic composition of the invention can be varied so as to administer an amount of the active compound(s) that is effective to achieve the desired therapeutic response for a particular subject. The selected dosage level will depend upon a variety of factors including the activity of the therapeutic composition, formulation, the route of administration, combination with other drugs or treatments, age, the lymphedema, the symptoms, and the physical condition and prior medical history of the subject being treated. In some embodiments, a minimal dose is administered, and dose is escalated in the absence of dose-limiting toxicity. Determination and adjustment of a therapeutically effective dose, as well as evaluation of when and how to make such adjustments, are known to those of ordinary skill in the art of medicine. In certain embodiments, a compound that affects the calcium channel transduction pathway may be administered at such a dose that about 1 nM to about 1 mM is administered to the lymphatic vessel. For example, the calcium channel transduction pathway may be administered at such a dose that about 10 nM to about 100 µM, or about 10 nM to about 500 nM, or about 10 nM to about 300 nM, or about 100 nM to about 100 µM, or about 100 nM to about 10 µM is administered to the lymphatic vessel. In an embodiment, when the compound that affects the calcium channel transduction pathway is an alpha-adrenergic agonist, the alpha-adrenergic agonist may be administered at such a dose that about 10 nM to about 100 µM, or about 10 nM to about 500 nM, or about 10 nM to about 300 nM, or about 100 nM to about 300 nM, or about 100 nM to about 1 µM is administered to the lymphatic vessel. In a specific embodiment, norepinephrine or phenylepinephrine is administered at such a dose that about 10 nM to about 300 nM is administered to the lymphatic vessel. In another embodiment, when the compound that affects the calcium channel transduction pathway is a L-type calcium channel agonist, the L-type calcium channel agonist may be administered at such a dose that about 10 nM to about 100 µM, or about 10 nM to about 500 nM, or about 10 nM to about 300 nM, or about 100 nM to about 300 nM, or about 100 nM to about 1 µM is administered to the lymphatic vessel. In a specific embodiment, BayK8644 is administered at such a dose that about 10 nM to about 300 nM is administered to the lymphatic vessel. In still another embodiment, when the compound that affects the calcium channel transduction pathway is a KATP channel inhibitor, the KATP channel inhibitor may be administered at such a dose that about 10 nM to about 100 µM, or about 10 nM to about 10 µM, or about 100 nM to about 10 µM, or about 100 nM to about 100 µM, or about 100 nM to about 1 µM is administered to the lymphatic vessel. In a specific embodiment, glyburide (glibenclamide) is administered at such a dose that about 100 nM to about 10 µM is administered to the lymphatic vessel.

The timing of administration of the treatment relative to the disease itself and duration of treatment will be determined by the circumstances surrounding the case. Treatment could begin in a hospital or clinic itself, or at a later time after discharge from the hospital or after being seen in an outpatient clinic.

Duration of treatment could range from a single dose administered on a one-time basis to a life-long course of therapeutic treatments. The duration of treatment can and will vary depending on the subject and the disease or disorder to be treated. For example, the duration of treatment may be for 1 day, 2 days, 3 days, 4 days, 5 days, 6 days, or 7 days. Or, the duration of treatment may be for 1 week, 2 weeks, 3 weeks, 4 weeks, 5 weeks or 6 weeks. Alternatively, the duration of treatment may be for 1 month, 2 months, 3 months, 4 months, 5 months, 6 months, 7 months, 8 months, 9 months, 10 months, 11 months, 12 months. In still another embodiment, the duration of treatment may be for 1 year, 2 years, 3 years, 4 years, 5 years, or greater than 5 years. It is also contemplated that administration may be frequent for a period of time and then administration may be spaced out for a period of time. For example, duration of treatment may be 5 days, then no treatment for 9 days, then treatment for 5 days.

The frequency of dosing may be once, twice, three times or more daily or once, twice, three times or more per week or per month, or as needed as to effectively treat the symptoms or disease. In certain embodiments, the frequency of dosing may be once, twice or three times daily. For example, a dose may be administered every 24 hours, every 12 hours, or every 8 hours. In other embodiments, the frequency of dosing may be once, twice or three times weekly. For example, a dose may be administered every 2 days, every 3 days or every 4 days. In a different embodiment, the frequency of dosing may be one, twice, three or four times monthly. For example, a dose may be administered every 1 week, every 2 weeks, every 3 weeks or every 4 weeks.

(b) Subject

A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

The human subject may be of any age. However, since lymphedema may be associated with aging, a human subject may be an older human subject. In some embodiments, the human subject may be about 20, 25, 30, 40, 45, 50, 55, 60, 65, 70, 75, 80, 85, 90, 95 years of age or older. In some preferred embodiments, the human subject is 30 years of age or older. In other preferred embodiments, the human subject is 40 years of age or older. In other preferred embodiments, the human subject is 45 years of age or older. In yet other preferred embodiments, the human subject is 50 years of age or older. In still other preferred embodiments, the human subject is 55 years of age or older. In other preferred embodiments, the human subject is 60 years of age or older. In yet other preferred embodiments, the human subject is 65 years of age or older. In still other preferred embodiments, the human subject is 70 years of age or older. In other preferred embodiments, the human subject is 75 years of age or older. In still other preferred embodiments, the human subject is 80 years of age or older. In yet other preferred embodiments, the human subject is 85 years of age or older. In still other preferred embodiments, the human subject is 90 years of age or older.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1. Lymphatic Valve Formation, Operation, Dysfunction

Methods to isolate and cannulate small lymphatic vessels from rat[31] and mouse[69] were previously developed and described in detail in the literature, as are methods for gradual and rapid pressure control during measurements of contractile function[22,72]. The various configurations used are shown in FIG. 1.

Figure 2A:
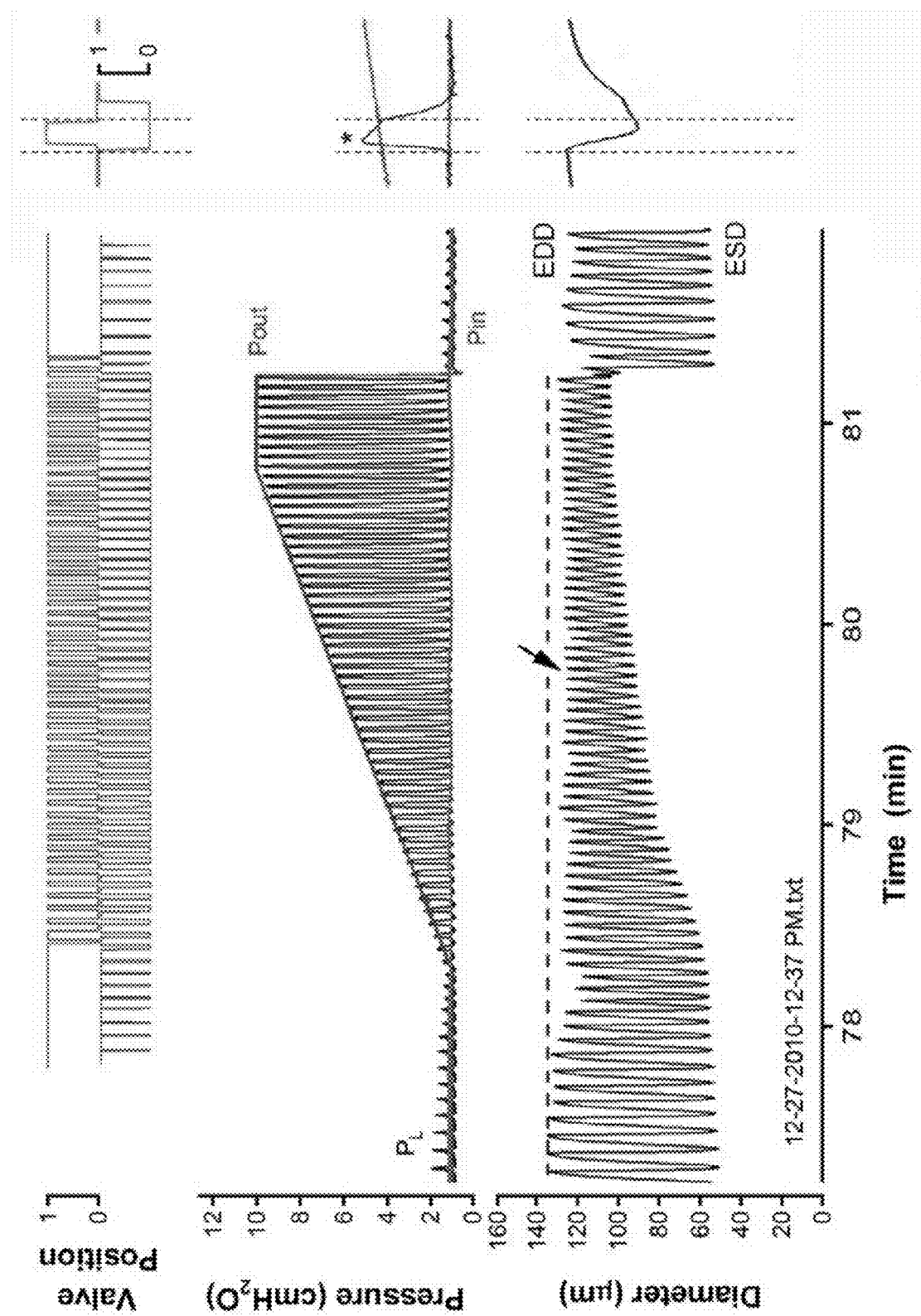
FIG. 2A depicts normal pumping of a 2-valve lymphangion when output pressure is slowly elevated to 10 $cmH_2O$ with preload set at an optimal level (1-3 $cmH_2O$)[72]. Insert shows a single pump cycle on an expanded time scale[21,22]. Valves: 1=open; 0=closed.
Figure 2B:
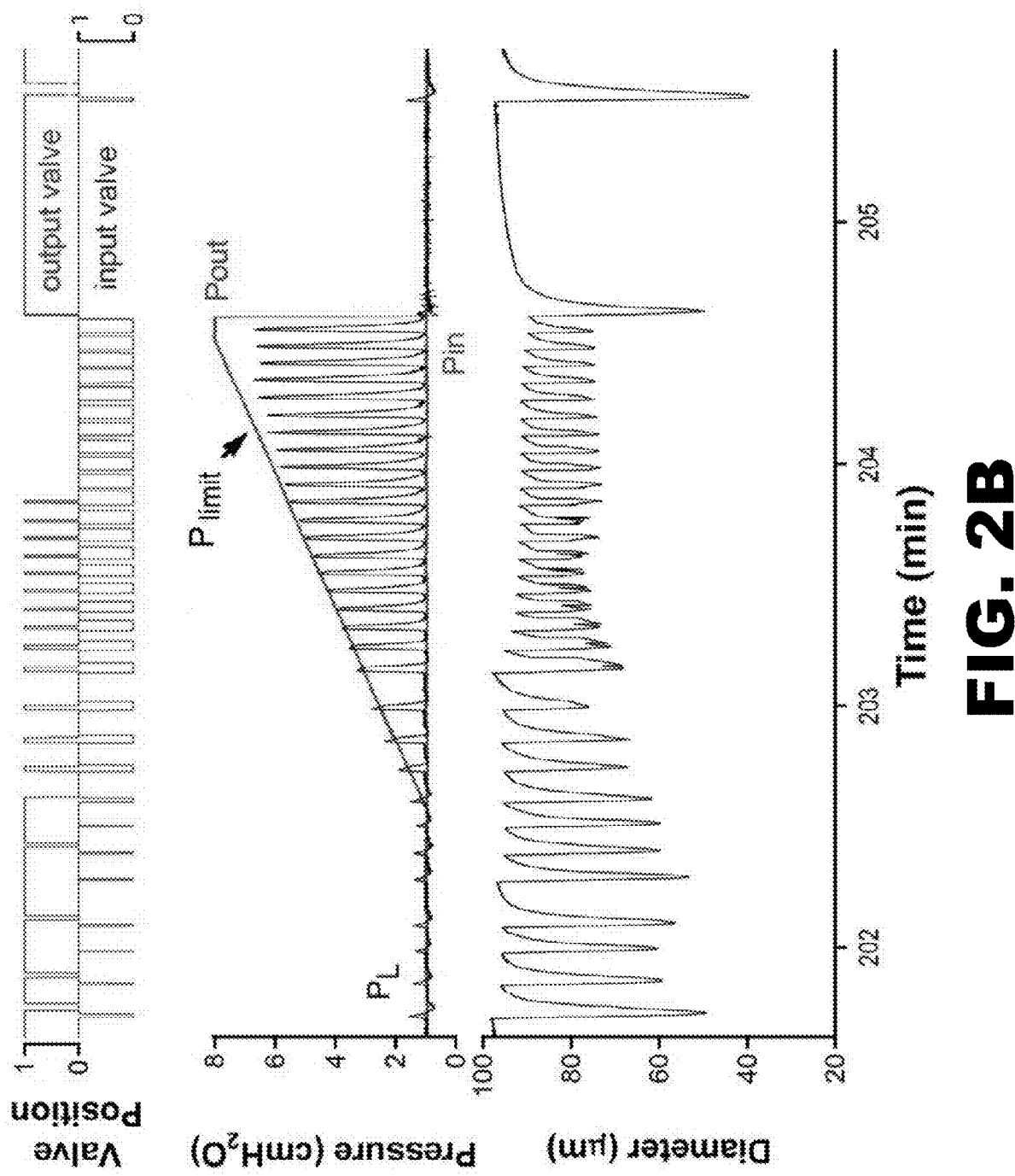
FIG. 2B depicts the "classical" type of pump failure presumed in the literature to occur[25,52,55,76], but which has not been directly observed previously: the vessel simply fails to eject when output pressure exceeds the capacity of the pump—as evident by a closed output valve (top trace, red).
Figure 2C:
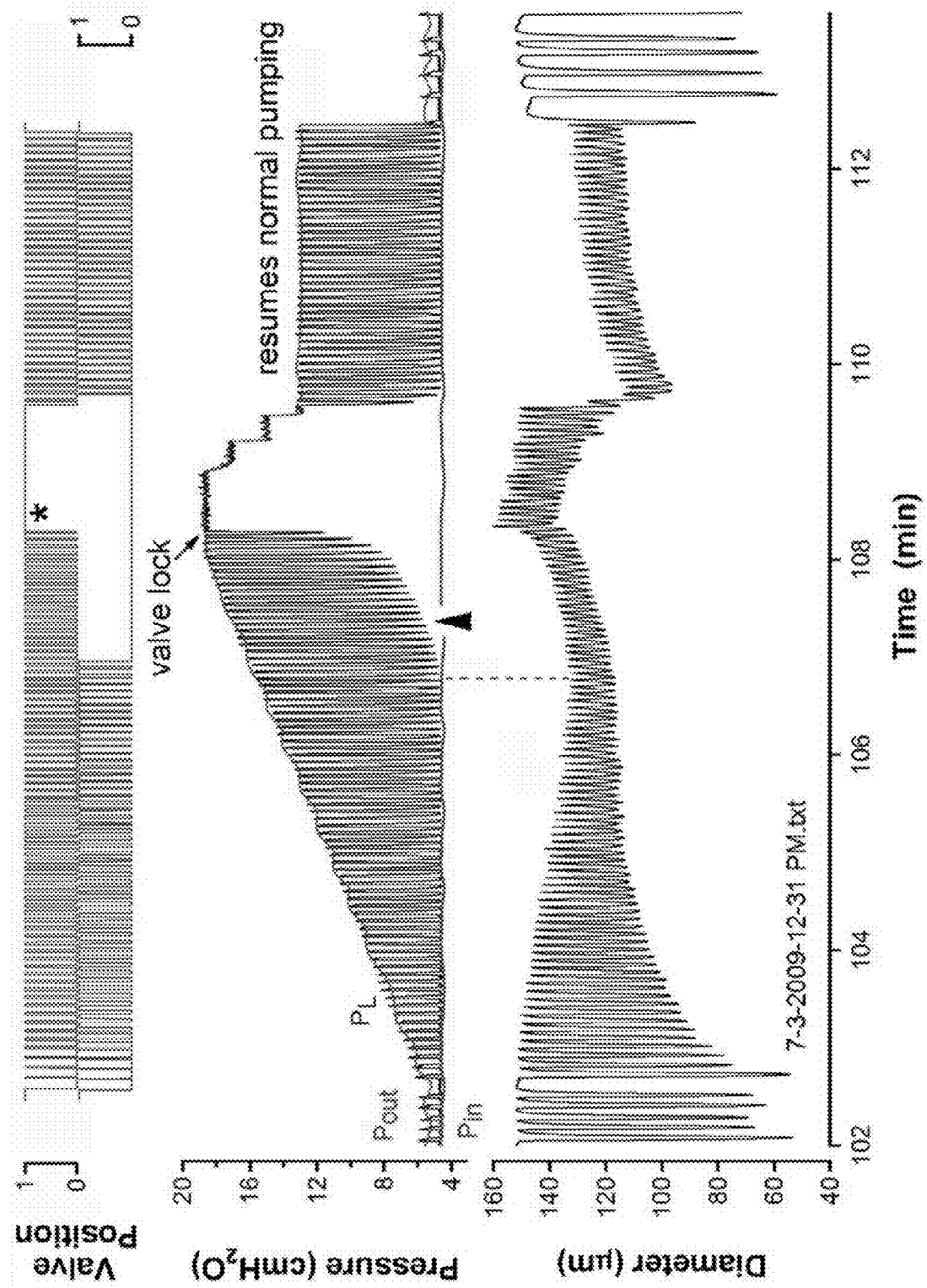
FIG. 2C depicts a different type of pump failure, valve lock, occurs in ~50% of cases upon output pressure elevation: the output valve locks open in systole as pressures equilibrate across it and pumping stops. All three examples are representative of responses in both rats and mice.

Studies were made of single and multiple lymphangions from mice under hydrostatic conditions simulating those experienced in primary and secondary lymphedema. When a progressive rise in outflow pressure is imposed, simulating the pressure load on the vessel in a dependent extremity, the normal response of the vessel is a myogenic constriction to $P_{out}$ elevation (arrow, described in detail in ref.[71]) with continued pumping, such that internal pressure generation slightly exceeds $P_{out}$ during systole of each contraction cycle (*); as a result the output valve opens briefly in systole, allowing partial ejection. When higher levels of $P_{out}$ are imposed (i.e. output pressure overload), two types of pump failure occur even in healthy vessels. In the first type, the pump gradually weakens until it cannot eject, at which point internal pressure development becomes insufficient to open the output valve (FIG. 2B). When the pump limit is reached, contractions continue but the developed pressure does not exceed $P_{out}$ ("$P_{limit}$", arrow) and the output valve remains closed (top red trace). The input valve continues to gate each contraction cycle, allowing lumenal pressure ($P_L$) to equilibrate with $P_{in}$ in diastole. $P_{limit}$ averages 12.1 cmH$_2$O in rat[22] and ~14 cmH$_2$O in mouse. However, this is only one mode of failure when afterload exceeds pump capacity: another type of pump failure was recently discovered, occurring ~30% of the time, that has not been previously recognized (FIG. 2C). The pump can eject at high $P_{out}$ levels, but as the vessel loses myogenic tone (dotted vertical line), a gradual rise in diastolic pressure occurs (black arrowhead) until pressure suddenly equilibrates across the output valve during systole, giving it the appearance of "locking open" (*). Despite continued contractions, the vessel cannot pump. This catastrophic pump failure, termed "valve lock" is reversible only if $P_{out}$ is lowered (with the exception shown in FIG. 3C).

Figure 3A:
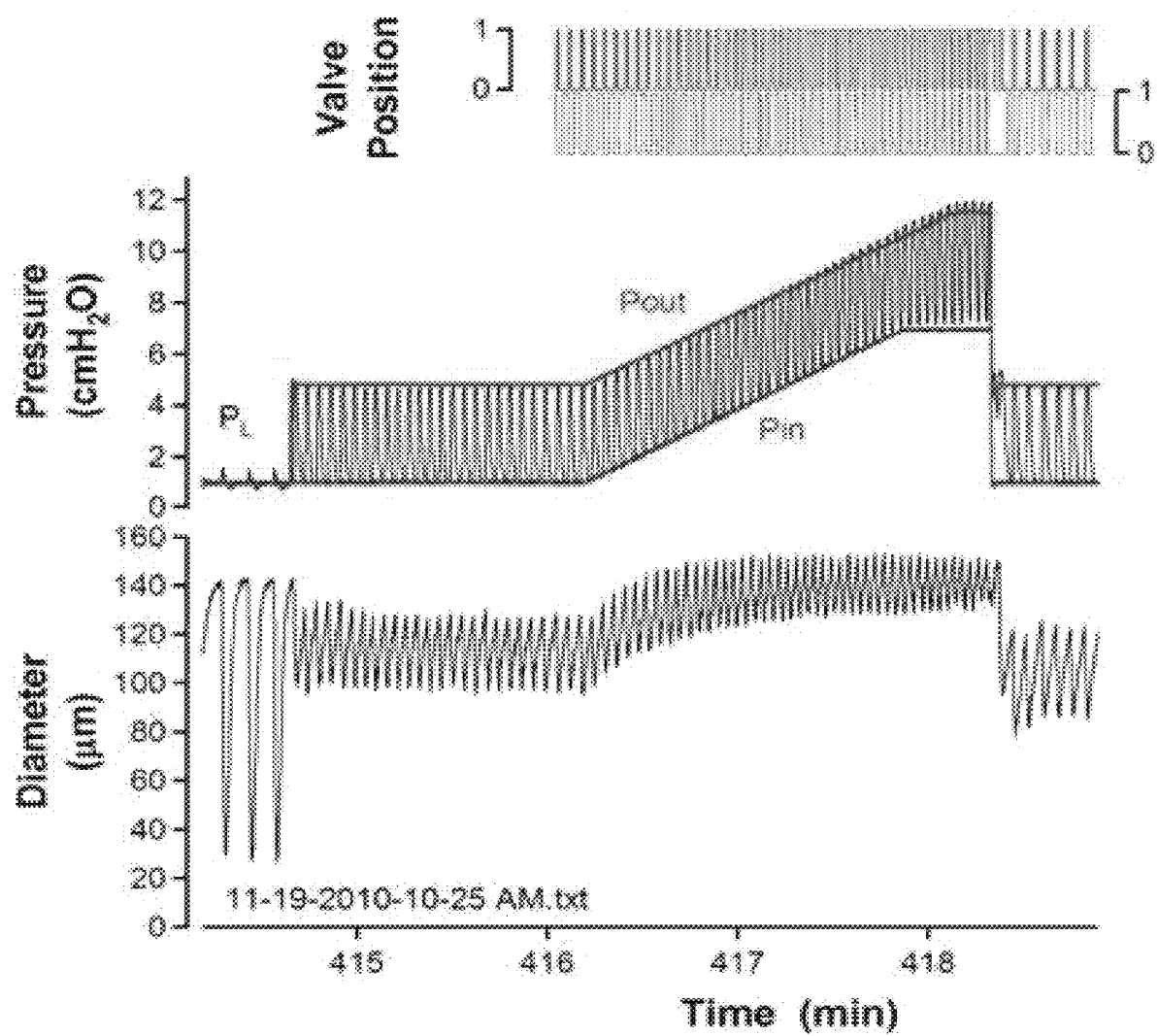
FIG. 3A depicts the response of a healthy lymphangion to a parallel pressure ramp: both valves gate normally and the pump functions over a wide pressure range.
Figure 3B:
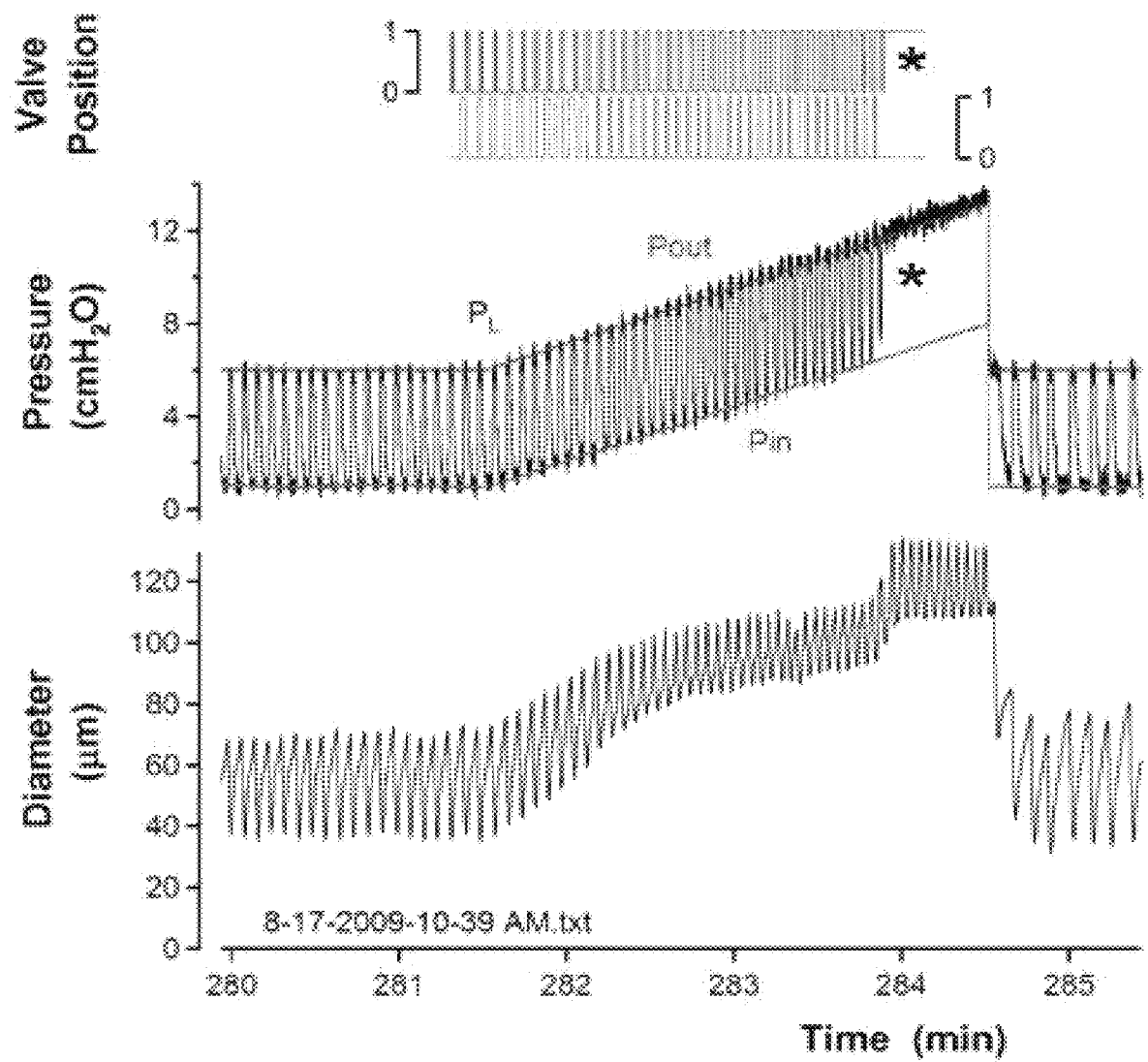
FIG. 3B depicts the instantaneous pump failure due to valve lock (*) in a healthy lymphangion.
Figure 3C:
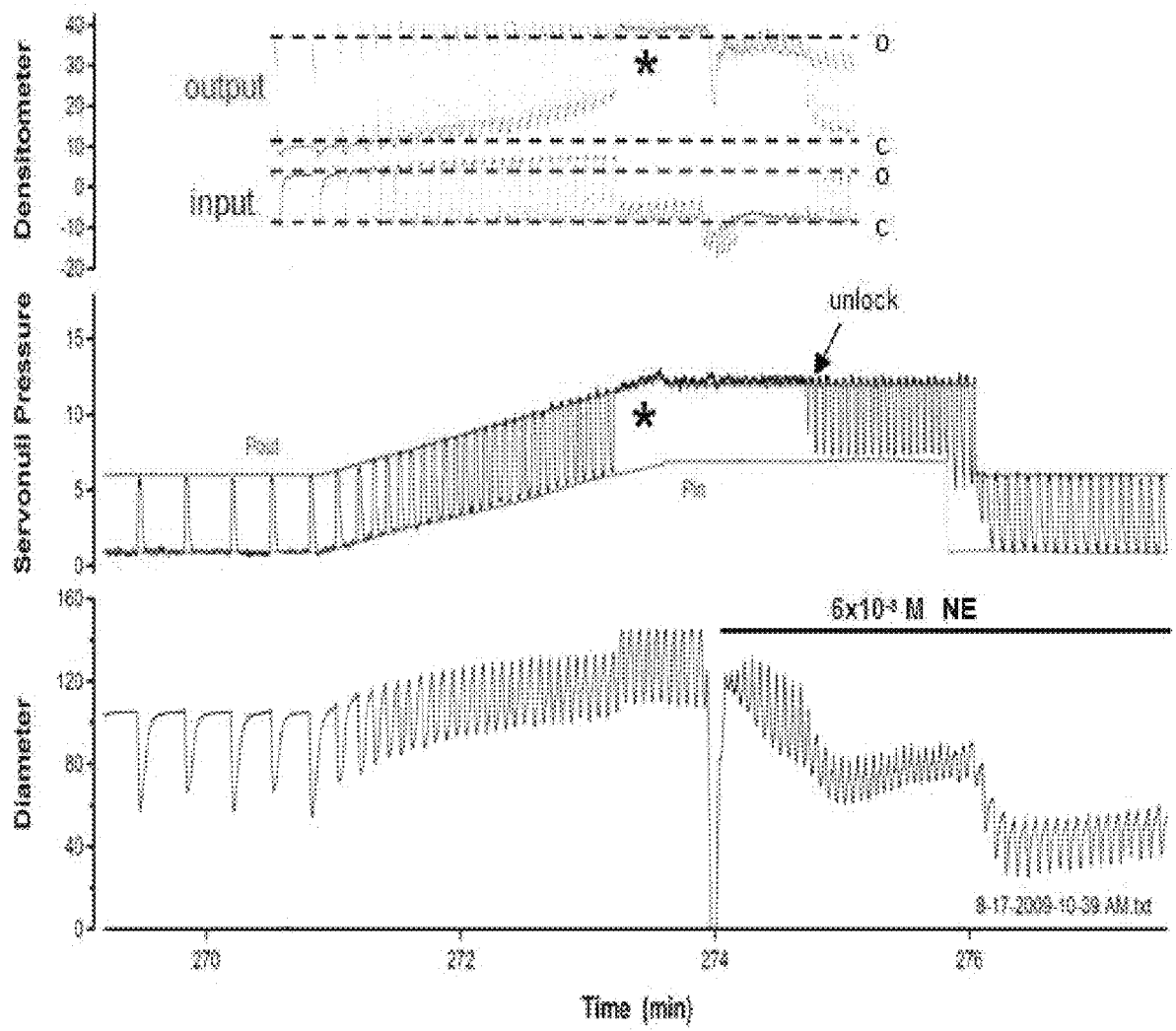
FIG. 3C depicts that vessels failing due to valve lock can be rescued ("unlock") even if pressure remains elevated by using norepinphrine (NE) to induce modest vasoconstriction.

The failure rate due to valve lock is even higher in healthy vessels (~95%) when $P_{out} > P_{in}$ and $P_{out} + P_{in}$ are raised together (a "parallel pressure ramp"; see FIG. 3). This protocol simulates the hydrostatic load experienced by vessels during the development of edema in vivo[94-96]: a normal (modest) uphill pressure gradient with no gravitational load, but with increasing interstitial pressure and lymph formation. Compare the response of a healthy vessel that did not fail (FIG. 3A) to one that did (FIG. 3B). This simultaneous pressure increase can overwhelm the normal myogenic constriction, as evident in both panels. It was found that the application of NE, at a dose that counteracts the loss of tone but does not fuse contractions, relieves valve lock even though pressure remains elevated (FIG. 3C).

Figure 4:
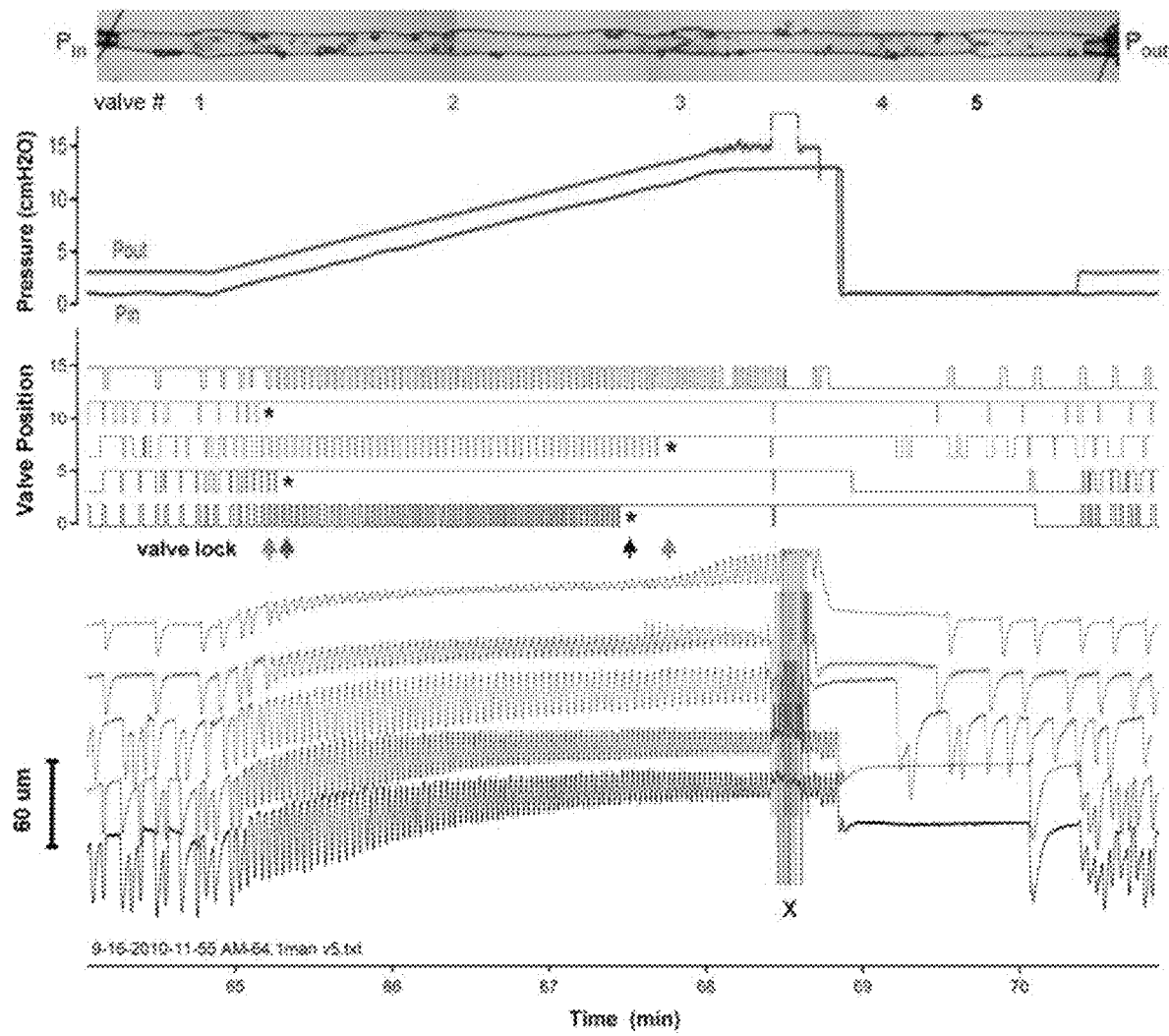
FIG. 4 depicts the progression of valve lock through a chain of WT lymphangions until, at $P_{out}=13$ $cmH_2O$, all but one are open. Valve positions are color-coded to the respective diameter traces, which are offset for clarity. $P_{out}$ pulse to 20 $cmH_2O$ (at "x") transiently closes all valves followed by loss of video focus.

Valve lock also occurs in chains of lymphangions. In FIG. 4, a parallel ramp is imposed on a 5-valve segment (4 complete lymphangions), with a constant, modest $P_{out}-P_{in}$ gradient of 2 cmH$_2$O. Two valves (#2, #4) lock at low pressures ($P_{out}$=4 and 5 cmH$_2$O, respectively, followed by lock of valve #5 at $P_{out}$=12 cmH$_2$O and lock of valve #3 at 13 cmH$_2$O (*). Valve #1 does not lock under these conditions because once the other valves lock, the adverse $\Delta P$=12 cmH$_2$O is sufficient for closure. The valves that lock at lower pressures likely are the downstream valves of segments with weaker contractions, but this is not obvious from contraction measurements alone and must be tested with intraluminal $P_L$ measurements. If lymphangions are typically <1 cm in length then theoretically they only need to pump against a fraction of a cmH$_2$O maximum in a dependent extremity. Thus, an average $P_{out}$ of ~14 cmH$_2$O provides a large safety margin. When valves sequentially lock open, the functional lymphangion doubles in length (then triples, quadruples, etc.) as shown above, after which coordination of the contraction wave must certainly become problematic.

Figure 6A:
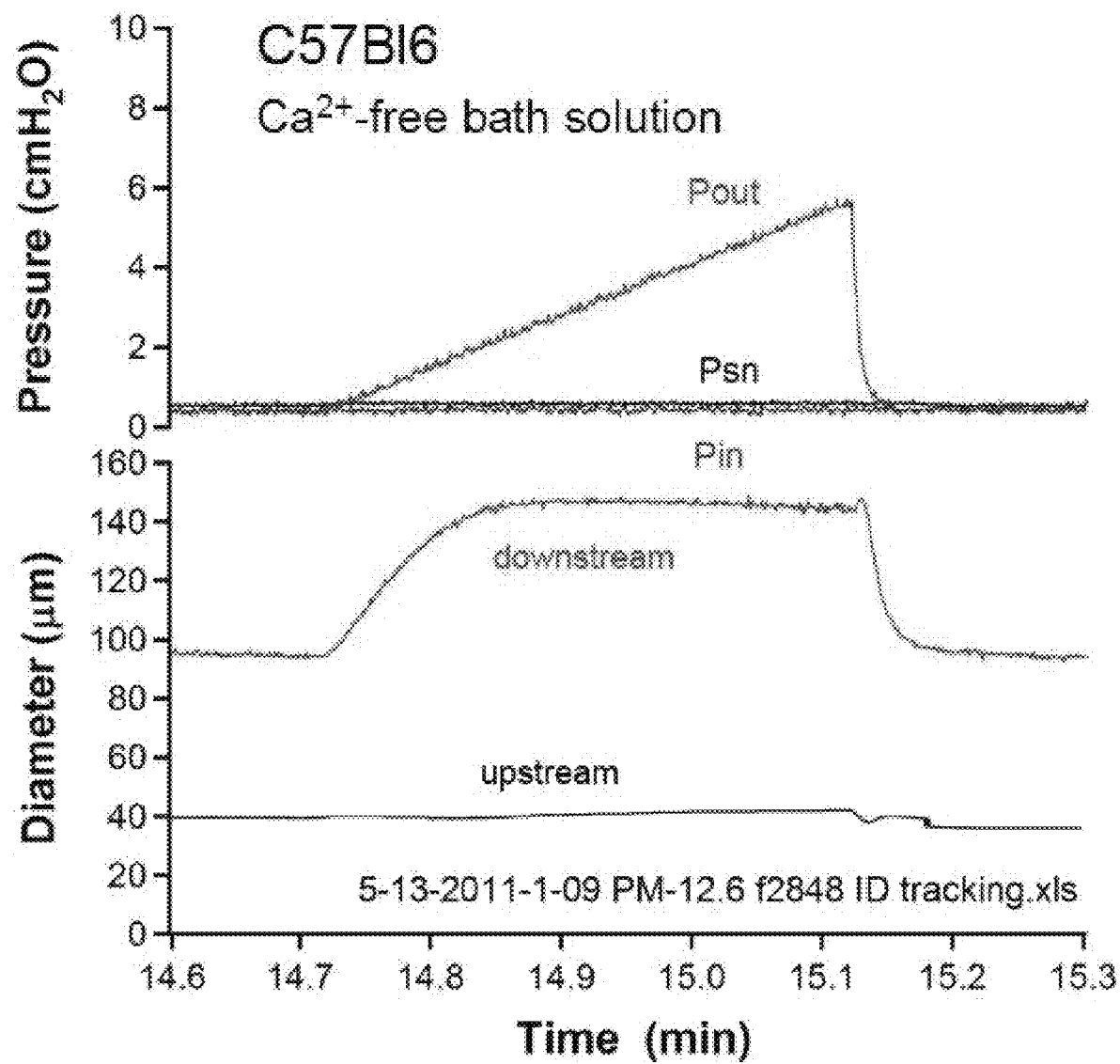
FIG. 6A, FIG. 6B, FIG. 6C and FIG. 6D depict the comparison of back-leak in WT and Foxc2$^{+/-}$ valves in $Ca^{2+}$-free bath to eliminate contractions.
Figure 6B:
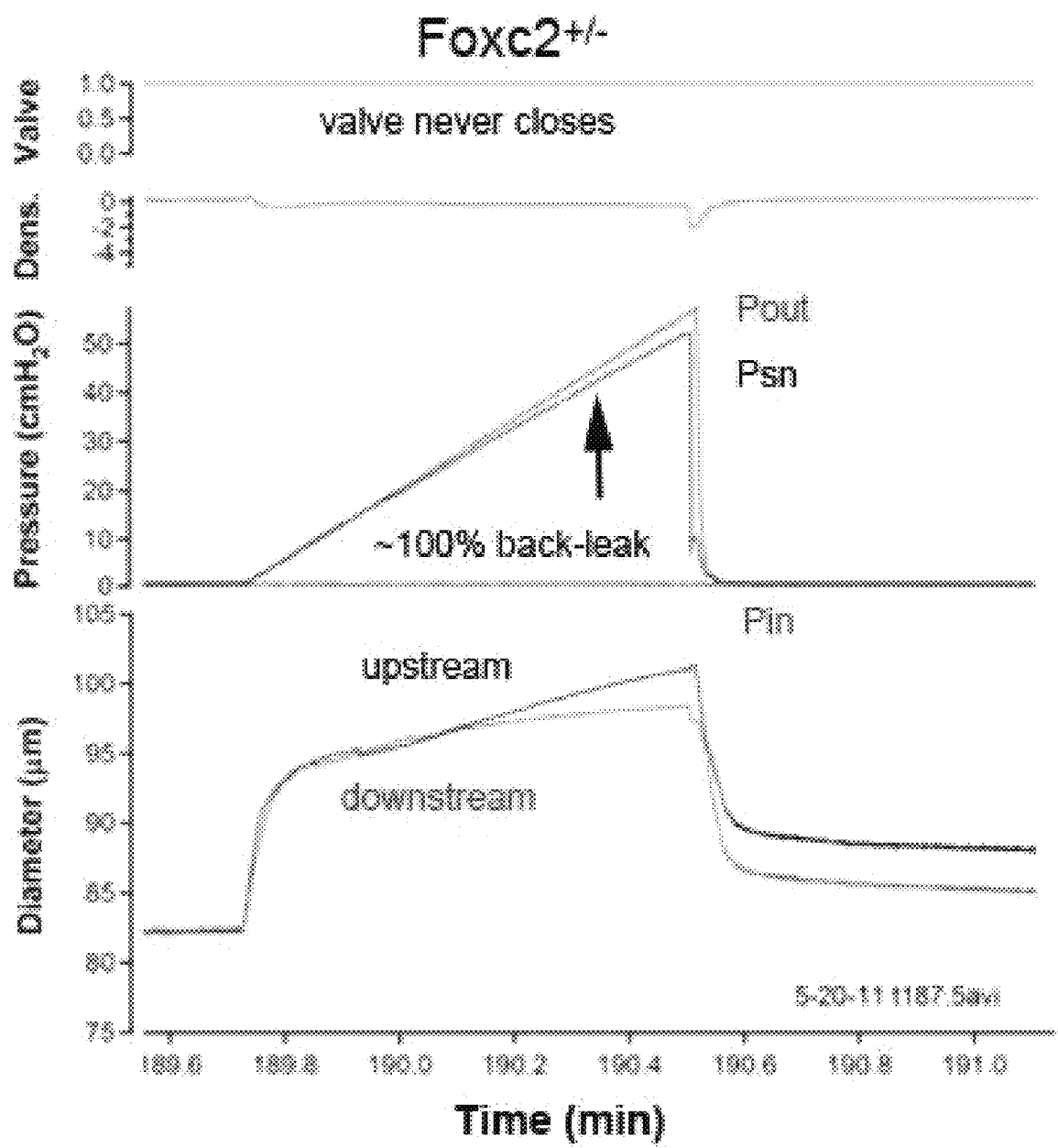
Figure 6C:
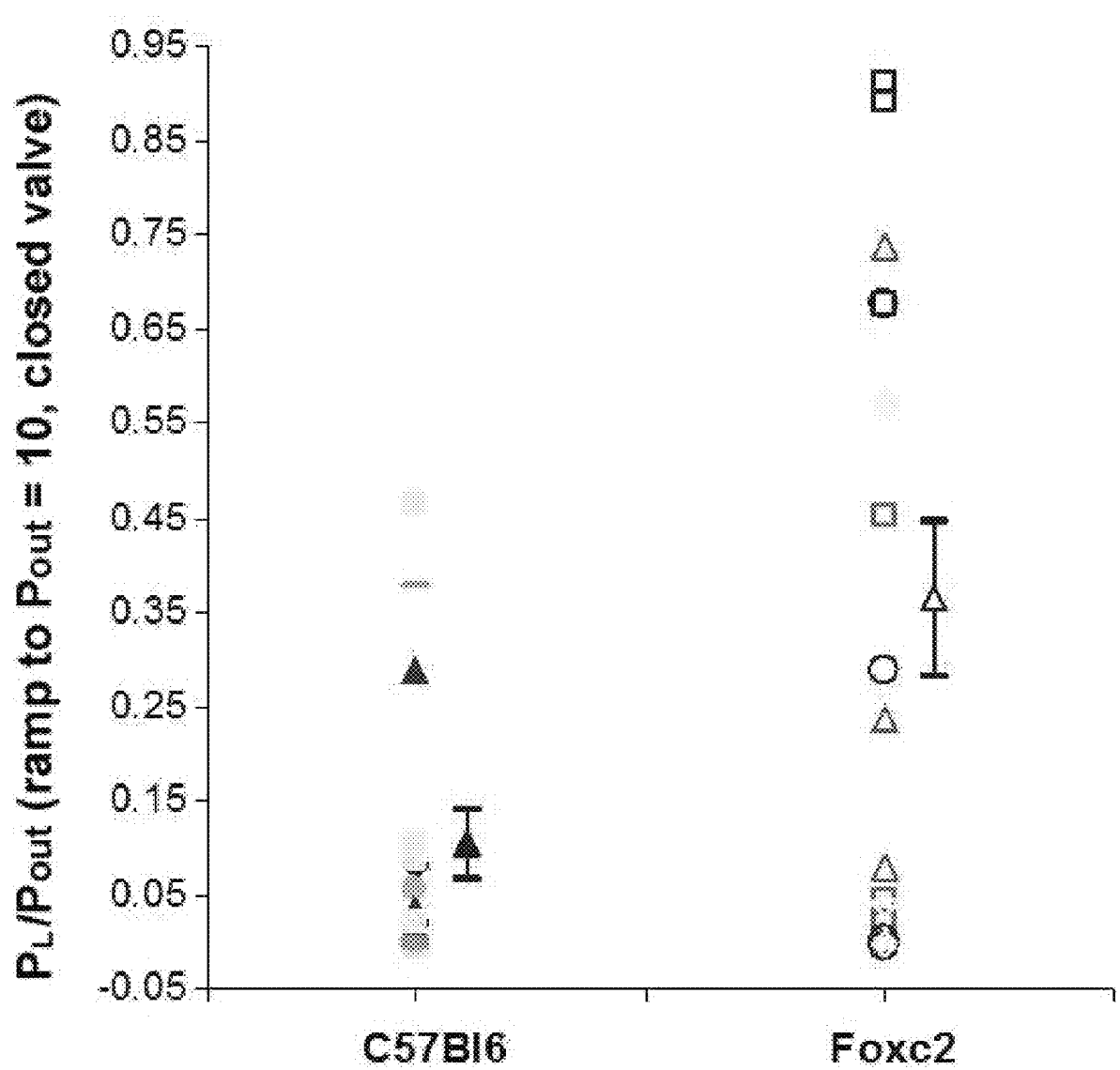
Figure 6D:
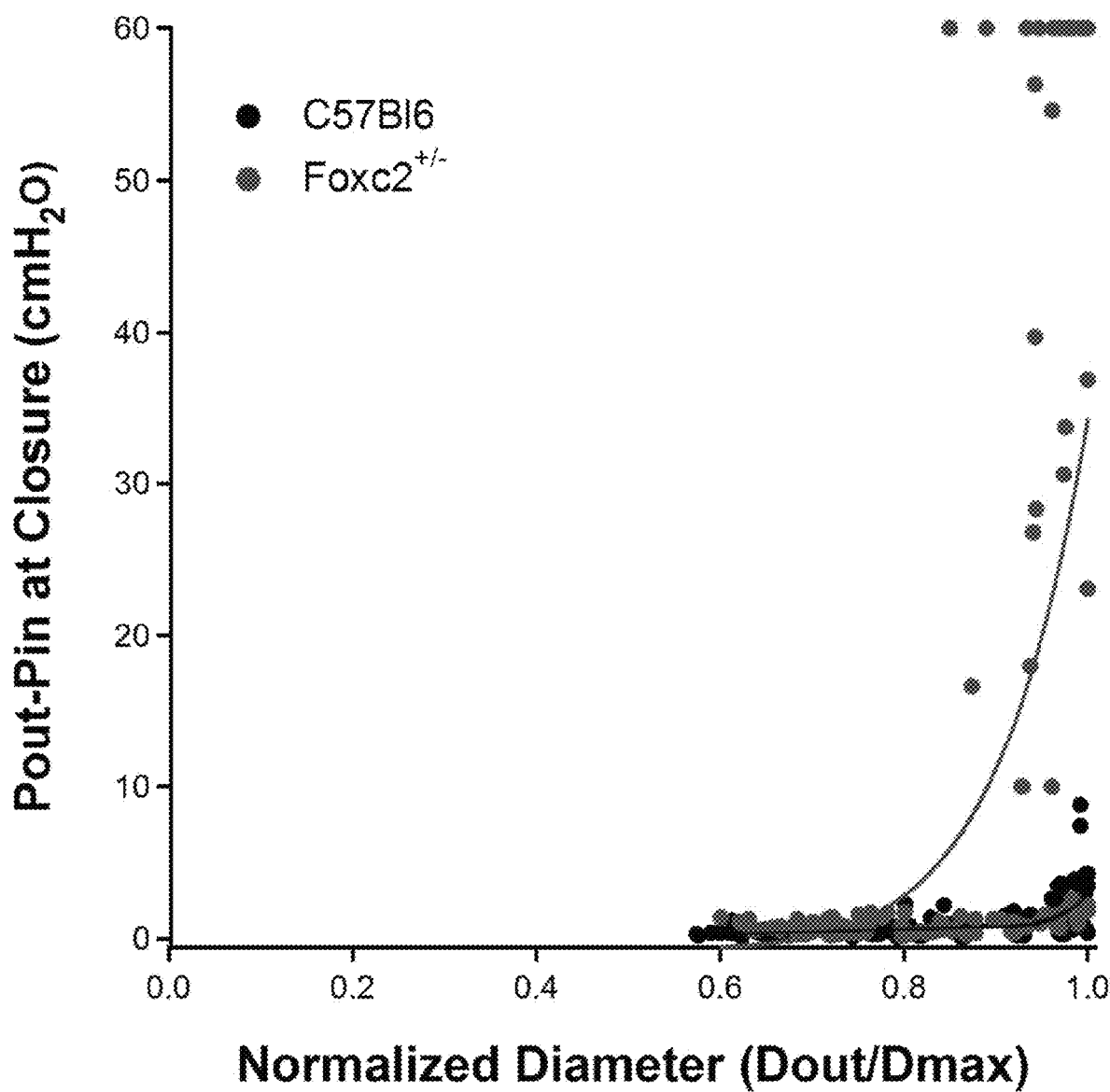

The pressure load that induces pump failure is determined by the force vs preload/afterload relationships of lymphatic smooth muscle, which have been described in detail for rat vessels[22,72]. However, the occurrence of valve lock as an additional mechanism of failure points to other factors as well. What causes valve lock? Valve lock is not incompetence or insufficiency; if it were then the valve would never be able to close properly. But valve lock is reversible: the valve will close with an additional $P_{out}$ pulse (FIG. 4 at "x"); it will also close when the same vessel is put in Ca$^{2+}$-free bath solution and an appropriate $\Delta P$ applied, which is how the passive valve tests disclosed herein are performed (FIG. 6D). Nor is it prolapse, because valve inversion even if a non-physiological (>100 cmH$_2$O) adverse pressure gradient is imposed was not observed. Valve lock is a phenomenon not previously described or appreciated that may contribute to the induction of pump failure in both healthy and diseased vessels. It occurs in part as a consequence of the gating vs pressure relationship of the valve leaflets (FIG. 6D), but it also appears to be influenced strongly by leaflet stiffness and back-leak. The apparent lymphatic valve "insufficiency" (a valve that cannot physically close because the vessel diameter is too large) reported in post-hoc analysis of vessels in chronic lymphedema[28,55,56,90] and included in flow diagrams describing the factors leading to lymphedema[77], is actually valve lock, rather than insufficiency and, therefore can potentially be reversed.

Figure 14A:
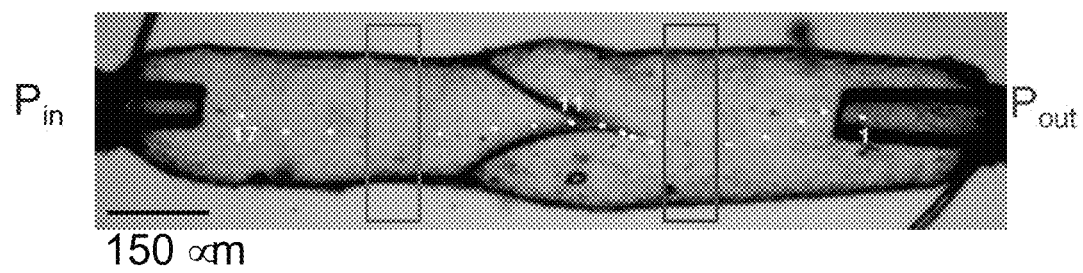
FIG. 14A, FIG. 14B and FIG. 14C depict graphs showing that the closure-diameter relationship is confirmed by particle movement backwards through a valve.
Figure 14B:
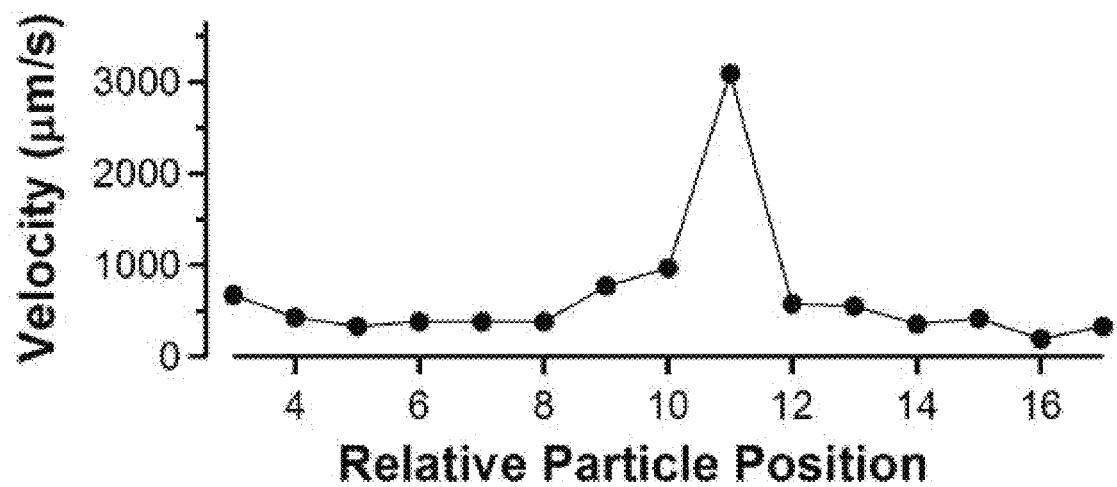
Figure 14C:
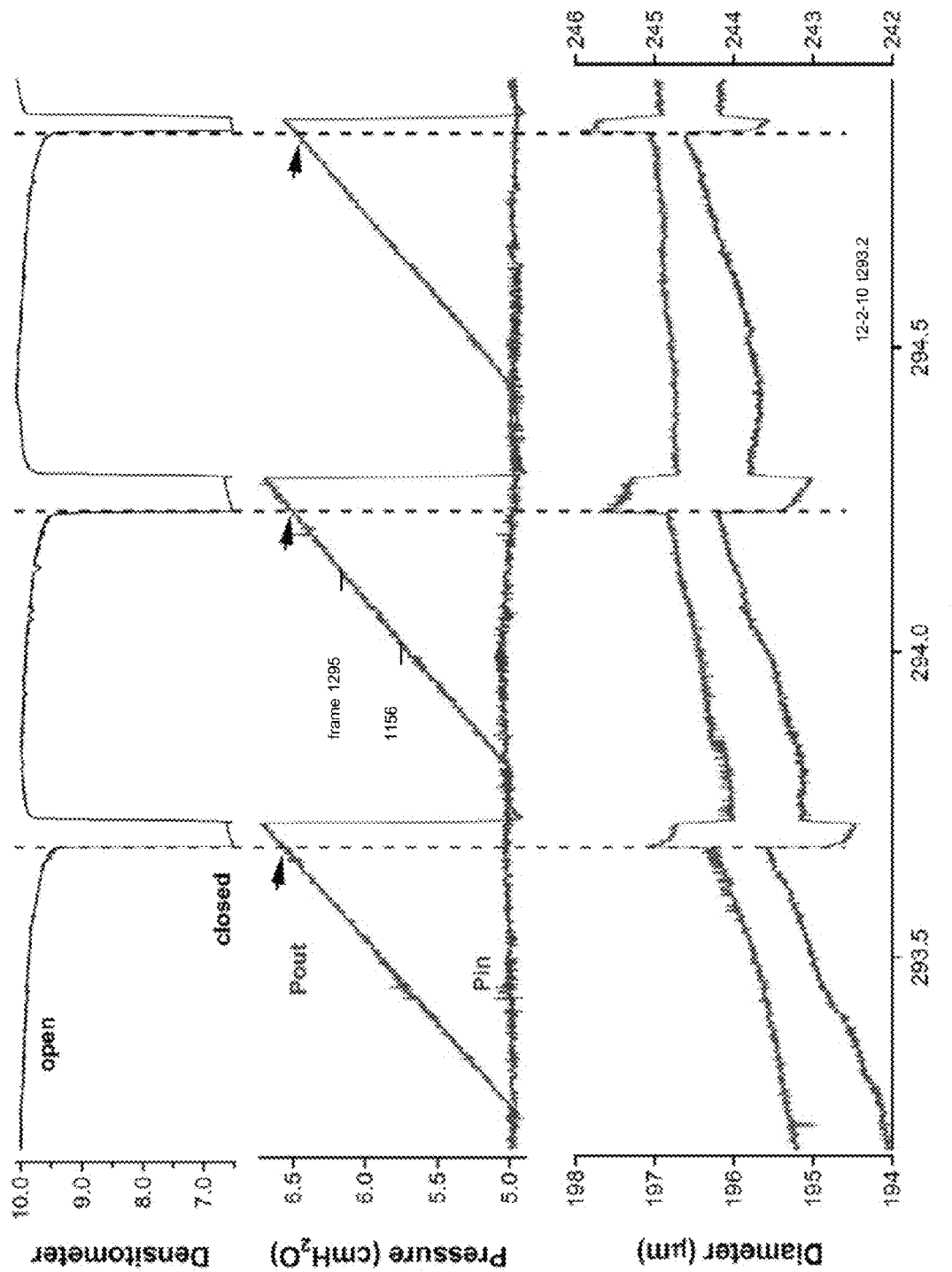
Figure 15A:
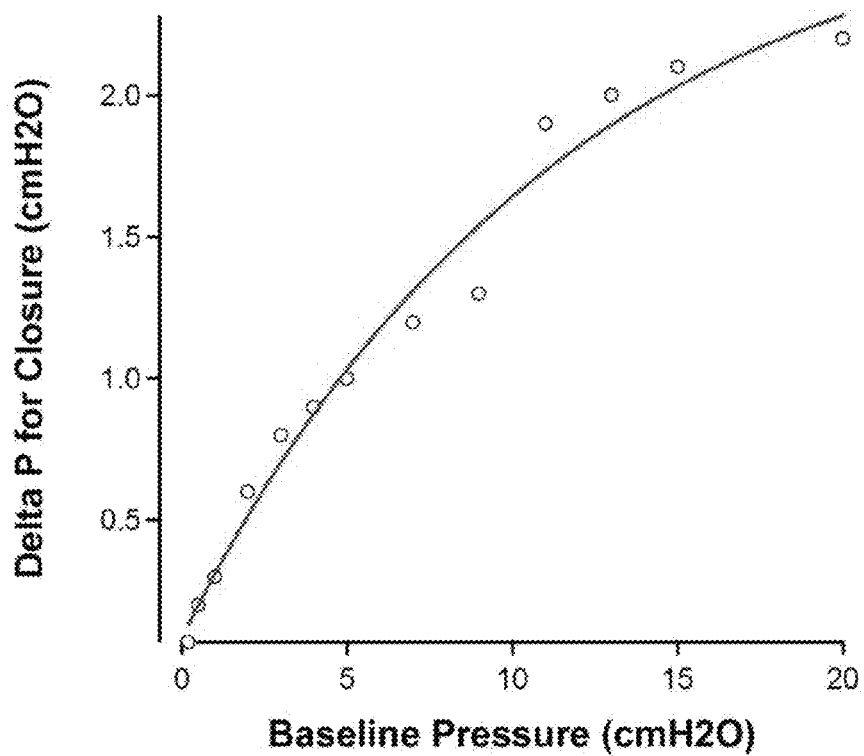
FIG. 15A and FIG. 15B depict graphs showing that the adverse pressure gradient for closure increases with vessel expansion.
Figure 15B:
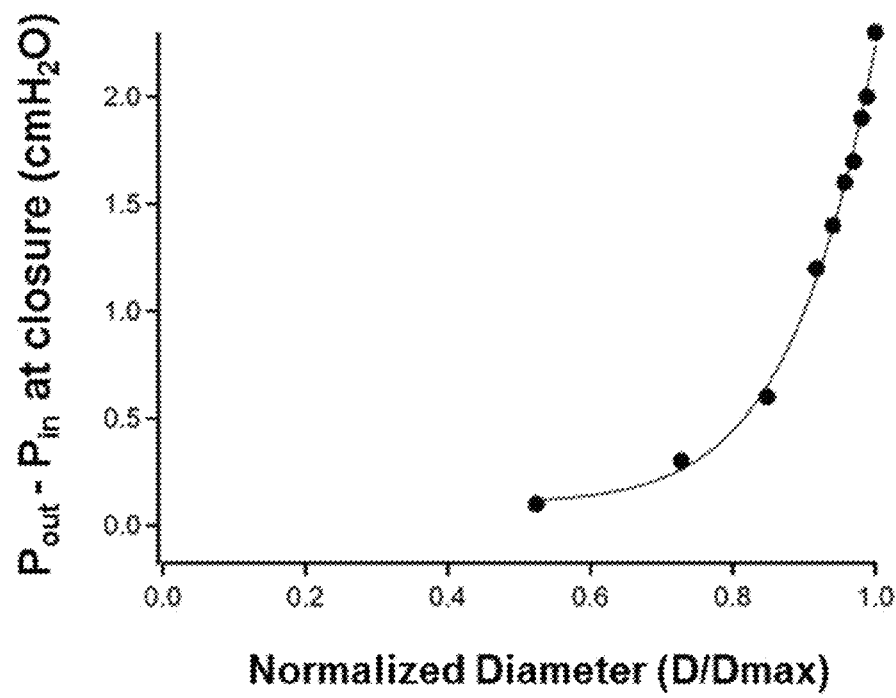

Results demonstrate that valve closure is passive but depends on the diameter of the vessel (FIG. 13A, FIG. 13B, FIG. 13C, FIG. 13D). The closure-diameter relationship was confirmed via particle movement backwards through the valve (FIG. 14A, FIG. 14B, FIG. 14C). The adverse pressure gradient for closure increases with vessel expansion (FIG. 15A, FIG. 15B). Accordingly, valves close easily when baseline pressure and diameter are low. When the vessel is distended, a substantial back pressure is required for valve closure and when a pumping vessel loses tone, the valve is more susceptible to locking open.

Figure 5A:
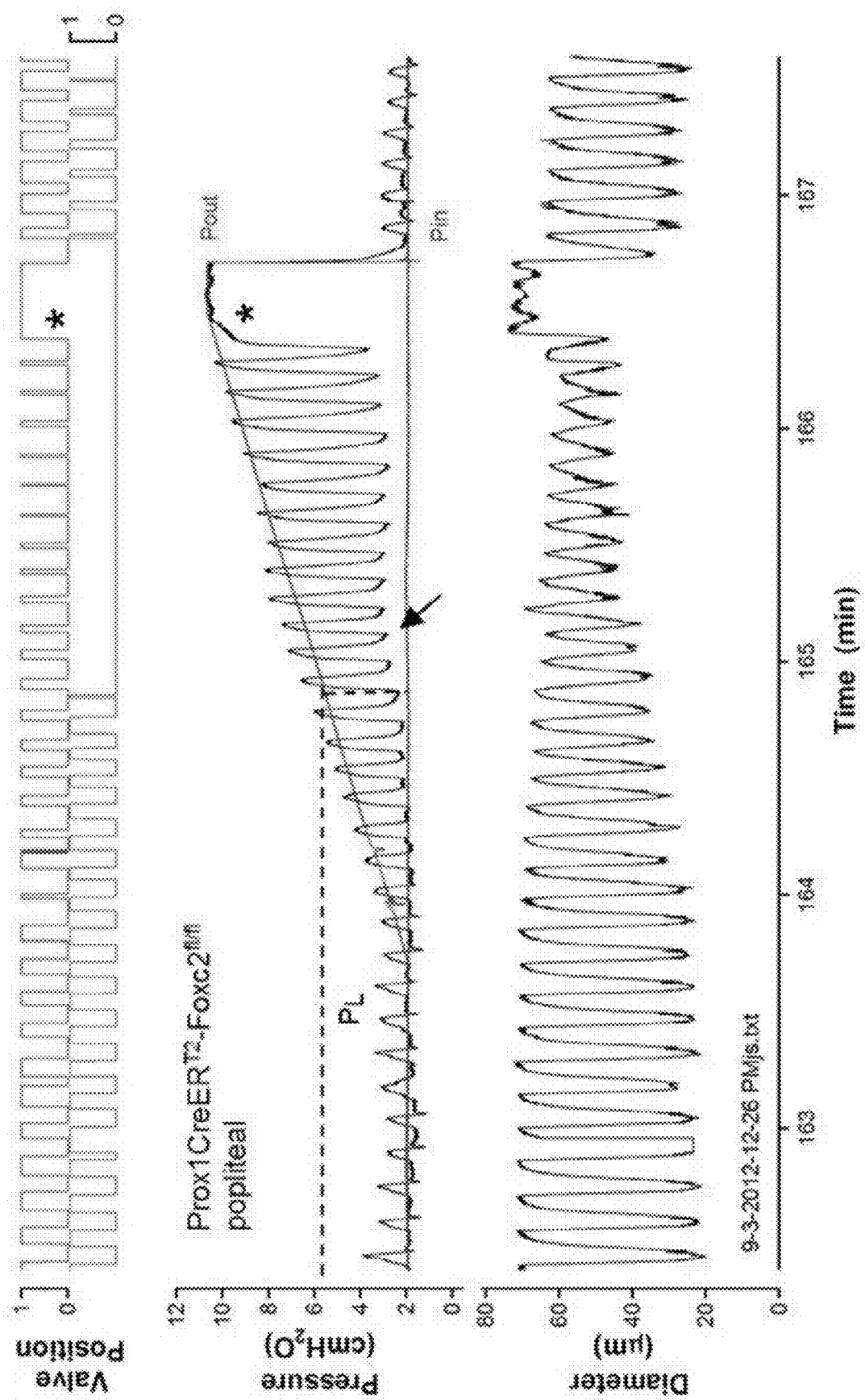
FIG. 5A depicts that in a Foxc2$^{+/-}$ vessel: diastolic pressure ($P_L$) starts to rise during a $P_{out}$ ramp when $P_{out}$ is only 6 $cmH_2O$ (arrow in FIG. 5A) eventually leading to valve lock (*).
Figure 5B:
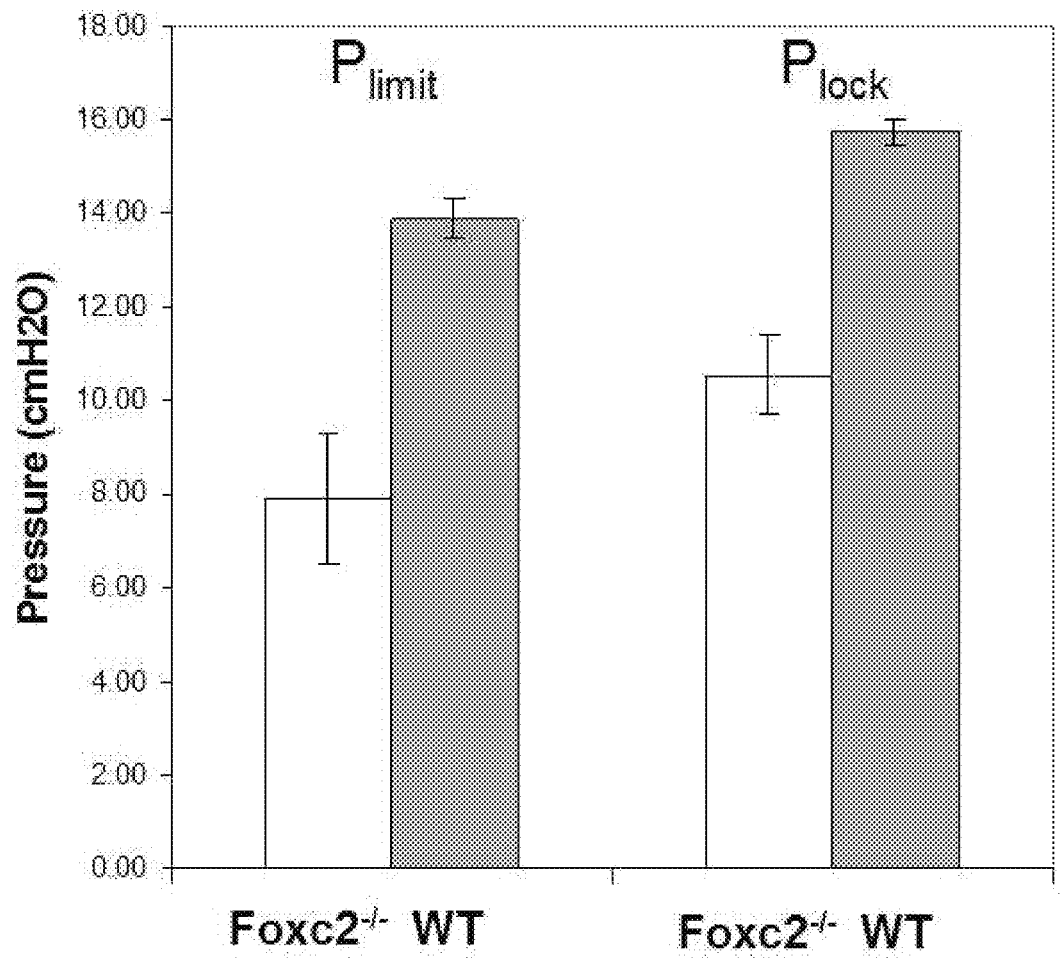
FIG. 5B and FIG. 5C depicts that Foxc2$^{+/-}$ vessels are more susceptible to valve lock which occurs more often and at a lower pressure; likewise, $P_{limit}$ is also lower than control.
Figure 5C:
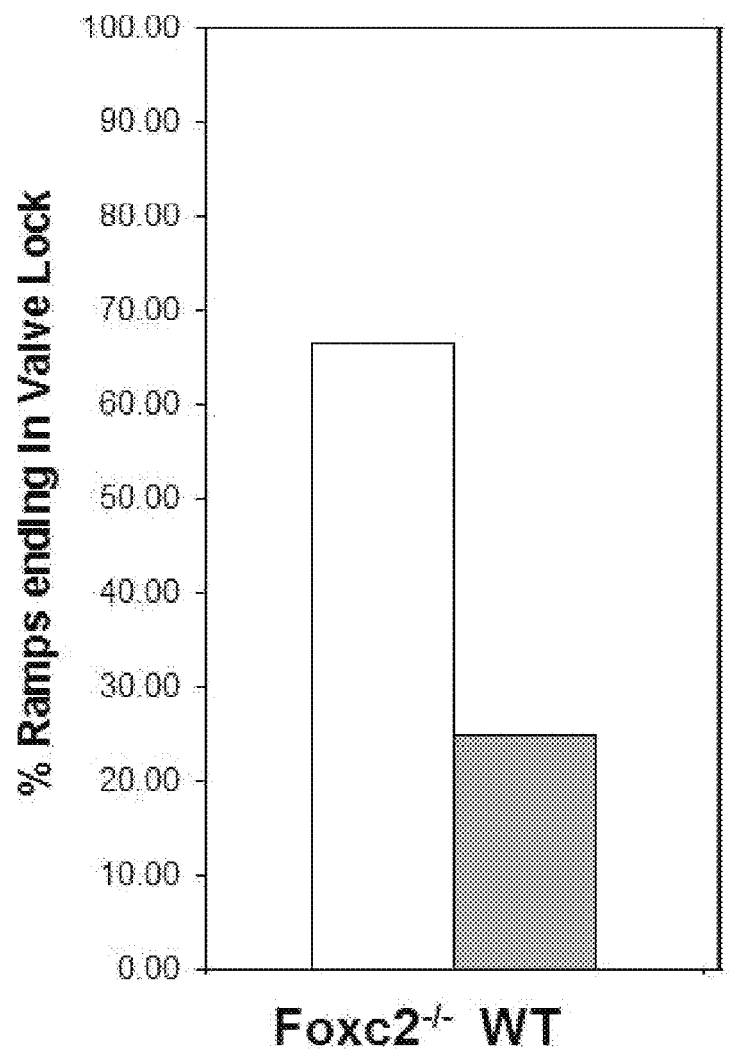
Figure 16A:
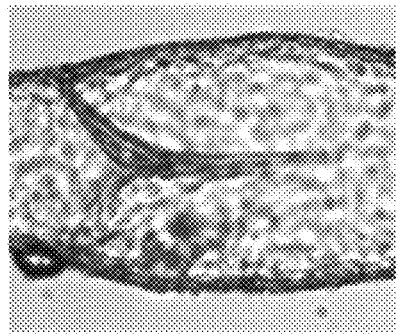
FIG. 16A and FIG. 16B depict images of C57Bl/6 and Foxc2$^{+/-}$ valves. 50% of valves in Foxc2$^{+/-}$ vessels are abnormal.
Figure 16A:
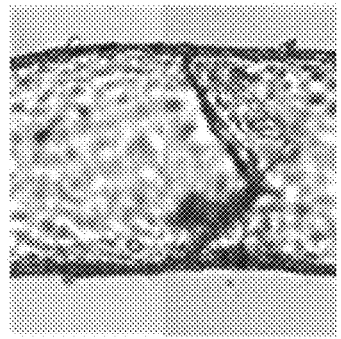
Figure 16B:
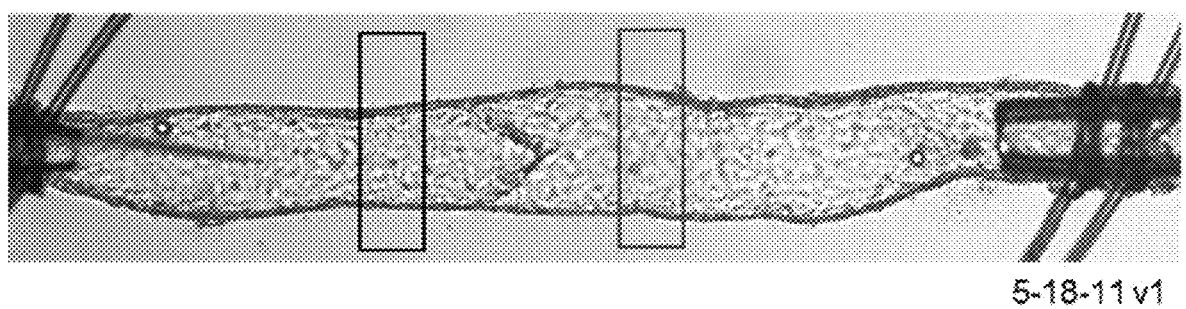

What are the consequences of abnormal valves? Foxc2$^{+/-}$ mice have ~½ the normal number of valves and exhibit different types of valve defects[60] (FIG. 16A, FIG. 16B). Foxc2$^{+/-}$ mice have same lymphatic system defect as human patients with lymphedema distichiasis. Popliteal lymphatics from Foxc2$^{+/-}$ mice exhibit no apparent contractile defects but have unusually poor pumping characteristics (FIG. 5). Although contractions in 1-valve vessels have normal amplitudes at all pressures tested, 2-valve vessels have a limited pumping range and the maximum pressure limit for pumping against an afterload ($P_{limit}$) is lower than for WT (C57Bl/6) vessels.

Figure 17:
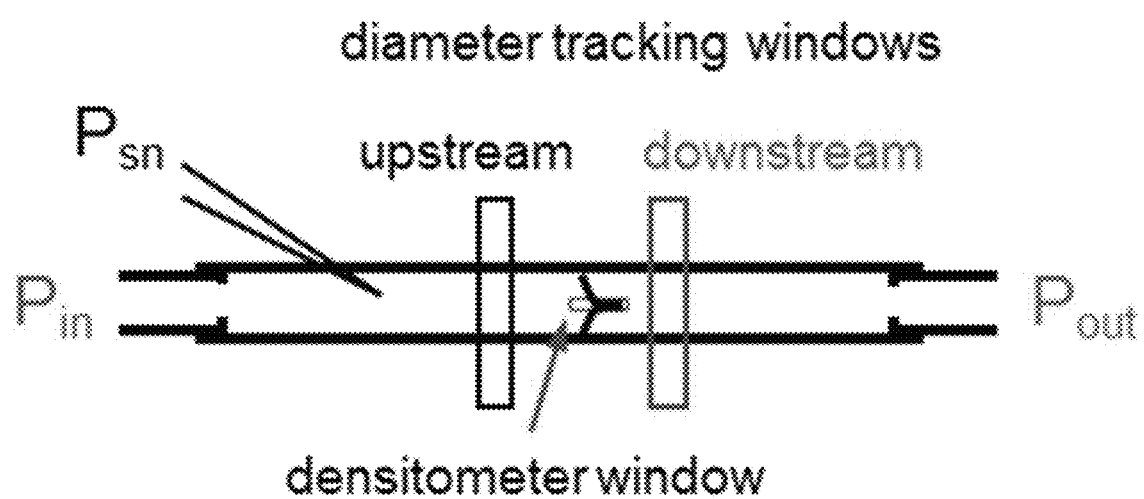
FIG. 17 depicts a schematic of the method to detect and quantify back-leak. Conditions include $Ca^{2+}$-free bath solution and $P_{in}$ held at 0.5 $cmH_2O$. The method starts with the valve closed and then the $P_{out}$ is slowly raised.

The exacerbated pumping defect in Foxc2$^{+/-}$ vessels suggests at least 2 problems: 1) An output valve that is abnormally leaky, allowing some backflow in diastole, even if the valve appears to be completely closed; 2) The contraction wave within the lymphangion becomes unsynchronized so that the pump cannot work efficiently, accounting for the rise in diastolic $P_L$. New tests were developed to measure both of these parameters (FIG. 17, FIG. 6). To quantify the pressure back-leak across a valve, a 1-valve segment was used. $P_{out}$ is raised slightly to close the valve and a $P_{out}$ ramp is imposed while measuring pressure ($P_{sn}$) on the upstream side of the valve with a servo-null micropipette. Back-leak is the ratio $\Delta P_{sn}/\Delta P_{out}$, where 1=complete leak and 0=no leak (FIG. 6B).

Figure 7A:
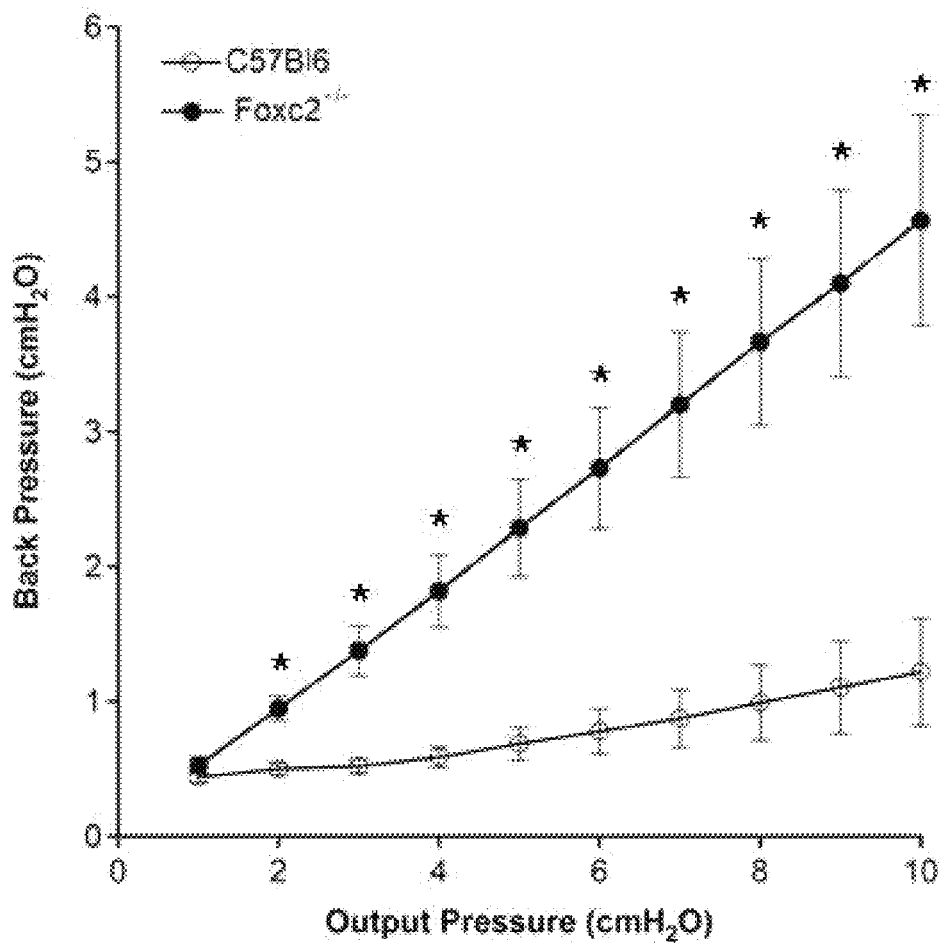
FIG. 7A, FIG. 7B and FIG. 7C depict back-leak in Foxc2 vessels compared to their controls after 4 wks of tamoxifen treatment.
Figure 7B:
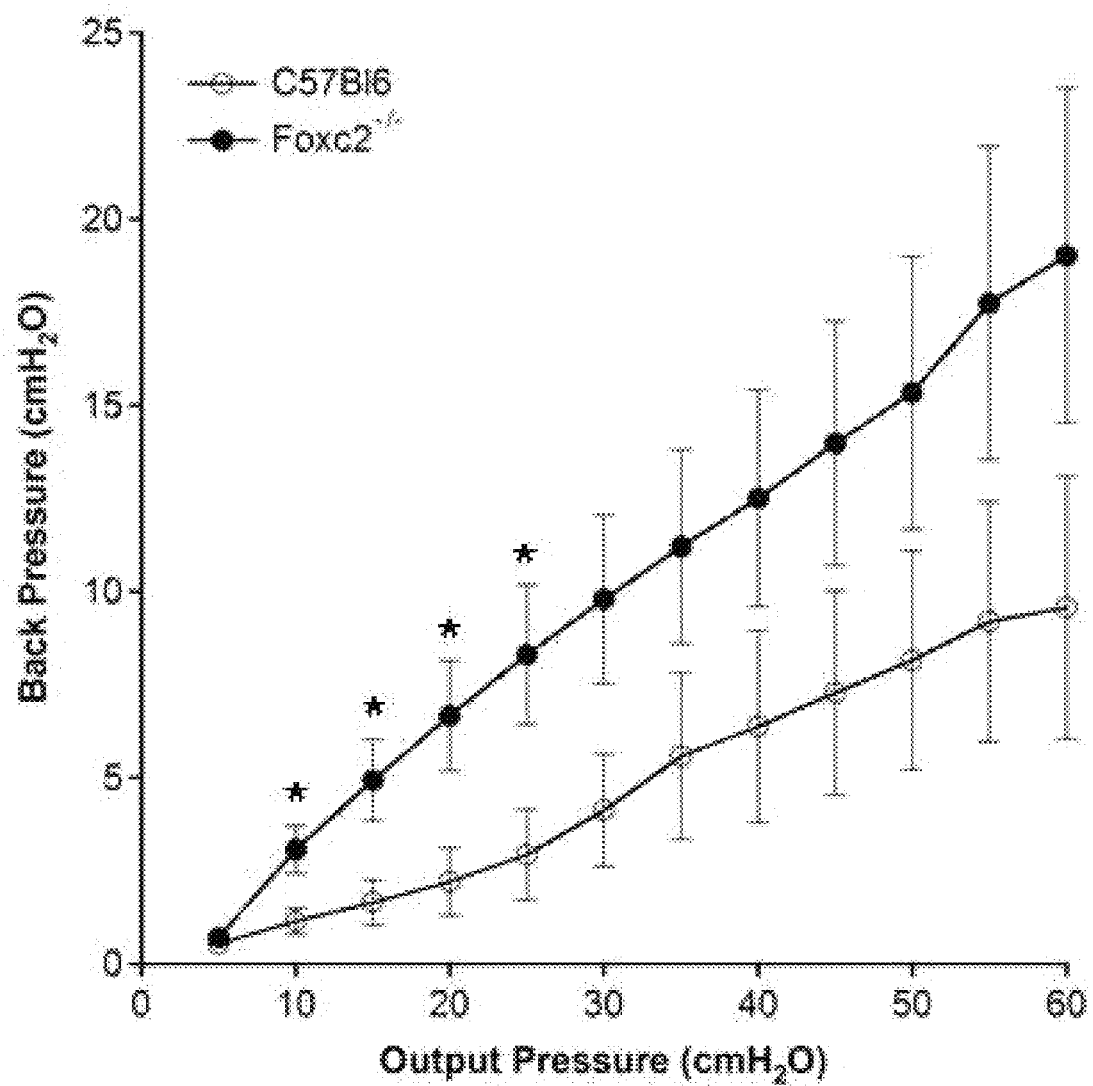

Valve function in vessels from Prox1 CreER$^{T2}$; Foxc2$^{flox/flox}$ mice, which are normal until given tamoxifen to induce deletion of Foxc2, was recently assessed. After 2 wks of tamoxifen treatment, only a slight back-leak if $P_{out}$ is raised to 60 cmH$_2$O is detected. After 4 wks treatment, some of the mice begin to develop visible foot pad edema[67] and significant back-leak in both low- and high-pressure tests is detected (FIG. 7A, FIG. 7B).

In summary, novel methods were developed to assess contractile function in collecting lymphatic vessels from normal and Foxc2-deficient mice. Pressure is controlled at each end independently, allowing simulation of the pressure load experienced by a vessel in a dependent extremity before or during the development of edema. In healthy vessels, lymphatic pump failure is determined by an interaction of the mechanical properties of lymphatic muscle (preload, afterload, inotropy) and, surprisingly, by the valve characteristics (stiffness, back-leak). Even healthy vessels undergo a previously unrecognized type of valve dysfunction (valve lock), causing catastrophic pump failure, when subjected to moderately high output pressure loads or combined input+output pressure loads. Vessels with altered valve properties from Foxc2$^{+/-}$ and Foxc2$^{-/-}$ mice are more susceptible to valve lock, leading to pump failure at lower pressures.

None of these tests or analyses have ever been performed previously on lymphatic vessels, either in normal or knock-out animals. These studies are the first such investigation of the mechanisms underlying pump failure in lymphangions of both healthy and Foxc2-deficient vessels to pressure loads that simulate those experienced in a dependent extremity during the development of edema.

Importantly, these results also suggest that vessels can be rescued from valve lock by induction of a modest vasoconstriction even if pressure is elevated. It was hypothesized that valves described as 'incompetent' or 'insufficient' in clinical studies[28,56,77,90], particularly in the early stages of the disease, actually represent valve lock and thus may be treatable. NE appears to be an optimal pharmacologic tool that reverses valve lock while enhancing other aspects of pump function. A pharmacological approach to treating the failed lymph pump could represent a potential new strategy for treating forms of lymphedema that involve pump and valve dysfunction.

Example 2. Mechanisms Underlying Valve Lock and Pump Failure when Healthy Lymphangions are Forced to Pump Against Elevated Outflow Pressure In isolated single lymphangions, two types of pump failure occur as the lymphangion is subjected to a progressive rise in outflow pressure, simulating the pressure load on the vessel in a dependent extremity. 1) The pump either gradually weakens until it cannot eject, at which point internal pressure development becomes insufficient to open the output valve; or 2) the output valve "locks" open ("valve lock") as pressure equilibrates across it within one contraction cycle. The change in intraluminal pressure ($P_L$) preceding valve lock can be gradual or rapid (FIG. 2C, FIG. 3B); the underlying mechanisms are not completely clear. It is proposed that valve lock reflects the true state of the apparent "incompetent" or "insufficient" valves described in the limbs of patients with acquired lymphedema[55,75], at least in the acute phase of the disease, when the vessels are still healthy. It is hypothesized that 3 mechanisms interact to cause valve lock/pump failure: 1) mechanical properties of lymphatic muscle as determined by preload, afterload and inotropic state, 2) the properties of the lymphatic valves (stiffness and back-leak) and 3) the coordination of the contraction wave. The contributions of these mechanisms will be dissected first in single lymphangions and then in multiple-lymphangion segments.

Figure 8A:
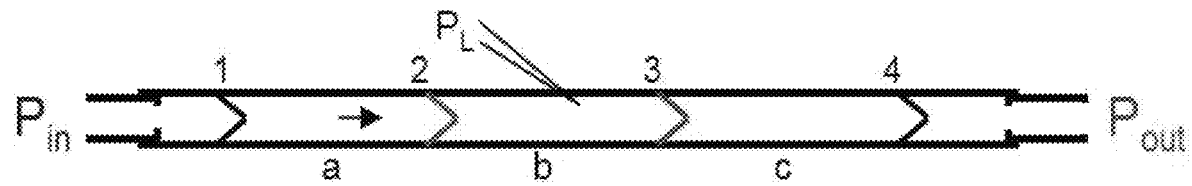
FIG. 8A, FIG. 8B and FIG. 8C depicts vessel configurations.
Figure 8B:
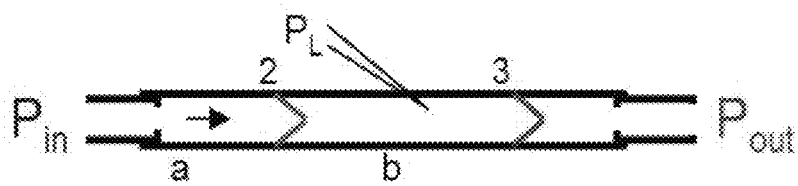

What are the limits of the healthy lymphatic pump when an output load is imposed and when a simultaneous input/output load is imposed? Further, does valve failure in one lymphangion of a chain trigger premature failure of other lymphangions? It has been previously characterized the conditions (preload, afterload) under which single lymphangions (configuration II; FIG. 8B) fail[22,72], but little is known about the behavior of chains of multiple lymphangions (configuration I; FIG. 8A), in vitro or in vivo. Thus tests will be conducted of 4-valve segments (3 complete lymphangions) from WT mice in response to selective, ramp-wise increases in $P_{out}$ at a rate of 2 cmH$_2$O/min. It has been determined that this rate allows adequate time for adaptation. The middle lymphangion is protected from artificial boundary conditions (no pressure fluctuations) existing at the cannulation pipettes. When $P_{out}$ is raised, segments B and A are potentially protected by segment C from experiencing the full output pressure load (if C returns diastolic pressure to $P_{in}$ levels, then B will not experience the increased afterload). Because $P_L$ can only be measured in one segment (withdrawing the pipette leaves a hole), $P_L$ will be measured in A in one series of studies, B in another series and C in another series to understand the complete behavior; but diameters and valve positions will be measured in all segments in all series. Passive diameters will be measured in Ca$^{2+}$-free bath at the end of the protocols.

Figure 8C:
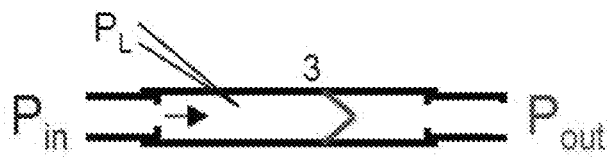
Figure 8D:
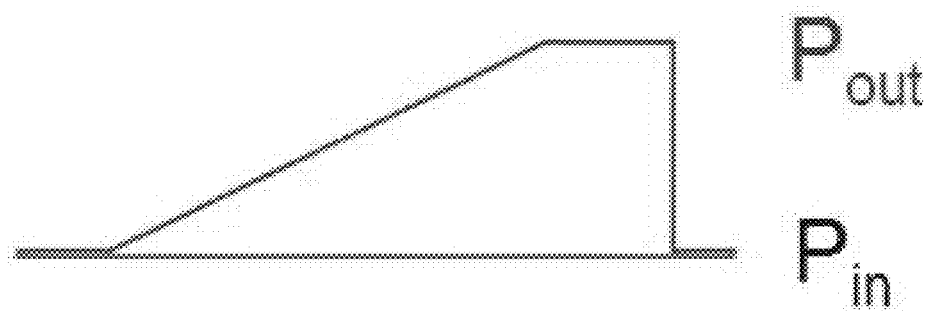
FIG. 8D and FIG. 8E depict pressure waveforms.
Figure 8E:
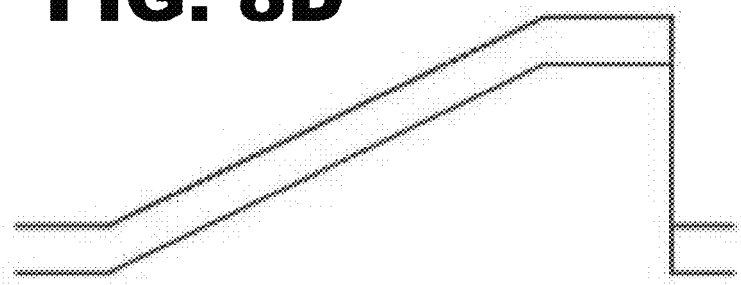

What is the cause-effect relationship between pump failure and valve lock and what factors interact to determine valve lock? In response to a parallel pressure ramp (waveform II; FIG. 8E)—simulating the pressure conditions that develop in edema—the lymphangion failure rate is 100% due to valve lock, even in healthy vessels, compared to ~50% failure when $P_{out}$ is selectively raised. It was hypothesized that during a parallel ramp, a rise in preload prevents the myogenic constriction (FIG. 2) that otherwise keeps EDD low, allowing valve closure at a low adverse $\Delta P$ (FIG. 6D); as EDD increases and a larger $\Delta P$ is required to close the output valve in diastole (a leftward shift in the closure curve), the lymphangion becomes increasingly susceptible to valve lock. Any back-leak across the valve, or lapse in contraction wave synchrony may trigger valve lock. Does the segment with the leakiest valve fail first? Is it the segment with lowest force production? To test this, waveforms I-II will be imposed and, as above, $P_L$ will be measured in one segment at a time per series, but all diameters and positions will be measured in each series to determine whether failure occurs because a valve stops opening or locks open in systole. After the first segment to fail has been identified, the chain will be shortened to configuration II to measure the direct effects of preload/afterload on that particular lymphangion; then it will be shortened to configuration III (FIG. 8C) to measure the valve closure and back-leak properties of its output valve. Shortening simply involves advancing the input or output pipettes appropriately and retying the vessel to the cannulae-procedures that have been used in Foxc2$^{+/-}$ protocols[67,70]. In each of these configurations, the videos will be analyzed with novel analysis methods (FIG. 12) to look for changes in contraction wave synchrony, velocity and direction, with particular focus on the events occurring immediately prior to valve failure.

Example 3. Consequences of Lymphatic Valve and Pump Dysfunction in Foxc2$^{+/-}$ and Foxc2$^{-/-}$ Models of Primary Lymphedema Valve formation and maintenance are controlled by the transcription factor FOXC2[60]. The loss of one FOXC2 allele in mice (Foxc2$^{+/-}$) is associated with a reduction in the number of lymphatic valves, loss of key ECM protein components in other valves, and abnormal back-leak of lymph[60]. In humans FOXC2 mutations underlie the disease lymphedema distichiasis[10,47] which is characterized by limb edema due to defective lymphatic[47,60] and venous valves[48]. Because valve properties have a significant impact on lymphatic pumping in ways not previously anticipated (FIG. 2, FIG. 3, FIG. 4) it is predicted that lymphatics from Foxc2$^{+/-}$ and inducible Foxc2$^{-/-}$ mice (Prox1CreER$^{T2}$; Foxc2$^{flox/flox}$) will show both valve and pump defects; preliminary data support this hypothesis (FIG. 5), but the protocols need to be completed and extended to chains of multiple lymphangions.

Are Foxc2 vessels more susceptible to pump failure or to valve lock? Popliteal lymphatics will be isolated from Foxc2$^{+/-}$ mice, or from inducible Foxc2$^{-/-}$ mice, and tested in configurations I and II with waveforms I and II. Protocols on single lymphangions will be conducted first in order to complete a preliminary data set (FIG. 5), followed by protocols on lymphatic chains. Age-matched C57Bl/6 mice will serve as controls for Foxc2$^{+/-}$ mice. It is predicted that that Foxc2-deficient vessels will exhibit a lower maximum output pressure against which they can pump ($P_{limit}$), will undergo valve lock at a lower pressure ($P_{lock}$), and that valve lock will occur more frequently (in response to waveform I). Foxc2-deficient lymphangions that fail due to valve lock are also predicted to have abnormally leaky valves and uncoordinated contraction waves.

Figure 7C:
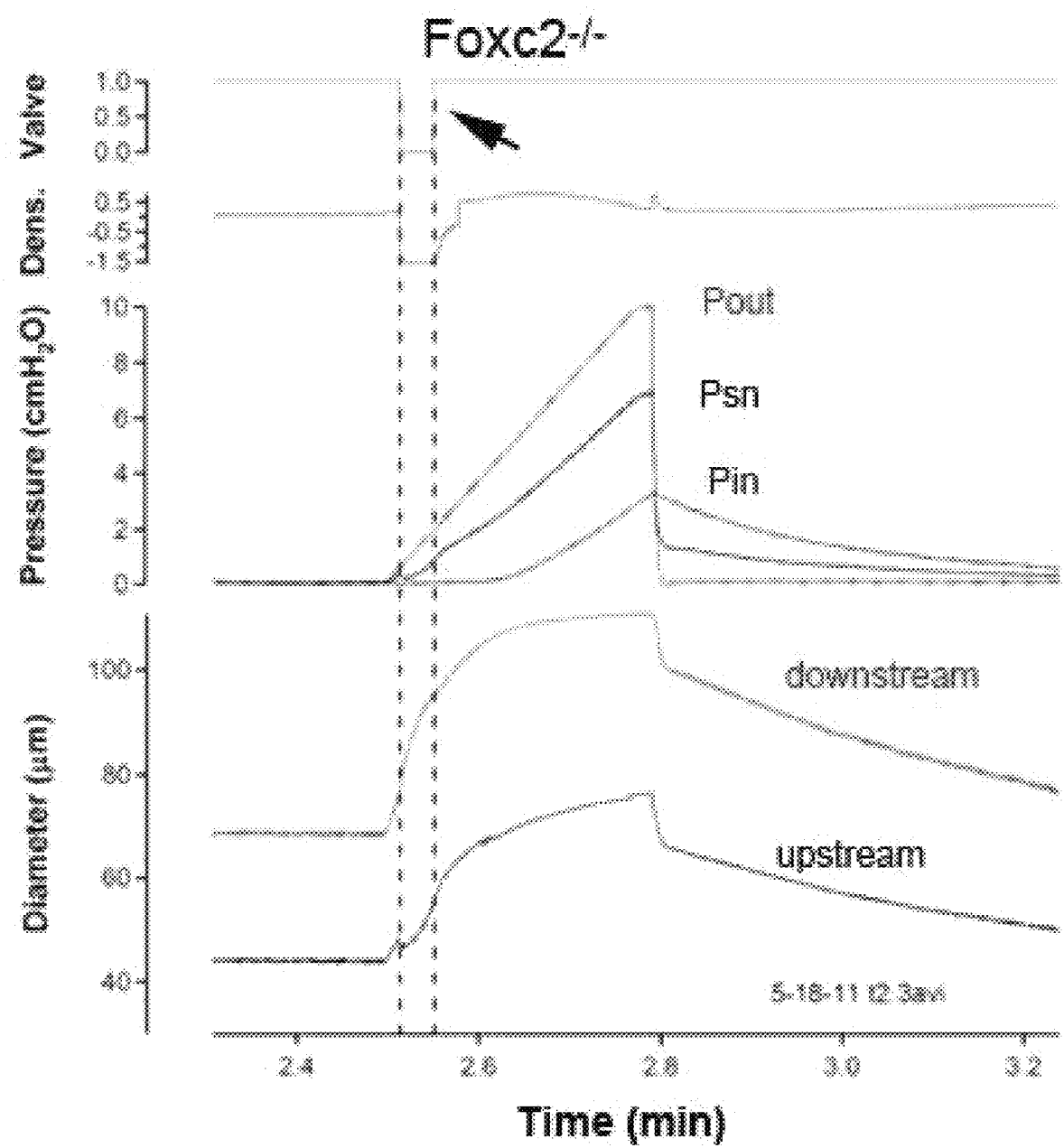

Next it was asked is the Foxc2/phenotype more severe than the Foxc2$^{+/-}$ phenotype? Complete deletion of Foxc2 results in the absence of lymphatic valves[60] and embryonic mortality[38]; thus functional studies cannot be performed on constitutive FOXC2 null mice. Inducible Foxc2 null mice are available and have been used for preliminary studies (FIG. 5, FIG. 6). The mice will be treated for 2 or 4 weeks with tamoxifen (10 mg/ml, 2/wk). For inducible Foxc2$^{-/-}$ mice, age-matched C57Bl/6; Foxc2$^{flox/flox}$ mice treated with the same tamoxifen regime, will serve as controls. It is predicted that both pumping defects and valve defects (closure v diameter, back-leak) will increase in severity following loss of Foxc2. Because preliminary data show that a small increase in back-leak (not shown) and deformed valves can be detected at 2 wks (FIG. 11) with more substantial leaks at 4 wks (FIG. 7), the following hierarchy of severity is predicted: 2 wk Foxc2$^{-/-}$<Foxc2$^{+/-}$<4 wk Foxc2$^{-/-}$<6 wk Foxc2$^{-/-}$. As the tamoxifen treatment is extended to 6 wk, a more severe phenotype is expected, with the mice consistently developing hind-limb edema between 4-6 wks. Foxc2 plays roles in both valve development and maintenance, thus its deletion during development may have more severe consequences for valve structure/integrity than its knock down in mature valves[67].

Additionally, it was asked do functional defects correlate with structural changes? After completion of studies on the 3 types of Foxc2-deficient vessels, each vessel with intact output valve will be fixed and stained for ECM proteins in order to correlate changes in function with changes in ECM deposition. As some normal-looking valves are fairly leaky (FIG. 6C) for reasons unknown, it is expected that they will show reduced ECM protein deposition in the valve region and the changes will be more severe in the very leaky valves from vessels with Foxc2 deletion. Foxc2 loss is also associated with increased mural cell recruitment to collecting lymphatics[60]. Whether this occurs in mature animals after inducible loss of Foxc2 is not known, therefore the vessels will be stained for SM a-actin or myosin heavy chain to determine the distribution of SM cells. It will be important to know if increased SM recruitment leads to coordination defects.

Example 4. Principles by which Pump Dysfunction can be Rescued in Healthy and Foxc2-Deficient Lymphatic Vessels Preliminary data suggest that healthy lymphangions which fail due to valve lock in the face of an imposed afterload can be rescued using NE to induce modest vasoconstriction (FIG. 3C). Presumably the constriction counteracts the loss of myogenic tone at the base of the output valve, shifting the valve closure relationship rightward, so that only a small adverse ΔP becomes sufficient to close the valve. It is predicted that the working range of a lymphangion pumping against an output load, but has not yet failed, can be extended by prophylactic application of NE.

In vivo methods are preferred, when possible, to study lymphatic function in the intact animal in the context of the complete array of normal regulatory influences. However, such methods are limited by lack of pressure and flow control. Importantly, in both rat and mouse lymphatic vessels a pressure increase of only 1-1.5 cmH$_2$O can significantly increase EDD, almost double FREQ and cut AMP in half[22,69]; thus unmeasured/unknown pressure changes can lead to misleading interpretations of in vivo data, particularly in the context of testing contractile function[34,40,44]. After comprehensive testing under defined conditions in vitro, the information obtained will be applied to test the concept of pump rescue in vivo. Both healthy and Foxc2-deficient vessels will be used.

It was first asked under what conditions can a failed lymph pump be rescued pharmacologically? The conditions under which a failed pump in healthy single lymphangions (configuration II) can be rescued at fixed levels of preload/afterload[72] will be tested. Both α- and β-adrenergic agonists have been screened. β-adrenergic agonists produce pronounced dilation and are therefore not useful. Norepinephrine (NE), which activates both $α_1$- and $α_2$-adrenoceptors, causes dose-dependent ($10^{-8}$ to $10^{-7}$M) increases in frequency, tone and inotropy (FIG. 9). This combination is optimal[22,72] provided the effects are limited and do not compromise filling. NE will first be applied abluminally then, after the dose has been optimized, intraluminal application will be tested using an inner pipette[71]. LECs have a reasonable baseline permeability[68] to small molecules that should not substantially limit diffusion of NE but may nevertheless alter the effective dose range. The ultimate goal is not so much specificity of action or a particular dose as effectiveness in treating a failed/failing lymphatic pump in vivo through application to the skin. NE will be applied after valve lock/pump failure occurs, while maintaining elevated pressure to see under what conditions failure can be reversed. NE will then be applied prior to an imposed output load to see if the working range of the vessel ($P_{limit}$, $P_{lock}$) can be extended to higher pressures. The fact that waveforms I and II can be imposed several times on the same segment with pump failure occurring consistently at the same pressure ±0.5 cmH$_2$O will be taken advantage of.

Figure 9A:
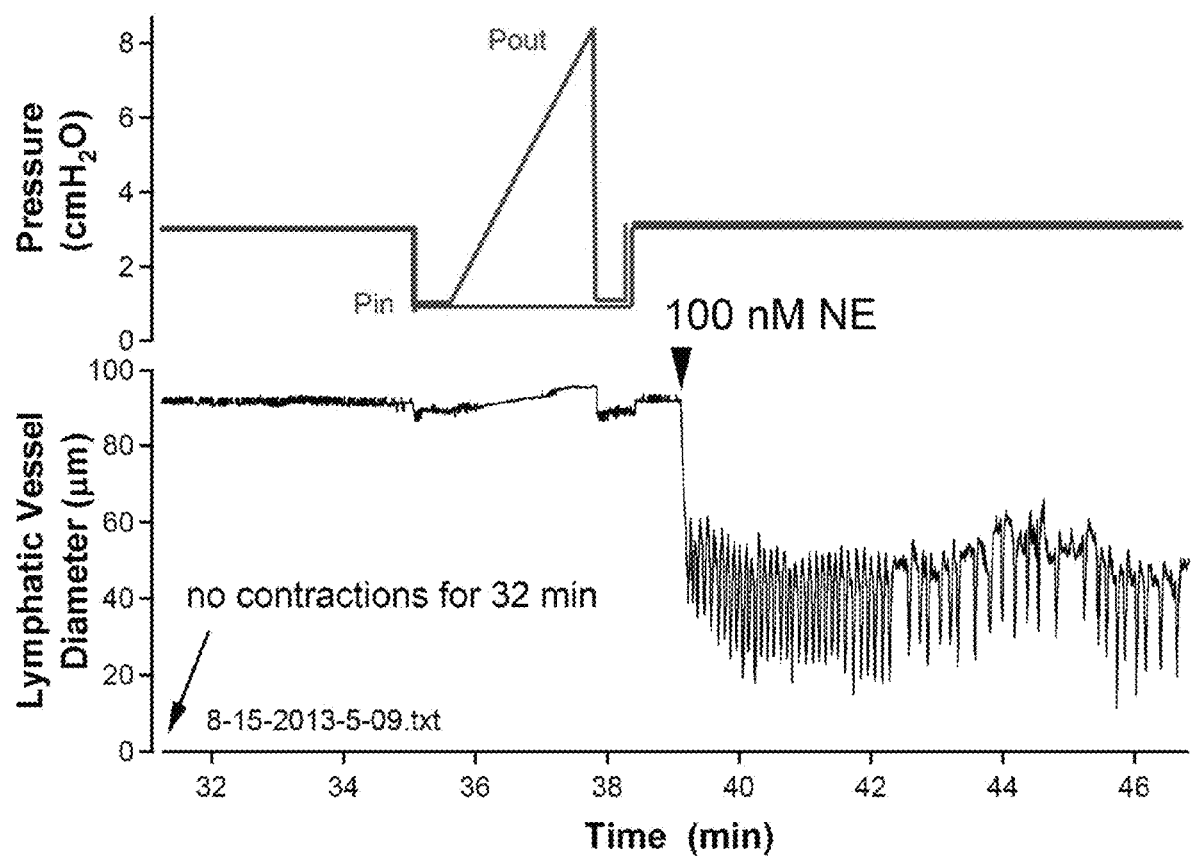
FIG. 9A, FIG. 9B, FIG. 9C and FIG. 9D depict the effect of norepinephrine (NE) on vessels with impaired contractility.
Figure 9B:
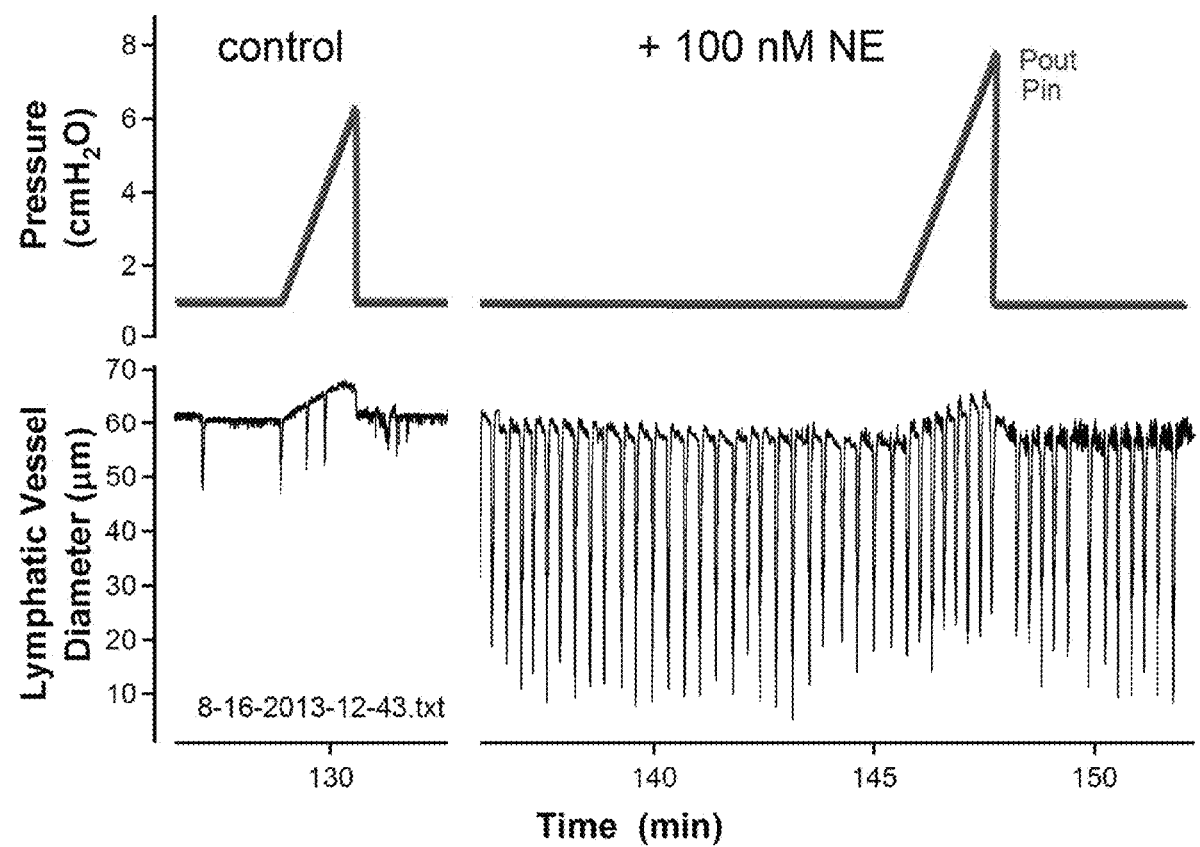
Figure 9C:
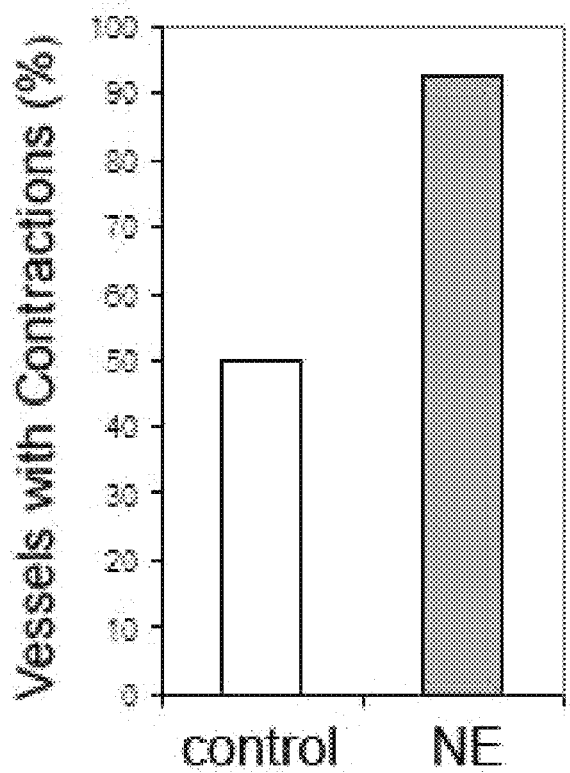
Figure 9D:
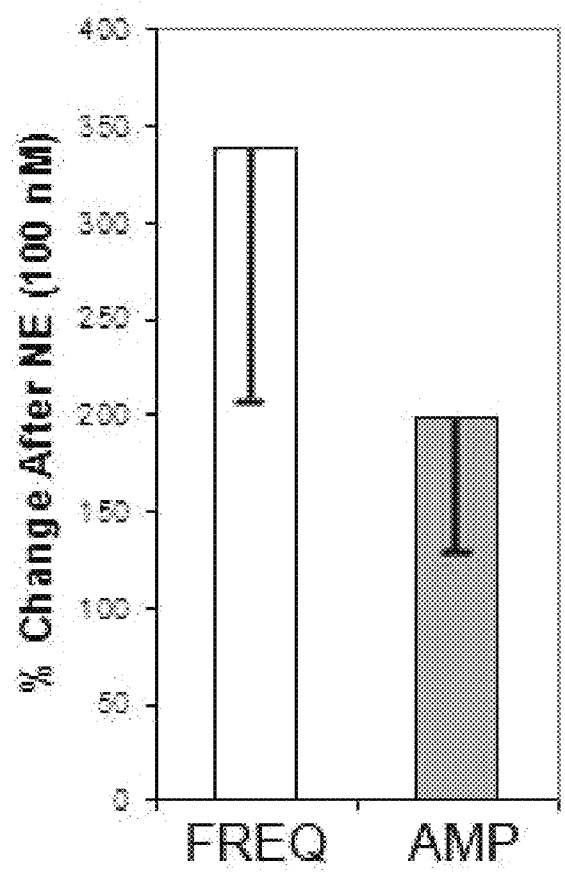

Data has been obtained to support the contention that NE has the potential not only to relieve valve lock (FIG. 3C) but also to enhance pump function. These results were obtained in another type of knock-out mouse that exhibited signs of developing hindlimb edema and therefore likely developed elevated lymphatic pressures in vivo. FIG. 9A shows how a relatively low dose of NE could induce tone and spontaneous contractions in vessels that were fatigued for prolonged periods (vessels typically begin contractions within 10 min after set-up) and did not respond to $P_{out}$, elevation. In other vessels exhibiting only weak contractions at low rates, NE induced robust contractions that persisted when pressure was elevated (FIG. 9B). Preliminary analysis of these vessels (FIG. 9C) indicates that NE doubles the likelihood of having spontaneous contractions, increasing FREQ by 3.5-fold and AMP by 2-fold. The latter observations actually underestimate the effect because they do not include 6/14 vessels without baseline activity (thus preventing comparison of the relative FREQ and AMP increases). It is presumed that NE works by enhancing inotropy under these conditions and that it may be particularly effective in vessels fatigued or in partial pump failure from chronic pressure overload.

Figure 10A:
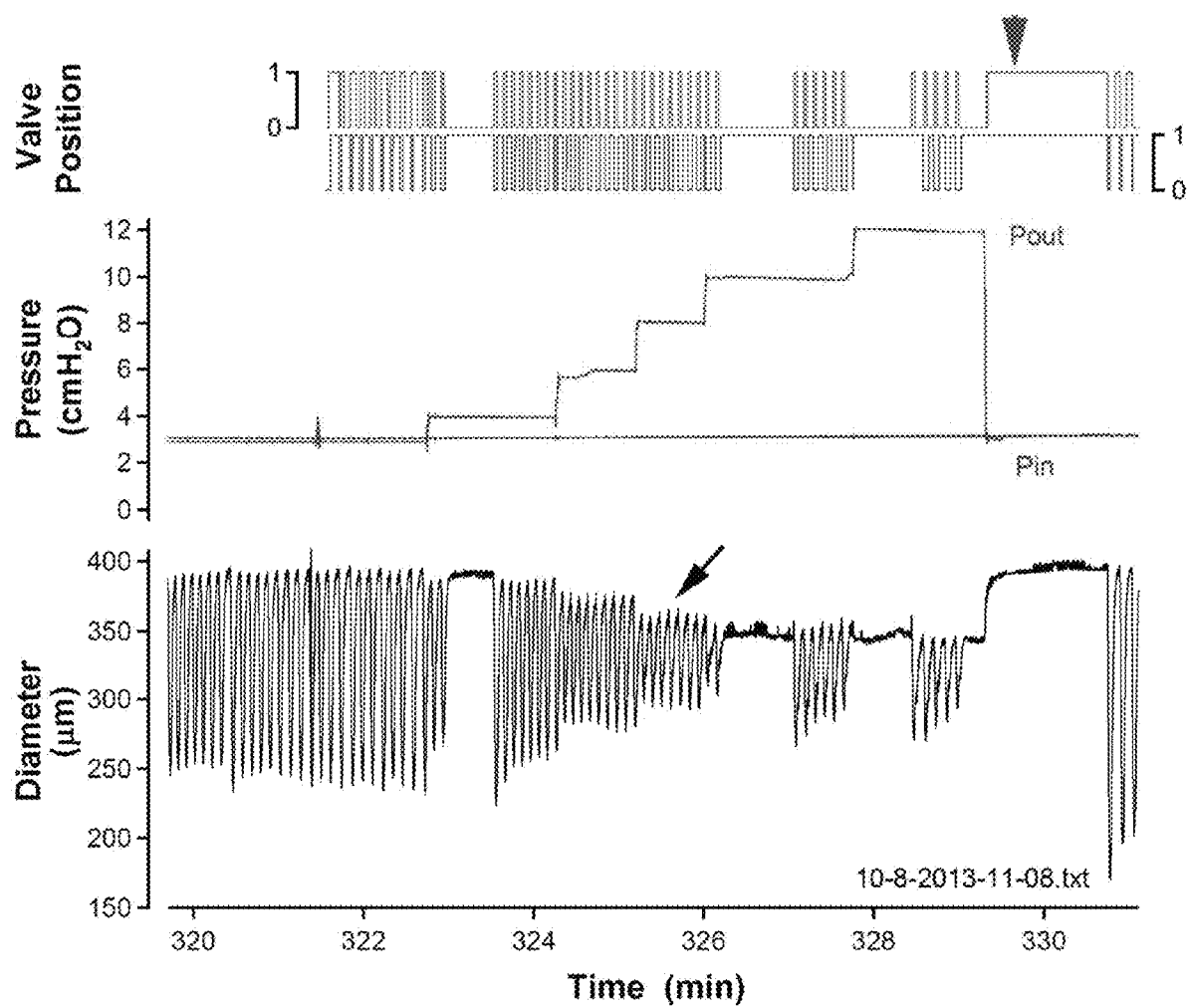
FIG. 10A and FIG. 10B depict the responses of isolated human lymphangions to $P_{out}$ elevation (FIG. 10A) and norepinephrine, NE (FIG. 10B).
Figure 10B:
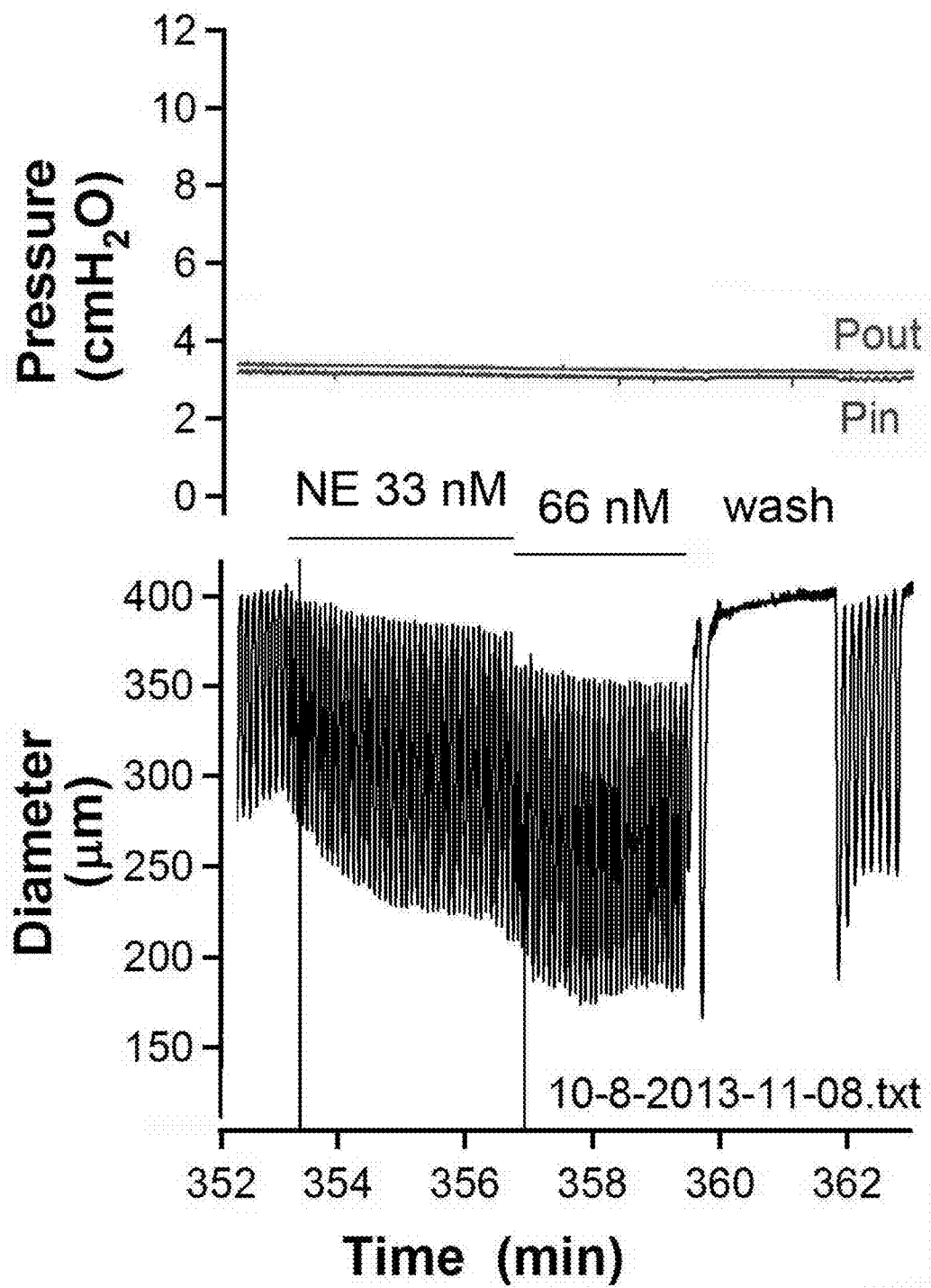
Figure 11A:
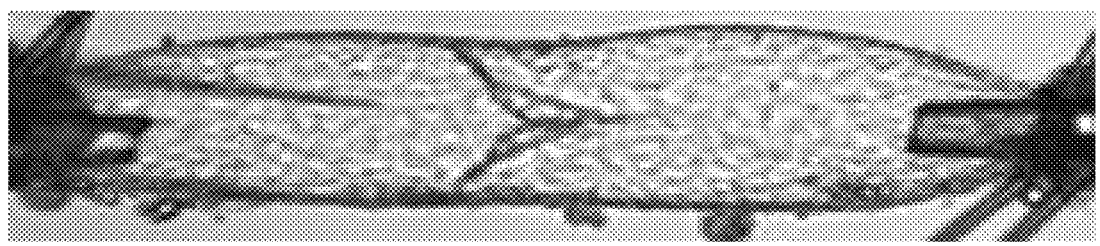
FIG. 11A, FIG. 11B, FIG. 11C and FIG. 11D depict brightfield images of valves.
Figure 11B:
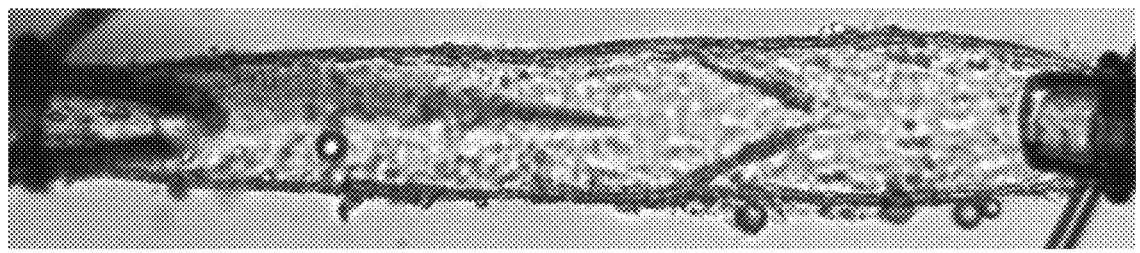
Figure 11C:
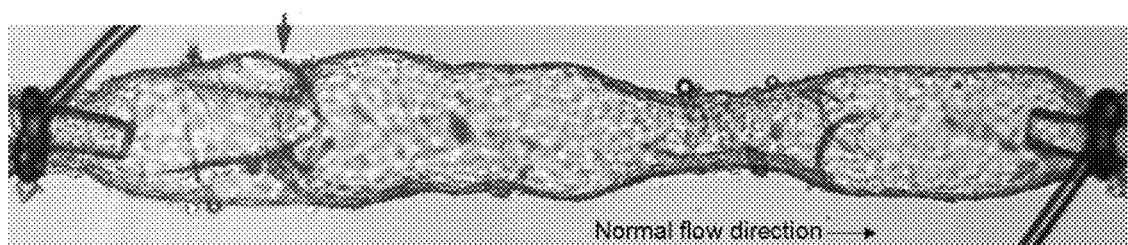
Figure 11D:
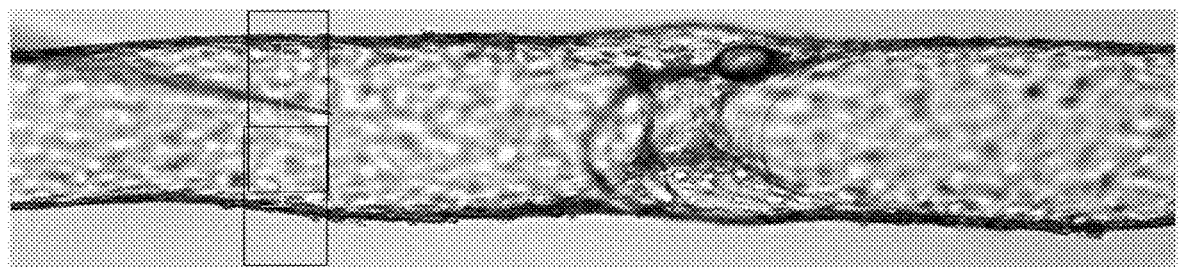

Recently, 1-, 2- and 3-valve segments of human mesenteric lymphatic vessels obtained following bariatric surgery were studied and their responses to $P_{out}$ and/or $P_{in}$ elevation and NE were tested. These are the first such measurements in isolated pressurized human lymphatics. FIG. 10 shows a progressive myogenic constriction (arrow) in a 2-valve vessel in response to $P_{out}$ elevation, which is similar to that observed in rat and mouse (FIG. 2, FIG. 5); both myogenic constriction and dilation were stronger than in the rat. The vessels were equally sensitive as rat/mouse vessels to NE, with 33 nM NE causing ~2-fold increase in FREQ and ~50% increase in AMP, as well as an increase in tone. Like rat/mouse vessels, the valves are biased to be open in the absence of a pressure gradient (arrowhead). Valve gating curves or tests for valve lock were unable to be performed because the vessels were too large to be studied on the microscope used with the pressure controller. However, it was encouraging to find that every response tested was similar to those of rat/mouse vessels.

The pump function of healthy lymphangions after they are subjected to elevated pressure for sustained periods of time will be tested. Preliminary experiments have been conducted. Popliteal pump function was assessed using configuration I, waveform I before and after 1-, 2- and 3-hr periods of elevated pressure ($P_{in}+P_{out}$=16 cmH$_2$O). The responses after the elevated pressure period were compared to those of control vessels maintained at a low pressure (2 cmH$_2$O) for the same period of time. Surprisingly, vessels maintained for 1- or 2-hrs did not show a decline, but rather a slight enhancement in pump function. However, pump function begins to decline in vessels maintained for >3 hrs. Therefore test vessels maintained for 3-, 6-, 12-, 24- and 36 hrs at elevated pressure (8-12 cmH$_2$O is more appropriate for mouse), with a 30-60 min recovery period will be tested, comparing their responses to those before sustained pressure elevation and to those of a time-control group maintained at a low pressure. The 24- and 36-hour time points will require short-term organ culture in serum-free medium (conditions in which vessels continue to function normally up to 8 days) as has been previously described[30]. It is predicted that sustained periods of elevated pressure will lead to a progressive weakening of the pump that can be at least partially restored by NE.

It was then asked can pump failure be reversed in chains of lymphangions in vivo? Once the rescue protocol has been optimized for single popliteal lymphangions, it will be applied to chains of popliteal and inguinal afferent lymphangions (configuration I) in preparation for the subsequent series of in vivo experiments. Inguinal afferent lymphatics will be used because popliteal vessels are difficult to visualize in vivo using brightfield imaging as required for micropressure measurements. Inguinal afferents show propulsive contractions similar to those of popliteal vessels, but with a more limited working pressure range (unpublished observations), perhaps because they never experience the hydrostatic loads encountered in the lower leg. The working range of inguinal vessels in vitro using configuration I will be determined, then move on to protocols that test inguinal afferent chains in vitro, then in vivo.

The first in vivo experiments will use beveled, servo-null micropipettes to measure the normal intraluminal pressure distribution from the initial lymph sacs in the dermis, through the 2-3 downstream branches, to the main inguinal afferent trunk before it enters the inguinal node. This technique has previously been used extensively in vitro and in vivo[14,17,19,22,39]. It is expected that the pressure gradient will be similar to but lower than that in rat mesentery[37], as regional vein pressures will be lower than portal venous pressure. Microvascular pressures have not been reported in any vessel of the mouse, either in the blood or lymphatic vascular system; therefore these will be the first such measurements. Nor has the pressure distribution been measured in any lymphatic tract other than the mesentery, so this information will be useful beyond the context of these studies. Outflow pressure will be elevated by controlled, partial occlusion of the large inguinal efferent tract while measuring pressure in the most proximal lymphangion of afferent chain using the servo-null micropipette; this will be repeated while measuring pressure in the second most proximal lymphangion, and so on. It is predicted that $P_{out}$ elevation to ~7 cmH$_2$O will produce pump failure and/or valve lock, as observed in preliminary in vitro experiments with inguinal afferents, and that failure/lock will then progress to the other lymphangions of the chain. When this occurs, it is expected to see the increase in outflow pressure transmitted to the most distal parts of the lymphatic trunk. Additionally, NE will be applied in the superfusate after the lymphangion(s) have failed/locked to see if it can be reversed. Once the conditions for reversing it have been worked out, NE will be injected intradermally to the skin that is drained by the inguinal afferent trunk to see if this mode of delivery is effective at treating pump failure. By doing this, the lymphatic system to drain lymph from a large surface area and collect it through a single outflow vessel will be taken advantage of, thereby confining side-effects on blood vessels to a local area.

Further, it was asked can Foxc2$^{+/-}$, Foxc2$^{-/-}$ vessels be rescued in vitro and in vivo? The most effective NE treatment regime will be tested on Foxc2$^{+/-}$ and Foxc2$^{-/-}$ vessels. The first protocols will be conducted in single Foxc2$^{+/-}$ popliteal lymphangions, then applied to chains of Foxc2$^{+/-}$ popliteal lymphangions (configuration I). The studies then will be repeated on vessels from Foxc2$^{-/-}$ mice treated for 2 or 4 wks with tamoxifen. Based on preliminary data (FIG. 5, FIG. 6, FIG. 7), it is likely that vessels from both types of Foxc2-deficient mice will fail/lock at lower pressures than their respective controls. Once the conditions under which Foxc2-deficient vessels can be rescued in vitro are determined, the in vivo protocols on Foxc2$^{+/-}$ and Foxc2$^{-/-}$ vessels will be repeated. It is not expected that dysfunctional pumping in Foxc2-deficient vessels can be completely rescued; rather it is expected that treatment with NE will 1)

increase the chance of closure of partially-functional valves at low pressures, and 2) partially compensate, with increased inotropy, for dysfunctional valves.

Figure 18A:
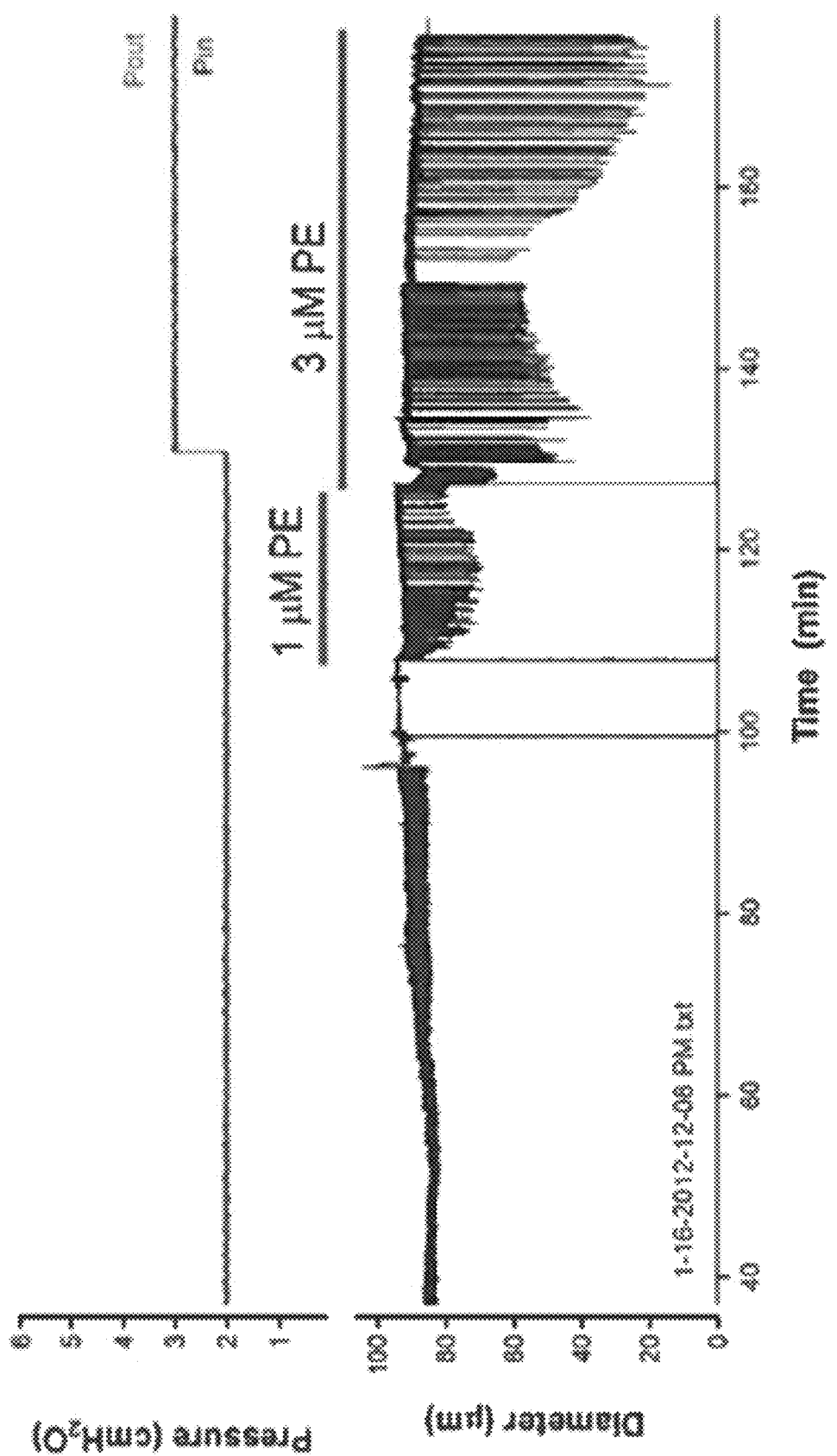
FIG. 18A and FIG. 18B depict graphs illustrating that the application of phenylephrine (PE) to a mouse diseased tissue sample improves/restores normal contractions and pumping functions.
Figure 18B:
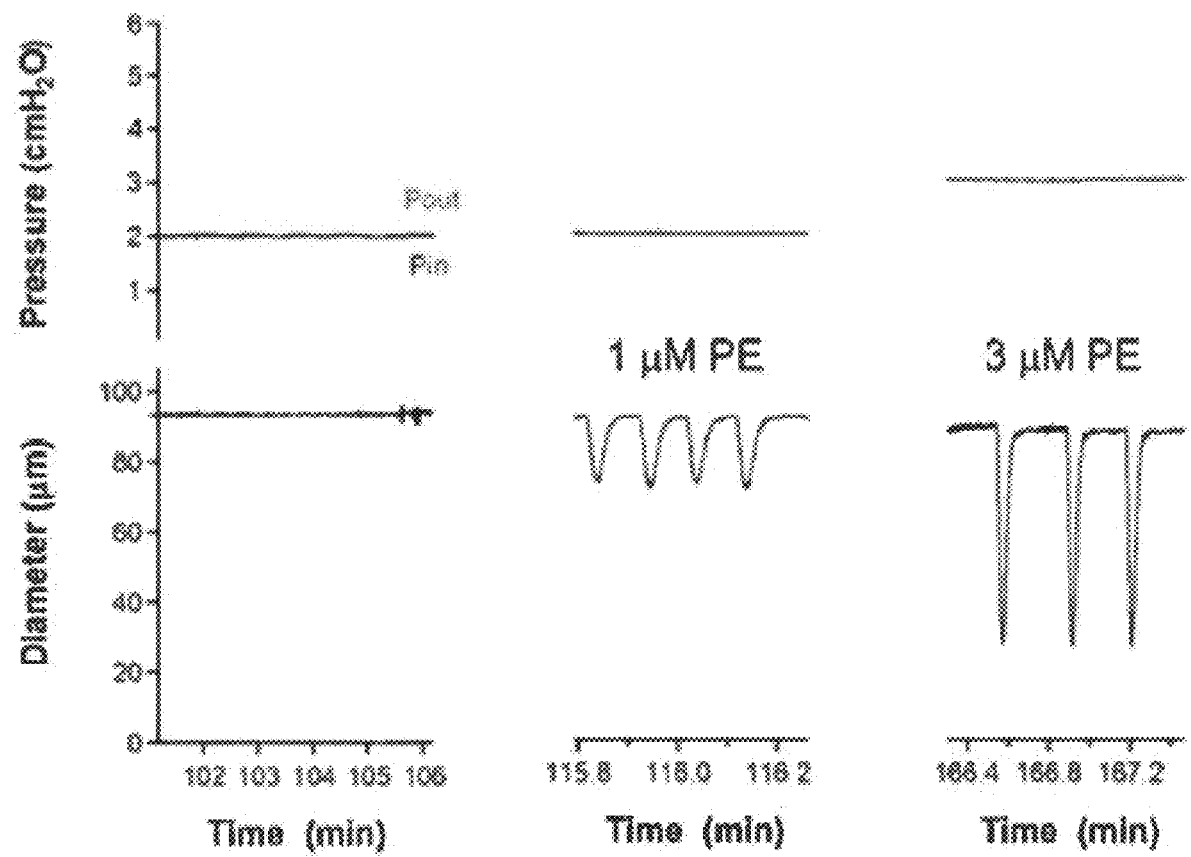

Example 5. Evaluation of Additional Agents to Rescue Pump Dysfunction in Lymphatic Vessels As shown herein, norepinephrine (NE) restores contraction and pumping in dysfunctional lymphatic vessels. NE is an α1- and α2-adrenergic agonist. To further confirm the activity of alpha-adrenergic agonists on restoration of lymphatic vessel pumping, phenylephrine (PE) was tested on a mouse vessel via the methods described herein. PE is a selective α1-adrenergic agonist. PE also restored contraction and pumping in dysfunctional lymphatic vessels (FIG. 18), further validating that alpha-adrenergic agonists are effective in rescuing pump dysfunction.

Figure 19:
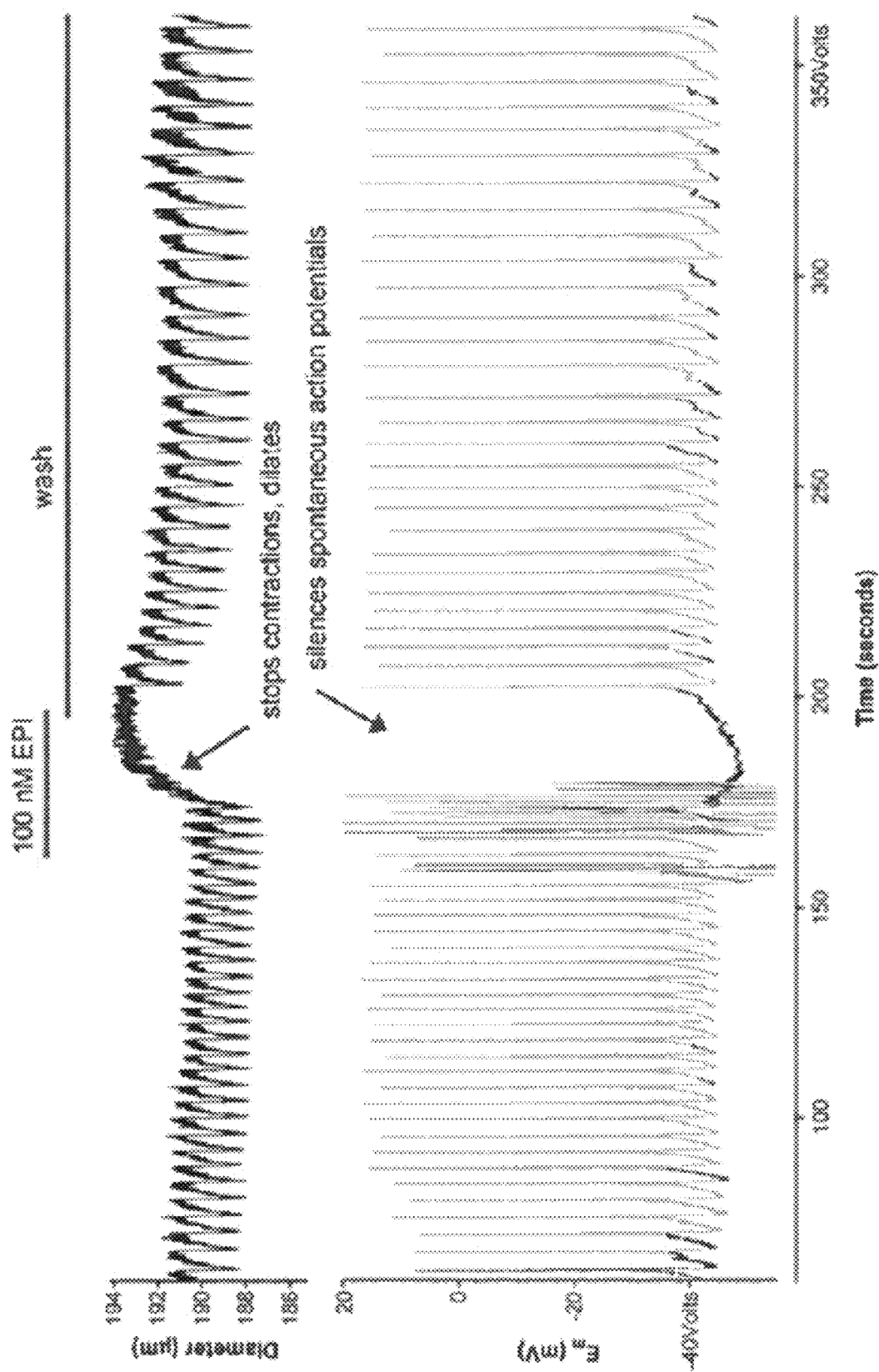
FIG. 19 depicts a graph illustrating that application of epinephrine (EPI) to a rat normal tissue sample stops normal contractions.

The effect of ephinephrine (EPI) on a rat vessel was also evaluated. The application of EPI to the rat vessel stopped normal contractions (FIG. 19). EPI is a non-selective α- and β-adrenergic agonist. Accordingly, these results demonstrate that β-adrenergic agonists hinder the restoration of lymphatic pump dysfunction.

Figure 20:
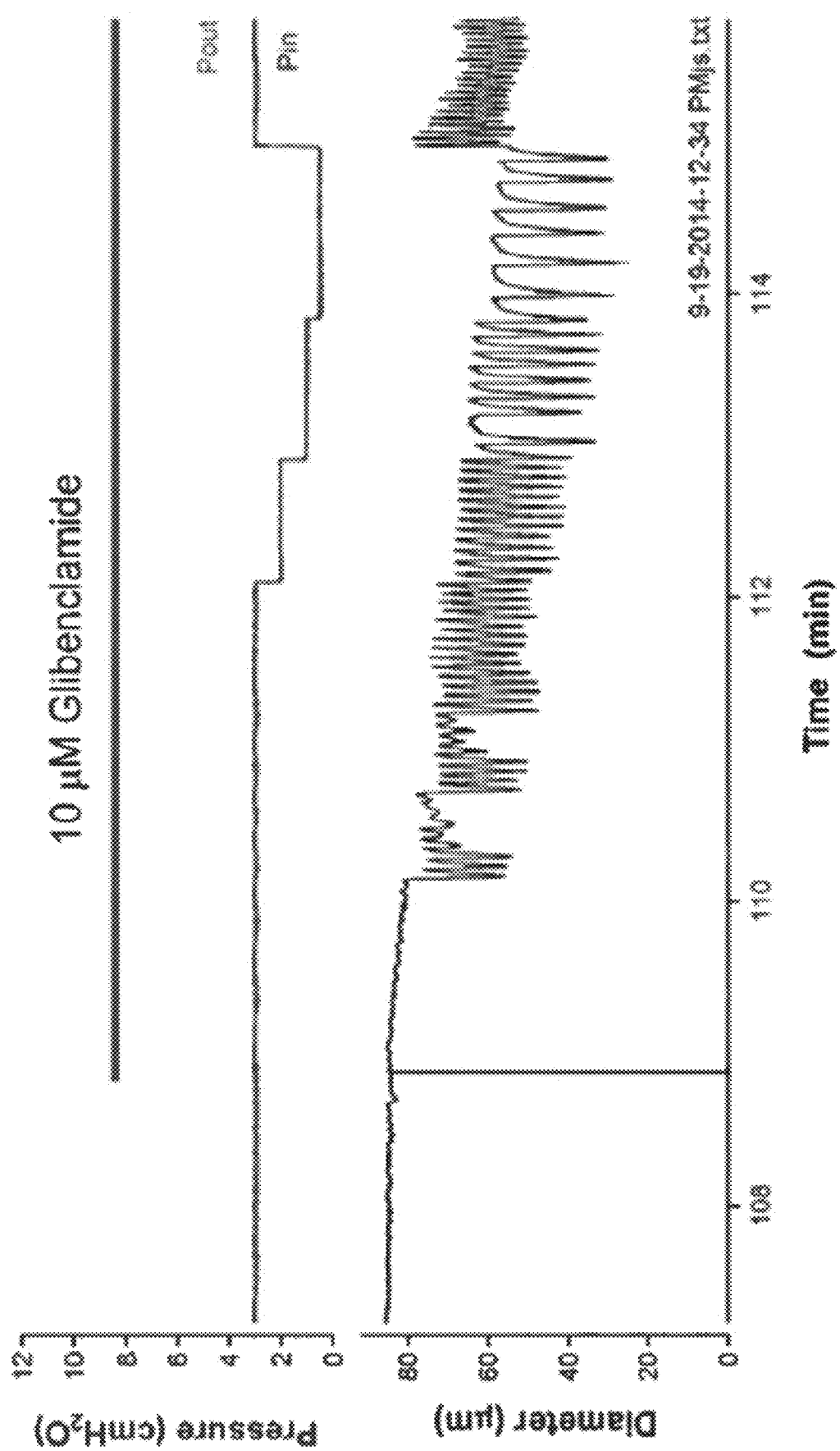
FIG. 20 depicts a graph illustrating that application of glibenclamide to a mouse diseased tissue sample improves/restores normal contractions and pumping functions.
Figure 21:
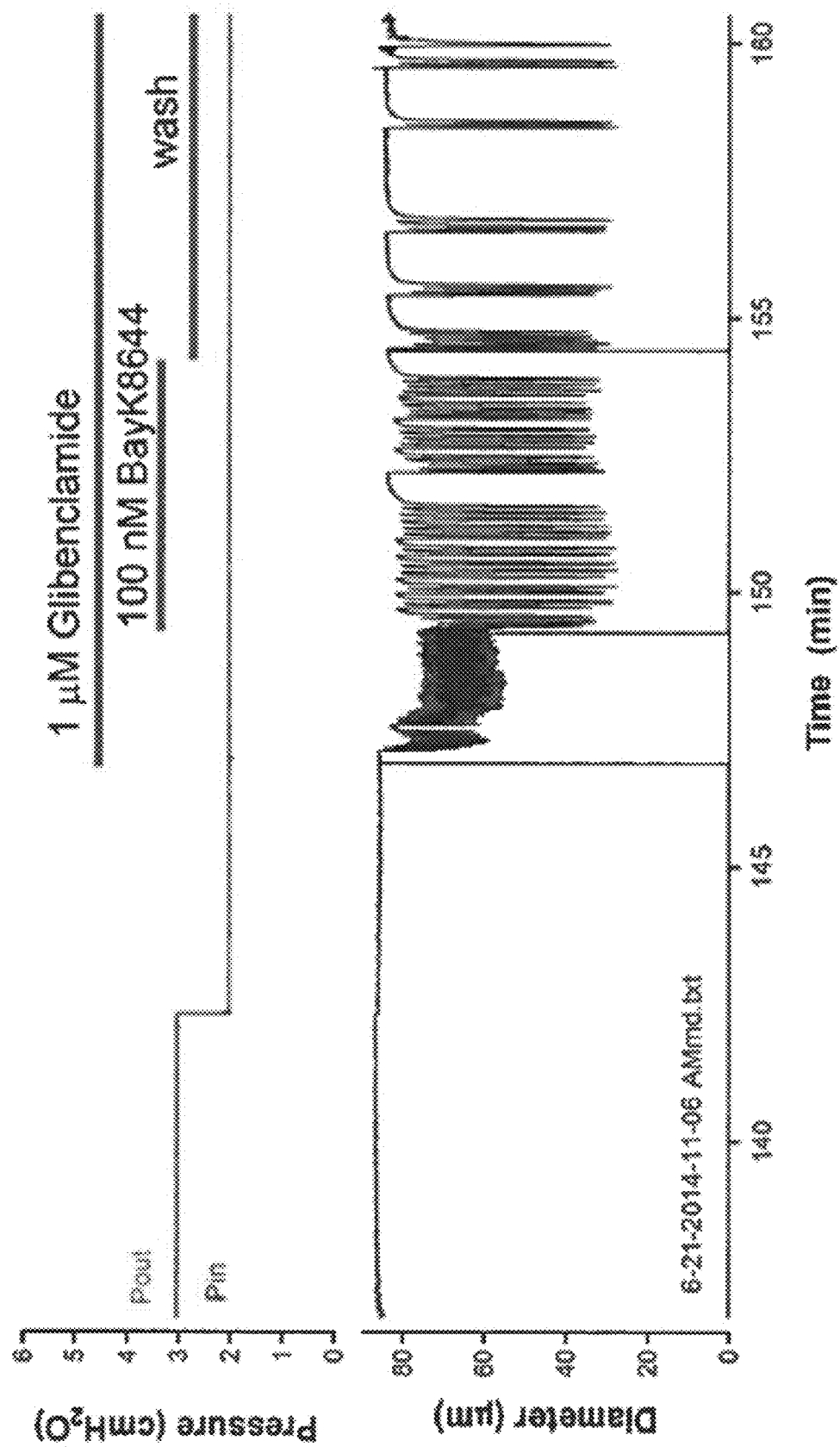
FIG. 21 depicts a graph illustrating that application of glibenclamide and BayK8644 in combination to a mouse diseased tissue sample improves/restores normal contractions and pumping functions.

Glibendamide was then applied to a disease mouse tissue sample. FIG. 20 demonstrates that gibenclamide improves/restores normal contractions and pumping functions. Glibendamide is an exemplary KATP channel inhibitor, thus this result indicates that KATP channel inhibitors have beneficial effects on improving/restoring contractions and pumping in dysfunctional lymphatic vessels. The combination of glibenclamide and BayK8644 was then evaluated in a diseased mouse tissue sample. FIG. 21 demonstrates that the combination of glibenclamide and BayK8644 improves/restores normal contractions and pumping functions. BayK8644, along with BayR5417 and FPL64176, are exemplary L-type calcium channel agonists. Thus, these results indicate that L-type calcium channel agonists alone or in combination with KATP channel inhibitors may have beneficial effects on improving/restoring contractions and pumping in dysfunctional lymphatic vessels.

Methods for Examples 1-5

In Vivo Methods.

Of the multiple afferents to the inguinal nodes in the mouse[79], the one draining the dermis of the lateral flank is particularly accessible. After making a midline incision down the back and retracting the skin to the side, ~1 cm of the lymphatic trunk is visible running along the associated artery/vein pair in loose connective tissue between the skin and the inguinal fat pad. The inguinal afferent has 4-5 valves over this length and its upstream branches can be traced all the way back to initial lymphatic sacs in the dermis. The principal efferent tract from the node is a large lymphatic trunk running parallel to the epigastric vein/artery toward the axillary nodes[79]. Under anesthesia, the afferent inguinal lymphatic will be exteriorized and the skin flap that it drains will be pinned to a Sylgard support platform. The vessel will be visualized by transillumination using a light pipe on a Zeiss ACM upright microscope[18,19] while the preparation is superfused with Krebs buffer at 37° C. Output pressure will be elevated by partial ligation of the large inguinal efferent tract using a loop of 10-0 suture approximately 1-2 cm downstream from the inguinal node-similar to the method developed to raise venous pressure in mesenteric arcades in vivo[17].

Assessment of Valve Structure.

The structure of lymphatic valves in normal, Foxc2$^{+/-}$ and Foxc2$^{-/-}$ vessels will be analyzed using procedures described in detail[54,60,66]. After determination of output valve function, the vessels will be fixed and immunostained for ECM proteins known to be important for valve structure (collagen IV, laminin-α5, integrin α9) to test whether deficiencies correlate to functional deficits. The muscle layer will be delineated using a SMA or SMMHC antibody. The structure of the valves (e.g. leaflet and buttress lengths) will be determined post-experimentally (from delineation of the endothelial cell borders by mOrange fluorescence driven by Prox1 promoter, which has been inserted in the inducible Foxc2$^{-/-}$ and Foxc2$^{flox/flox}$ strains) in cannulated vessels by z-axis sectioning and 3D reconstruction using confocal microscopy, as described previously[12,21].

Contraction Wave Synchrony.

Figure 12A:
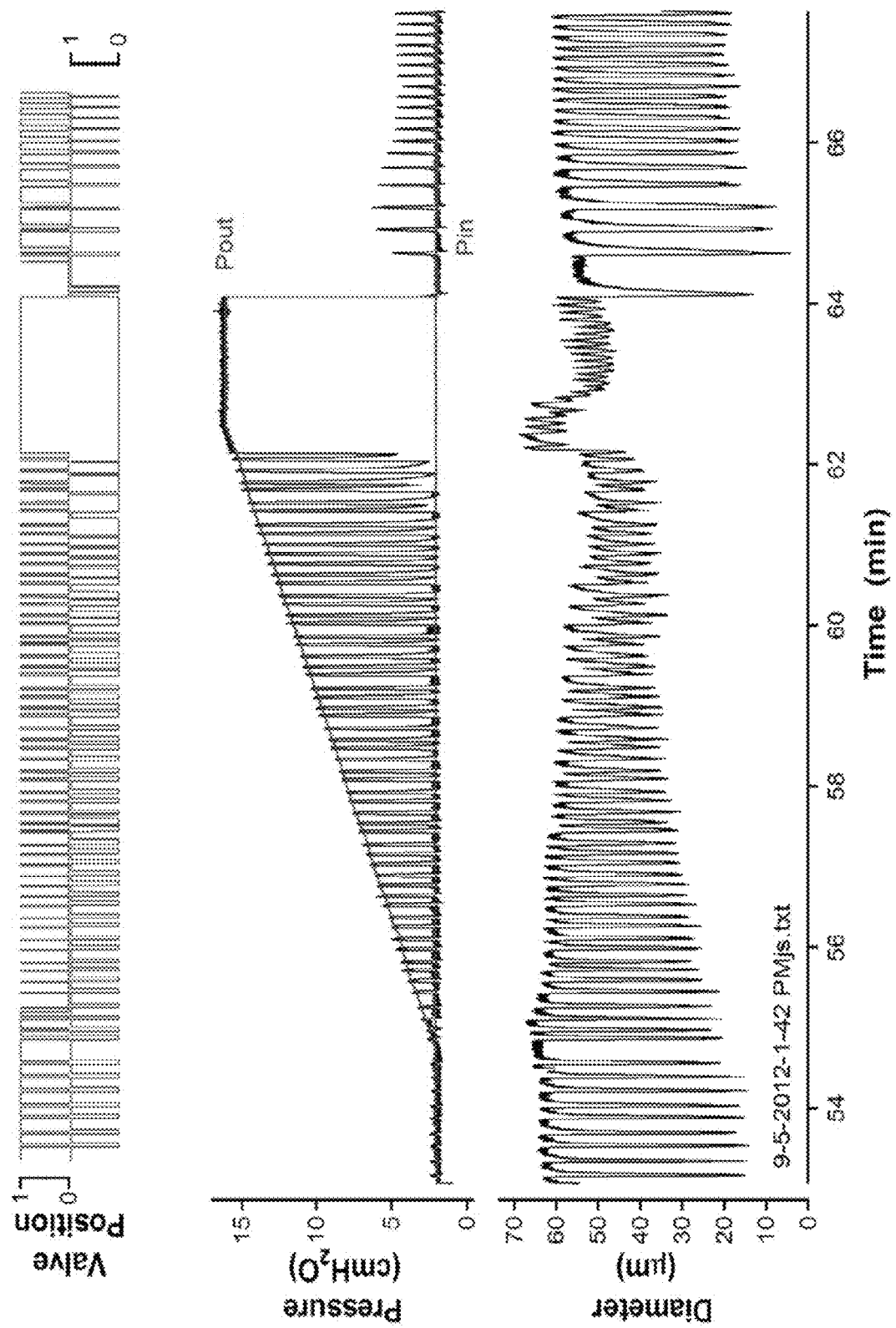
FIG. 12A depicts the conventional diameter and pressure recordings of a mouse popliteal lymphangion subjected to a $P_{out}$ ramp and eventually undergoing valve lock at t=62 min.
Figure 12B:
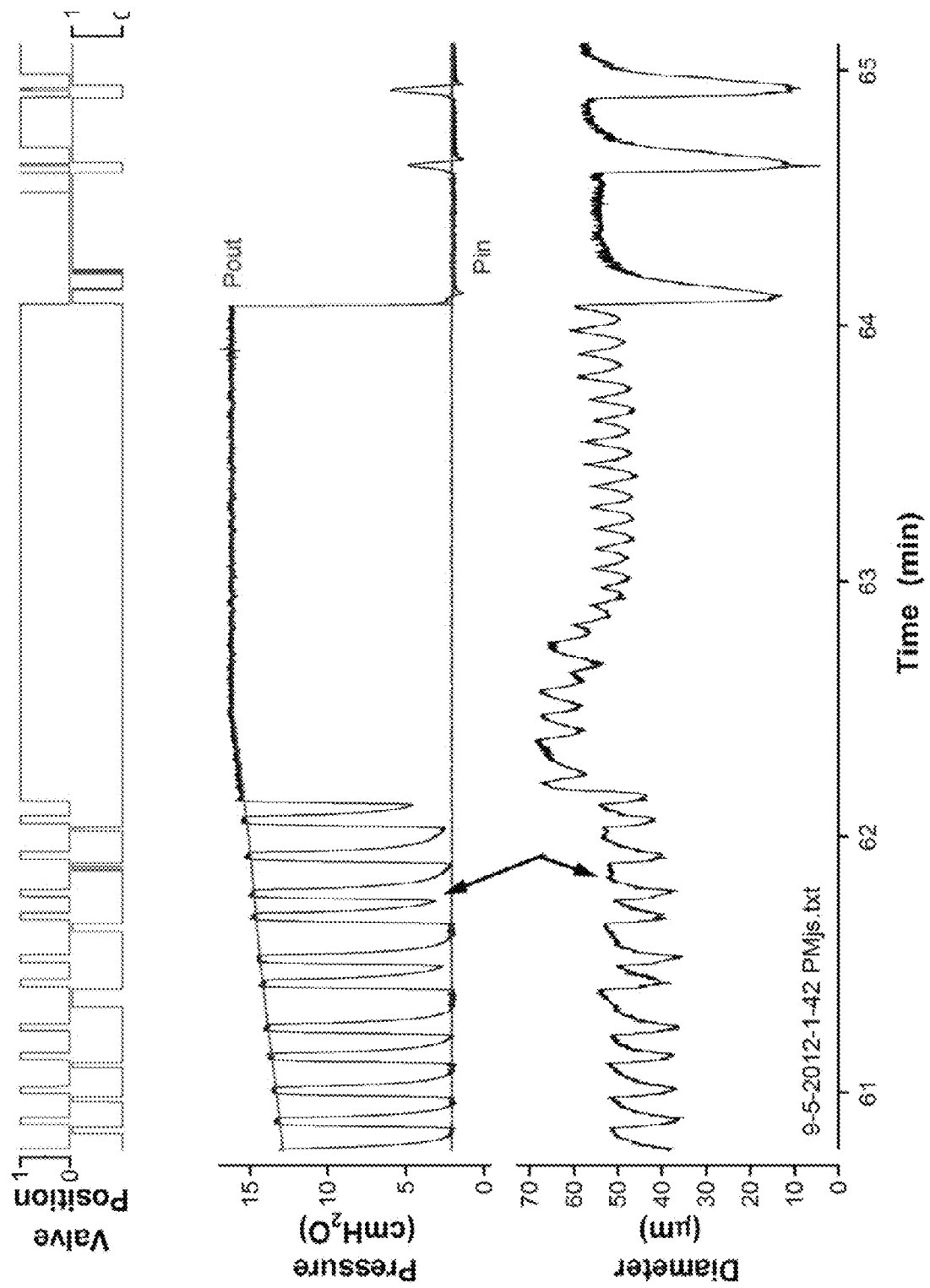
FIG. 12B depicts an expanded time scale of FIG. 12A.
Figure 12C:
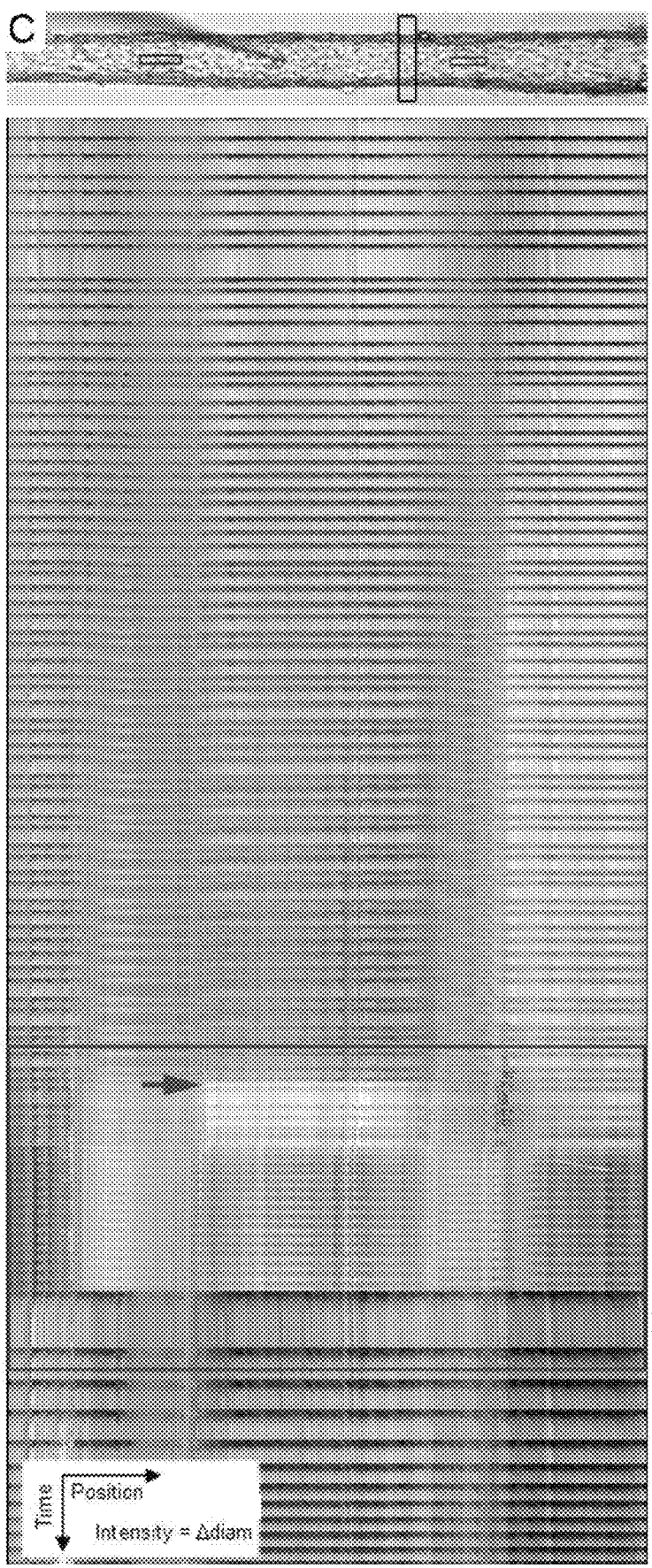
FIG. 12C depicts a space-time (ST) map which provides information about every region along the vessel at every time point. Each horizontal line corresponds to one contraction, with intensity indicating contraction magnitude (horizontal pixels in FIG. 12C are aligned to the vessel image at top). Contractions start at the input valve and proceed to the right. Valve lock occurs at the red arrow (white indicates dilation).
Figure 12D:
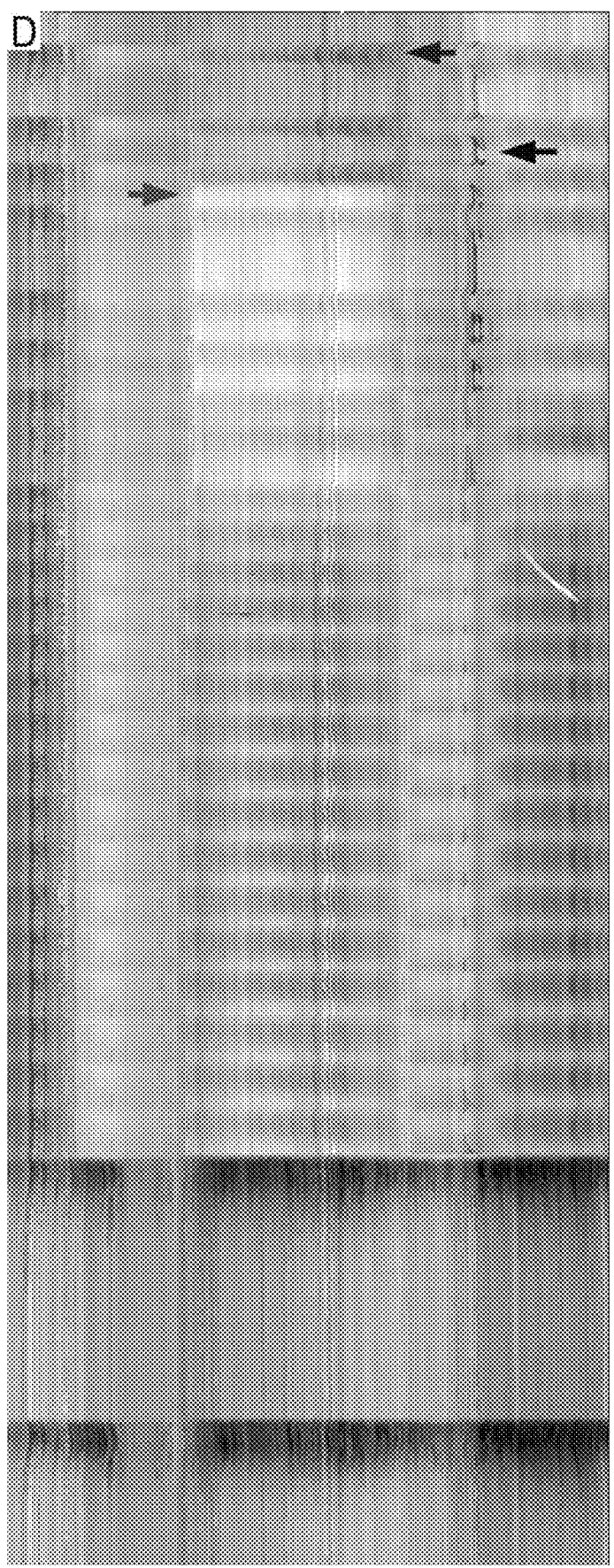
FIG. 12D depicts an enlarged view of the area demarcated by the red box in FIG. 12C.
Figure 13A:
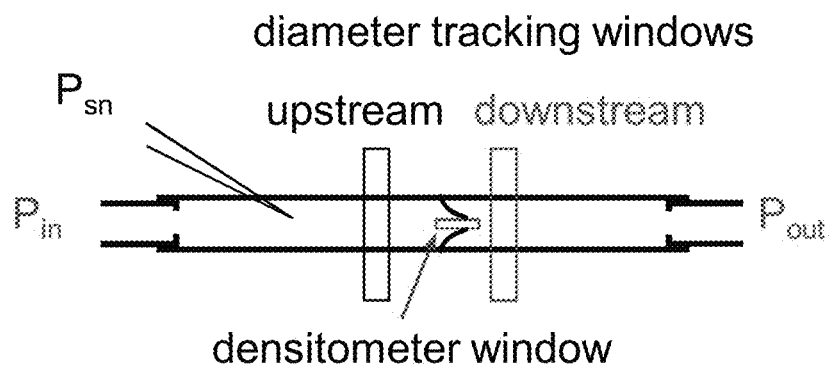
FIG. 13A, FIG. 13B, FIG. 13C and FIG. 13D depict graphs showing that valve closure is passive but depends on diameter.
Figure 13B:
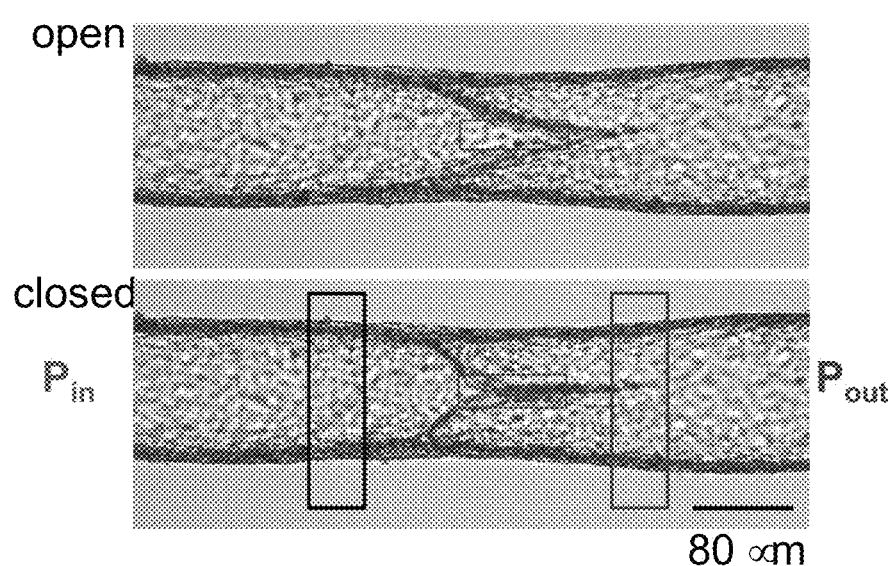
Figure 13C:
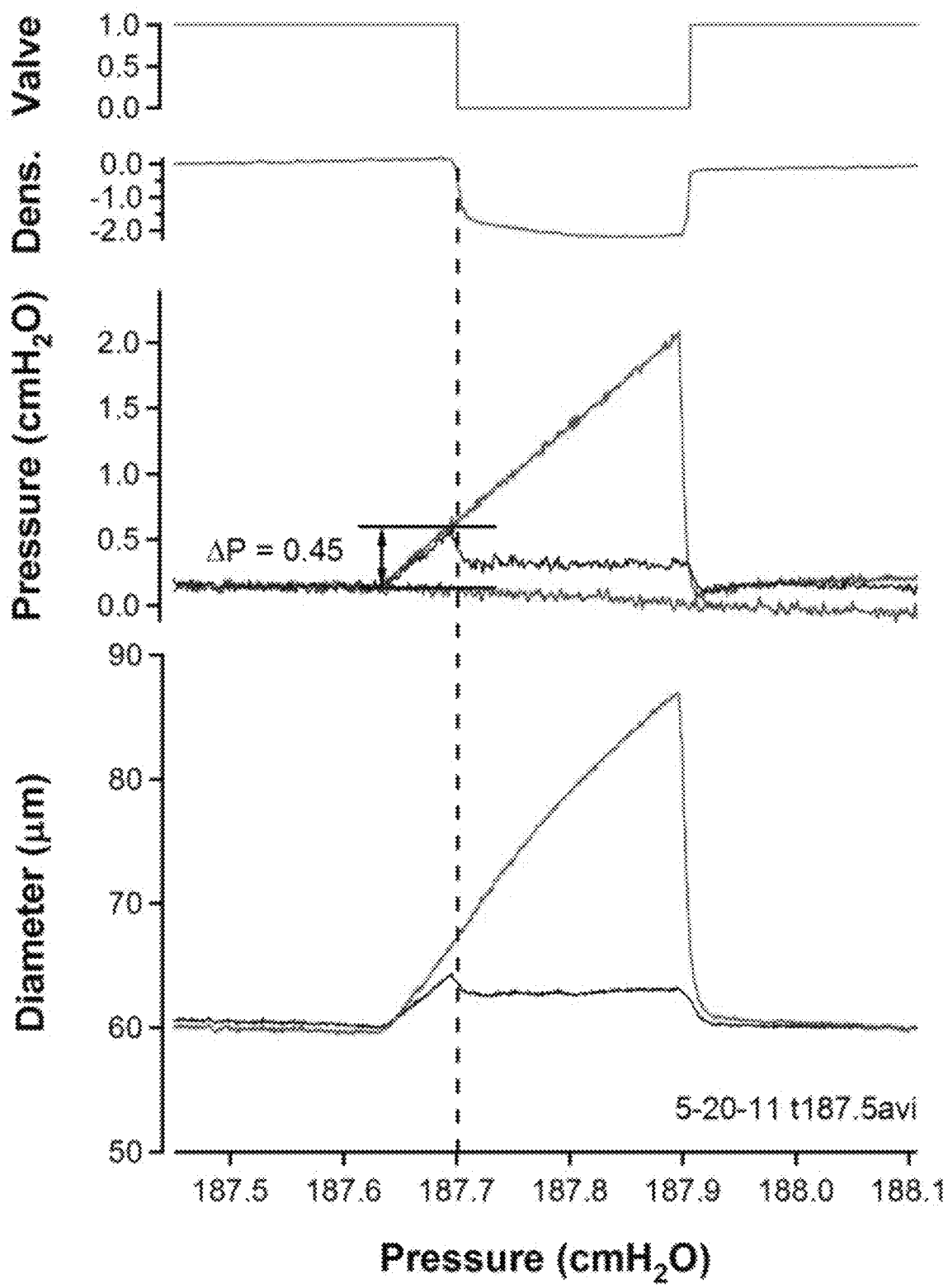
Figure 13D:
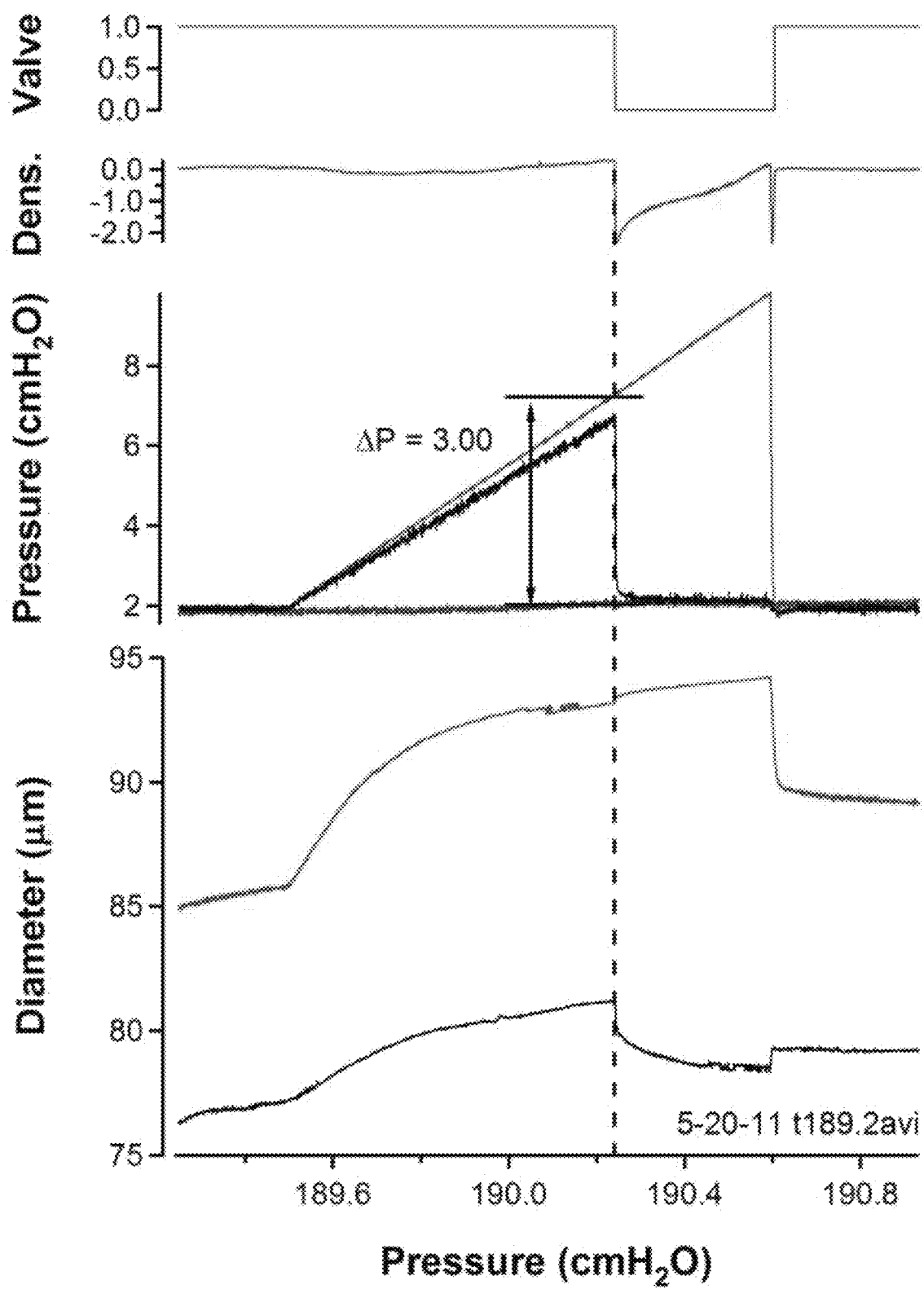

Sophisticated analyses to quantify the diameter changes at each point along the lymphangion, and measure direction, velocity and synchronization of the contraction wave before and after a vessel is challenged with a pressure load has been developed. An example of the preliminary analysis is shown in FIG. 12. Conventional diameter and pressure recordings of a mouse popliteal lymphangion subjected to a $P_{out}$ ramp and eventually undergoing valve lock at t=62 min are shown in FIG. 12A (FIG. 12B=expanded time scale). FIG. 12C: A space-time (ST) map provides information about EVERY region along the vessel at EVERY time point. Each horizontal line corresponds to one contraction, with intensity indicating contraction magnitude (horizontal pixels in FIG. 12C are aligned to the vessel image at top). Contractions start at the input valve and proceed to the right. Valve lock occurs at the red arrow (white indicates dilation). FIG. 12D is an enlarged view of the area demarcated by the red box in FIG. 12C. Valve lock is preceded by a change in the direction of the contraction wave (blue arrow), as indicated by bending of the intensity wavefront to the left. There is also a small, focal contraction of a segment on the output side of the valve (black arrow). Whether these events are consistent between vessels remains to be determined. However, this analysis provides proof of principle that efficient pumping depends critically on synchronized contractions within the lymphangion. These methods will be used to analyze the direction, coordination and velocity of WT and Foxc2$^{+/-}$,$^{-/-}$-contraction waves prior to and during valve lock.

Statistical Analyses.

Power analyses were used to predict reasonable sample sizes for each protocol at alpha=0.05. Given the variation inherent in these specific types of measurements, 8-12 successful experiments are required for each protocol. When possible, ANOVAs with post-hoc tests will be used as appropriate if the data are normally distributed. The specific test is difficult to predict in advance for each protocol but examples would be 1-way ANOVAs for the data sets in FIG. 6C and 1-way repeated measures ANOVAs for data in FIG. 7A, FIG. 7B.

REFERENCES FOR THE EXAMPLES

1. Armer J M. The problem of post-breast cancer lymphedema: impact and measurement issues. *Cancer Investigation* 1: 76-83, 2005.
2. Aukland K, and Reed R K. Interstitial-lymphatic mechanisms in the control of extracellular fluid volume. *Physiol Rev* 73: 1-78, 1993.

3. Bates D O, Levick J R, and Mortimer P S. Starling forces in the human arm and their alteration in postmastectomy oedema. *Journal of Physiology* 477: 355-363, 1994.
4. Bates D O, Levick J R, and Mortimer P S. Subcutaneous interstitial fluid pressure and arm volume in lymphoedema. *Int J Microcirc Clin Exp* 11: 359-373, 1992.
5. Bazigou E, Xie S, Chen C, Weston A, Miura N, Sorokin L, Adams R, Muro A F, Sheppard D, and Makinen T. Integrin-alpha9 is required for fibronectin matrix assembly during lymphatic valve morphogenesis. *Developmental Cell* 17: 175-186, 2009.
6. Beckett E A, Hollywood M A, Thornbury K D, and McHale N G. Spontaneous electrical activity in sheep mesenteric lymphatics. *Lymphatic Research & Biology* 5: 29-43, 2007.
7. Benoit J N, Zawieja D C, Goodman A H, and Granger H J. Characterization of intact mesenteric lymphatic pump and its responsiveness to acute edemagenic stress. *American Journal of Physiology (Heart and Circulatory Physiology)* 257: H2059-H2069, 1989.
8. Bertram C D, Macaskill C, and Moore J E. Simulation of a chain of collapsible contracting lymphangions with progressive valve closure. *Biomech Model Mechanobiol* June 26 Epub, 2013.
9. Brice G, Child A H, Evans A, Bell R, Mansour S, Bumand K, Sarfarazi M, Jeffery S, and Mortimer P. Milroy disease and the VEGFR-3 mutation phenotype. *Journal of Medical Genetics* 42: 98-102, 2005.
10. Brice G, Mansour S, Bell R, Collin J R O, Child A H, Brady A F, Sarfarazi M, Bumand K G, Jeffery S, Mortimer P S, and Murday V A. Analysis of the phenotypic abnormalities in lymphoedema-distichiasis syndrome in 74 patients with FOXC2 mutations or linkage to 16q24. *Journal of Medical Genetics* 39: 478-483, 2002.
11. Chen H I, Granger H J, and Taylor A E. Interaction of capillary, interstitial, and lymphatic forces in the canine hindpaw. *Circulation Research* 39: 245-254, 1976.
12. Clifford P S, Ella S R, Stupica A J, Nourian Z, Li M, Martinez-Lemus L A, Dora K A, Yang Y, Davis M J, Pohl U, Meininger G A, and Hill M A. Spatial distribution and mechanical function of elastin in resistance arteries: a role in bearing longitudinal stress. *Arterioscler Thromb Vasc Biol* 31: 2889-2896, 2011.
13. Clough G, and Smaje L H. Simultaneous measurement of pressure in the interstitium and the terminal lymphatics of the cat mesentery. *Journal of Physiology* 283: 457-468, 1978.
14. Davis M J. Control of bat wing capillary pressure and blood flow during reduced perfusion pressure. *American Journal of Physiology (Heart and Circulatory Physiology)* 255: H1114-H1129, 1988.
15. Davis M J. An improved, computer-based method to automatically track internal and external diameter of isolated microvessels. *Microcirculation* 12: 361-372, 2005.
16. Davis M J, Davis A M, Ku C W, and Gashev A A. Myogenic constriction and dilation of isolated lymphatic vessels. *American Journal of Physiology (Heart and Circulatory Physiology)* 296: H293-H302, 2009.
17. Davis M J, and Gore R W. Capillary pressures in rat intestinal muscle and mucosal villi during venous pressure elevation. *American Journal of Physiology (Heart and Circulatory Physiology)* 249: H174-H187, 1985.
18. Davis M J, and Gore R W. A new preparation for microcirculatory studies of the hamster cheek pouch. *American Journal of Physiology (Heart and Circulatory Physiology)* 248: H143-H146, 1985.
19. Davis M J, Joyner W L, and Gilmore J P. Microvascular pressure distribution and responses of pulmonary allografts and cheek pouch arterioles in the hamster to oxygen. *Circulation Research* 49: 125-132, 1981.
20. Davis M J, Lane M M, Davis A M, Durtschi D, Zawieja D C, Muthuchamy M, and Gashev A A. Modulation of lymphatic muscle contractility by the neuropeptide substance P. *American Journal of Physiology (Heart and Circulatory Physiology)* 295: H587-H597, 2008.
21. Davis M J, Rahbar E, Gashev A A, Zawieja D C, and Moore J E. Determinants of valve gating in collecting lymphatic vessels from rat mesentery. *American Journal of Physiology (Heart and Circulatory Physiology)* 301: H48-H60, 2011.
22. Davis M J, Scallan J P, Wolpers J H, Muthuchamy M, Gashev A A, and Zawieja D C. Intrinsic increase in lymphatic muscle contractility in response to elevated afterload. *American Journal of Physiology (Heart and Circulatory Physiology)* 303: H795-H808, 2012.
23. Drake R E, and Gabel J C. Effect of outflow pressure on intestinal lymph flow in unanesthetized sheep. *American Journal of Physiology (Regulatory, Integrative and Comparative Physiology)* 260: R668-R671, 1991.
24. Eisenhoffer J, Kagal A, Klein T, and Johnston M G. Importance of valves and lymphangion contractions in determining pressure gradients in isolated lymphatics exposed to elevations in outflow pressure. *Microvasc Res* 49: 97-110, 1995.
25. Engeset A, Olszewski W, Jaeger P M, Sokolowski J, and Theodorsen L. Twenty-four hour variation in flow and composition of leg lymph in normal men. *Acta Physiol Scandinavica* 99: 140-148, 1977.
26. Fang J M, Dagenais S L, Erickson R P, Art M F, Glynn M W, Gorski J L, Seaver L H, and Glover T W. Mutations in FOXC2 (MFH-1), a forkhead transcription factor, are responsible for the hereditary lymphedema-distichiasis syndrome. *American Journal of Human Genetics* 67: 1382-1387, 2000.
27. Finegold D N, Kimak M A, Lawrence E C, Levinson K L, Chemiske E M, Pober B R, Dunlap J W, and Ferrell R E. Truncating mutations in FOXC2 cause multiple lymphedema syndromes. *Human Molecular Genetics* 10: 1185-1189, 2001.
28. Foldi M. Physiology and pathophysiology of lymph flow. In: Lymphedema, edited by Clodius L. Stuttgart: Georg Thieme Publishers, 1977, p. 1-11.
29. Foldi M. Role of the lymph circulation in congestive heart failure. *Japanese Circulatory Journal* 25: 703, 1961.
30. Gashev A, Davis M J, Gasheva O Y, Nepiushchikh Z V, Wang W, Dougherty P, Kelly K A, Cai S, Von der Weid P Y, Muthuchamy M, Meininger C J, and Zawieja D C. Methods for lymphatic vessel culture and gene transfection. *Microcirculation* 16: 615-628, 2009.
31. Gashev A A, Davis M J, and Zawieja D C. Inhibition of the active lymph pump by flow in rat mesenteric lymphatics and thoracic duct. *Journal of Physiology* 450: 1023-1037, 2002.
32. Goldman J, Conley K A, Raehl A, Bondy D M, Pytowski B, and Swartz M A. Regulation of lymphatic capillary regeneration by interstitial flow in skin. *American Journal of Physiology (Heart and Circulatory Physiology)* 292: H2176-H2183, 2007.
33. Greene A K, Grant F D, and Slavin S A. Lower-extremity lymphedema and elevated body-mass index. *New England Journal of Medicine* 366: 2136-2137, 2012.
34. Hagendoom J, Padera T P, Kashiwagi S, Isaka N, Noda F, Lin M I, Huang P L, Sessa W C, Fukumura D, and Jain R K. Endothelial nitric oxide synthase regulates microlymphatic flow via collecting lymphatics. *Circ Res* 95: 204-209, 2004.
35. Hargens A R, Millard R W, Pettersson K, and Johansen K. Gravitational haemodynamics and oedema prevention in the giraffe. *Nature* 329: 59-60, 1987.
36. Hargens A R, and Zweifach B W. Contractile stimuli in collecting lymph vessels. *American Journal of Physiology (Heart and Circulatory Physiology)* 233: H57-H65, 1977.
37. Hargens A R, and Zweifach B W. Transport between blood and peripheral lymph in intestine. *Microvascular Research* 11: 89-101, 1976.
38. Iida K, Koseki H, Kakinuma H, Kato N, Mitzutani-Koseki Y, Ohuchi H, Yoshioka H, Noji S, Kawamura K, Kataoka Y, Ueno F, Taniguchi M, Yoshida N, Sugiyama T, and Miura N. Essential roles of the winged helix transcription factor MFH-1 in aortic arch patterning and skeletogenesis. *Development* 124: 4627-4638, 1997.
39. Joyner W L, Davis M J, and Gilmore J P. Intravascular pressure distribution and dimensional analysis of microvessels in hamsters with renovascular hypertension. *Microvascular Research* 22: 190-198, 1981.
40. Kesler C T, Liao S, Munn L L, and Padera T P. Lymphatic vessels in health and disease. *Wiley Interdiscip Rev Syst Biol Med* 5: 111-124, 2013.
41. Kriederman B M, Myloyde T L, Witte M H, Dagenais S L, Witte C L, Rennels M, Bernas M J, Lynch M T, Erickson R P, Caulder M S, Miura N, Jackson D, Brooks B P, and Glover T W. FOXC2 haploinsufficient mice are a model for human autosomal dominant lymphedema-distichiasis syndrome. *Human Molecular Genetics* 12: 1179-1185, 2003.
42. Leduc O, Crasset V, Leleu C, Baptiste N, Koziel A, Delahaie C, Pastouret F, Wilputte F, and Leduc A. Impact of manual lymphatic drainage on hemodynamic parameters in patients with heart failure and lower limb edema. *Lymphology* 44: 13-20, 2011.
43. Levick J R, and Michel C C. Microvascular fluid exchange and the revised Starling principle. *Cardiovascular Research* 87: 198-210, 2010.
44. Liao S, Cheng G, Conner D A, Huang Y, Kucherlapati R S, munn L L, Ruddle N H, Jain R K, Fukumura D, and Padera T P. Impaired lymphatic contraction associated with immunosuppression. *Proc Natl Acad Sci USA* 108: 18784-18789, 2011.
45. Maejima D, Kawai Y, Ajima K, and Ohhashi T. Platelet-Derived Growth Factor (PDGF)-BB Produces NO-Mediated Relaxation and PDGF Receptor b-Dependent Tonic Contraction in Murine Iliac Lymph Vessels. *Microcirculation* 18: 474-486, 2011.
46. McHale N G, and Roddie I C. The effect of transmural pressure on pumping activity in isolated bovine lymphatic vessels. *J Physiol* 261: 255-269, 1976.
47. Mellor R, Tate N, Stanton A, Hubert C, Makinen T, Smith A, Bumard K, Jeffery S, Levick J R, and Mortimer P S. Mutations in FOXC2 in humans (Lymphoedema Distichiasis Syndrone) cause lymphatic dysfunction on dependency. *Journal of Vascular Research* 48: 397-407, 2011.
48. Mellor R H, Brice G, Stanton A W, French J, Smith A, Jeffery S, Levick J R, Bumand K G, and Mortimer P S. Mutations in FOXC2 are strongly associated with primary valve failure in veins of the lower limb. *Circulation* 115: 1912-1920, 2007.
49. Mendez U, Brown E M, Ongstad E L, Slis J R, and Goldman J. Functional recovery of fluid drainage precedes lymphangiogenesis in acute murine foreleg. *American Journal of Physiology (Heart and Circulatory Physiology)* 302: H2250-H2256, 2012.
50. Mendez U, Stroup E M, Lynch L L, Waller A B, and Goldman J. A chronic and latent lymphatic insufficiency follows recovery from acute lymphedema in the rat foreleg. *American Journal of Physiology (Heart and Circulatory Physiology)* 303: H1107-H1113, 2012.
51. Mizuno R, Ono N, and Ohhashi T. Parathyroid hormone-related protein-(1-34) inhibits intrinsic pump activity of isolated murine lymph vessels. *Am J Physiol Heart Circ Physiol* 281: H60-66, 2001.
52. Modi S, Stanton A W, Svensson W E, Peters A M, Mortimer P S, and Levick J R. Human lymphatic pumping measured in healthy and lympoedematous arms by lymphatic congestion lymphoscintography. *Journal of Physiology* 583: 271-285, 2007.
53. Mortimer P S, and Levick J R. Chronic peripheral oedema: the critical role of the lymphatic system. *Clinical Medicine* 4: 448-453, 2004.
54. Normen C, Ivanov K I, Cheng J, Zangger N, Delorenzi M, Jaquet M, Muira N, Puolakkainen P, Horsley V, Hu J, Augustin H G, Yla-Herttuala S, Alitalo K, and Petrova T V. FOXC2 controls formation and maturation of lymphatic collecting vessels through cooperation with NFATc1. *Journal of Cell Biology* 195: 439-457, 2009.
55. Olszewski W L. Contractility patterns of normal and pathologically changed human lymphatics. *Annals of the New York Academy of Science* 979: 52-63, 2002.
56. Olszewski W L. Pathophysiological and clinical observations of obstructive lymphedema of the limbs. In: *Lymphedema*, edited by Clodius L. Stuttgart: Georg Thieme Publishers, 1977, p. 79-102.
57. Olszewski W L, and Engeset A. Intrinsic contractility of leg lymphatics in man: preliminary communication. *Lymphology* 12: 81-84, 1979.
58. Olszewski W L, and Engeset A. Intrinsic contractility of prenodal lymph vessels and lymph flow in human leg. *American Journal of Physiology (Heart and Circulatory Physiology)* 239: H775-H783, 1980.
59. Ono N, Mizuno R, Nojiri H, and Ohhashi T. Development of an experimental apparatus for investigating lymphatic pumping activity of murine mesentery in vivo. *Japanese J Physiology* 50: 25-31, 2000.
60. Petrova T V, Karpanen T, Norrmen C, Mellor R, Tamakoshi T, Finegold D, Ferrell R, Kerjaschki D, Mortimer P S, Yla-Herttuala S, Miura N, and Alitalo K. Defective valves and abnormal mural cell recruitment underlie lymphatic vascular failure in lymphedema distichiasis. *Nature Medicine* 10: 974-981, 2004.
61. Rockson S G. Lymphedema. *Curr Treat Options Cardiovasc Med* 8: 129-136, 2006.
62. Rockson S G. Precipitating factors in lymphedema: myths and realities. *Cancer* 15: 2814-2816, 1998.
63. Rockson S G. Secondary lymphedema: is it a primary disease? *Lymphatic Research & Biology* 6: 63-64, 2008.
64. Rockson S G, and Rivera K K. Estimating the population burden of lymphedema. *Annals of the New York Academy of Science* 1131: 147-154, 2008.
65. Rutkowski J M, Moya M, Johannes J, Goldman J, and Swartz M A. Secondary lymphedema in the mouse tail: Lymphatic hyperplasia, VEGF-C upregulation, and the protective role of MMP-9. *Microvasc Res* 72: 161-171, 2006.
66. Sabine A, Agalarov Y, Hajjami H M-E, Jaquet M, Hagerling R, Pollmann C, Bebber D, Pfenniger A, Miura N, Dormond O, Calmes J-M, Adams R H, Makinen T, Kiefer F, Kwak B, and Petrova T V. Mechanotransduction, 66. PROXI, and FOXC2 cooperate to control connexin37 and calcineurin during lymphatic-valve formation. *Developmental Cell* 22: 1-16, 2012.
67. Sabine A, Scallan J P, Davis M J, and Petrova T V. FOXC2 is essential for lymphatic valve maintenance and function. *Nature Medicine* (submitted).
68. Scallan J P, and Davis M J. Ex vivo transgenic models enable quantification of lymphatic vessel permeability. *Journal of Physiology* (submitted): 2013.
69. Scallan J P, and Davis M J. Genetic ablation of nitric oxide enhances contractile function of murine isolated popliteal afferent collecting lymphatic vessels. *Journal of Physiology* 591: 2139-2156, 2013.
70. Scallan J P, Sabine A, Gashev A A, Zawieja D C, Petrova T V, and Davis M J. Lymphatic valve lock: a contributing mechanism to peripheral lymphedema. *Circulation Research* (submitted).
71. Scallan J P, Wolpers J H, and Davis M J. Constriction of isolated collecting lymphatic vessels in response to acute increases in downsteam pressure. *Journal of Physiology* 591: 443-449, 2012.
72. Scallan J P, Wolpers J H, Muthuchamy M, Zawieja D C, Gashev A A, and Davis M J. Independent and interactive effects of preload and afterload on the lymphatic pump. *American Journal of Physiology (Heart and Circulatory Physiology)* 303: H809-H824, 2012.
73. Schmid-Schönbein G W. Microlymphatics and lymph flow. *Physiological Reviews* 70: 987-1028, 1990.
74. Shin W S, Szuba A, and Rockson S G. Animal models for the study of lymphatic insufficiency. *Lymphatic Research & Biology* 1: 159-169, 2003.
75. Stanton A W, Modi S, Mellor R H, Levick J R, and Mortimer P S. Recent advances in breast cancer-related lymphedema of the arm: lymphatic pump failure and predisposing factors. *Lymphatic Research & Biology* 7: 29-45, 2009.
76. Stanton A W B, Modi S, Britton T M B, Purushotham A D, Peters A M, Levick J R, and Mortimer P S. Lymphatic drainage in the muscle and subcutis of the arm after breast cancer treatment. *Breast Cancer Research Treatment* 117: 549-557, 2009.
77. Szuba A, and Rockson S G. Lymphedema: anatomy, physiology and pathogenesis. *Vascular Medicine* 2: 321-326, 1997.
78. Szuba A, Shin W S, Strauss H W, and Rockson S G. The third circulation: radionuclide lymphoscintigraphy in the evaluation of lymphedema. *Journal of Nuclear Medicine* 44: 43-57, 2003.
79. Tilney N L. Patterns of lymphatic drainage in the adult laboratory rat. *Journal of Anatomy* 109: 369-383, 1971.
80. Trayes K P, and Studdiford J S. Edema: Diagnosis and Management. *American Family Physician* 88: 102-110, 2013.
81. Unthank J L, and Hogan R D. Modulation of the spontaneous contractions of the initial lymphatics of the bat's wing by arterial and venous occlusion. *Blood Vessels* 25:115-121, 1988.
82. Uzarski J, Drelles M B, Gibbs S E, Ongstad E L, Goral J C, McKeown K K, Raehl A M, Roberts M A, Pytowski B, Smith M R, and Goldman J. The resolution of lymphedema by interstitial flow in the mouse tail skin. *American Journal of Physiology (Heart and Circulatory Physiology)* 294: H1326-H1334, 2008.
83. von der Weid P Y, and Zawieja D C. Lymphatic smooth muscle: the motor unit of lymph drainage. *Int J Biochem Cell Biol* 36: 1147-1153, 2004.
84. Wang W, Nepiyushchikh Z, Chakraborty S, Zawieja S D, Gashev A A, Davis M J, and Muthuchamy M. Inhibition of myosin light chain phosphorylation decreases rat mesenteric lymphatic contractile activity. *American Journal of Physiology (Heart and Circulatory Physiology)* 297: H726-H734, 2009.
85. Wegria R, Zekert H, Walter K E, Entrup R W, De Schryver C, and Paiewonsky D. Effect of systemic venous pressure on drainage of lymph from thoracic duct. *American Journal of Physiology* 204: 284-268, 1963.
86. Weitman E S, Aschen S Z, Farias-Eisner G, Albano N, Cuzzone D A, Ghanta S, Zampell J C, Thorek D, and Mehara B J. Obesity impairs lymphatic fluid transport and dendritic cell migration to lymph nodes. *PLoS One* 8: e70703, 2013.
87. Wiig H, and Swartz M A. Interstitial fluid and lymph formation and transport: physiological regulation and roles in inflammation and cancer. *Physiological Reviews* 92: 1005-1060, 2012.
88. Witte C L, White M H, and Dumont A E. High flow failure of the lymph circulation. *Vascular Surgery* 11: 130-151, 1977.
89. Witte C L, and Witte M H. Disorders of Lymph Flow. *Academic Radiology* 2: 324-334, 1995.
90. Witte C L, and Witte M H. Pathophysiology of lymphatic insufficiency and principles of treatment. In: *Lymph stasis: pathophysiology, diagnosis and treatment*, edited by Olszewski W L. Boca Raton, *Fla.: CRC Press,* 1991, p. 327-344.
91. Witte M H, Dumont A E, Clauss R H, Rader B, Levine N, and Breed E. Lymph circulation in congestive heart failure: Effect of external thoracic duct drainage. *Circulation* 39: 723-733, 1969.
92. Zaugg-Vesti B, Dorffler-Melly J, Spiegel M, Wen S, Franzeck U K, and Bollinger A. Lymphatic capillary pressure in patients with primary lymphedema. *Microvasc Res* 46: 128-134, 1993.
93. Zhang R-Z, Taucer A, Gashev A A, Muthuchamy M, Zawieja D C, and Davis M J. Maximum shortening velocity of lymphatic muscle approaches that of striated muscle. *American Journal of Physiology (Heart and Circulatory Physiology)* (in press): 2013.
94. Zweifach B W, and Hargens A R. Factors influencing fluid movement between blood and terminal lymphatics. *Bibl Anat* 15: 499-503, 1977.
95. Zweifach B W, and Lipowsky H H. Pressure-flow relations in blood and lymph microcirculation. In: *Handbook of Physiology Section 2: The Cardiovascular System, Volume IV, Chp 7, p 297*, edited by Renkin E M, and Michel C C. Bethesda, *Md.: American Physiological Society,* 1984, p. 251-307.
96. Zweifach B W, and Prather J W. Micromanipulation of pressure in terminal lymphatics in the rat mesentery. *American Journal of Physiology* 228: 1326-1335, 1975.
97. Current rankings of Physiology Departments by extramural funding; The Physiologist 56(5):121, September 2013, published by the American Physiological Society)

What is claimed is:
1. A method to treat or prevent lymphedema in a subject having or suspected of having lymphedema, the method comprising topically or intradermally administering to the subject in need thereof a composition comprising a compound that affects a calcium channel transduction pathway, wherein the compound that affects the calcium channel pathway is a calcium channel agonist selected from the group consisting of BayK8644, BayK8643, BayO8495,

BayO9507, PN202-79, CGP28-392, RS30026, H160/51, YC170, FPL64176, *Goniopora* toxin, maitotoxin, atrotoxin, and palmitoyl carnitate.

2. The method of claim 1, wherein the composition further comprises a KATP channel inhibitor selected from the group consisting of glyburide, pinacidil, sodium 5-hydroxydecanoate, PNU-37883A (U-37883A), PNU-18177A, PNU-99963, phentolamine, alinidine, tedisamil, and ZM181,037, an alpha-adrenergic agonist selected from the group consisting of phenylephrine, methoxamine, tetrahydralazine, xylometazoline, midodrine, oxymetazoline, cirazoline, metaraminol, synephrine, amidephrine, indanidine, phenylpropanolamine, norfenefrine, noradrenaline (norepinephrine), chloroethylclonidine, and etilefrine, or combinations thereof.

3. The method of claim 1, wherein the composition further comprises an alpha-adrenergic agonist selected from the group consisting of phenylephrine, methoxamine, tetrahydralazine, xylometazoline, midodrine, oxymetazoline, cirazoline, metaraminol, synephrine, amidephrine, indanidine, phenylpropanolamine, norfenefrine, noradrenaline (norepinephrine), chloroethylclonidine, and etilefrine.

4. The method of claim 3, wherein the alpha-adrenergic agonist is selected from the group consisting of norepinephrine and phenylephrine.

5. The method of claim 1, wherein the calcium channel agonist is a L-type calcium channel agonist and is selected from the group consisting of BayK8644, BayR5417, and FPL64176.

6. The method of claim 1, wherein the calcium channel agonist is a L-type calcium channel agonist and is BayK8644.

7. The method of claim 1, wherein the composition further comprises a KATP channel inhibitor selected from the group consisting of glyburide, pinacidil, sodium 5-hydroxydecanoate, PNU-37883A (U-37883A), PNU-18177A, PNU-99963, phentolamine, alinidine, tedisamil, and ZM181,037.

8. The method of claim 2, wherein the composition comprises BayK8644 and glyburide.

9. The method of claim 1, wherein lymphatic vessel function is improved or restored due to relief of valve lock.

10. The method of claim 1, wherein the composition is topically or intradermally administered to an extremity of the subject.

11. The method of claim 1, wherein the lymphedema is due to pump weakening or valve lock.

12. The method of claim 1, wherein the lymphedema is secondary to obesity, congestive heart failure, hypertension, and/or peripheral vascular/venous disease.

* * * * *